(12) United States Patent
Klinman et al.

(10) Patent No.: US 6,977,245 B2
(45) Date of Patent: Dec. 20, 2005

(54) OLIGODEOXYNUCLEOTIDE AND ITS USE TO INDUCE AN IMMUNE RESPONSE

(75) Inventors: Dennis Klinman, Potomac, MD (US); Daniela Verthelyi, Potomac, MD (US); Ken Ishii, Osaka (JP); James J. Mond, Silver Spring, MD (US); Mayda Gursel, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 186 days.

(21) Appl. No.: 10/068,160

(22) Filed: Feb. 6, 2002

(65) Prior Publication Data

US 2003/0060440 A1 Mar. 27, 2003

Related U.S. Application Data

(63) Continuation-in-part of application No. 09/958,713, filed as application No. PCT/US00/09839 on Apr. 12, 2000.
(60) Provisional application No. 60/128,898, filed on Apr. 12, 1999.

(51) Int. Cl.$^7$ ............................................. A61K 48/00
(52) U.S. Cl. ........................ 514/44; 536/23.1; 536/25.5; 536/25.6
(58) Field of Search .................. 536/23.1, 25.5, 536/25.6; 514/44

(56) References Cited

U.S. PATENT DOCUMENTS

| | | | |
|---|---|---|---|
| 2,215,233 A | 9/1940 | Ruskin | |
| 3,906,092 A | 9/1975 | Hilleman et al. | |
| 3,911,117 A | 10/1975 | Ender | |
| 3,914,450 A | 10/1975 | Robbins et al. | |
| 4,544,559 A | 10/1985 | Gil et al. | |
| 4,741,914 A | 5/1988 | Kimizuka et al. | |
| 4,758,553 A | 7/1988 | Ogoshi | |
| 4,806,376 A | 2/1989 | Saeki et al. | |
| 4,956,296 A | 9/1990 | Fahnestock | |
| 4,963,387 A | 10/1990 | Nakagawa et al. | |
| 4,994,442 A | 2/1991 | Gil et al. | |
| 5,066,500 A | 11/1991 | Gil et al. | |
| 5,231,085 A | 7/1993 | Alexander et al. | |
| 5,234,811 A | 8/1993 | Beutler et al. | |
| 5,248,670 A | 9/1993 | Draper et al. | |
| 5,268,365 A | 12/1993 | Rudolph et al. | |
| 5,288,509 A | 2/1994 | Potman et al. | |
| 5,488,039 A | 1/1996 | Masor et al. | |
| 5,492,899 A | 2/1996 | Masor et al. | |
| 5,585,479 A | 12/1996 | Hoke et al. | |
| 5,591,721 A | 1/1997 | Agrawal et al. | |
| 5,602,109 A | 2/1997 | Masor et al. | |
| 5,612,060 A | 3/1997 | Alexander | |
| 5,614,191 A | 3/1997 | Puri et al. | |
| 5,650,156 A | 7/1997 | Grinstaff et al. | |
| 5,679,397 A | 10/1997 | Kuroda et al. | |
| 5,684,147 A | 11/1997 | Agrawal et al. | |
| 5,700,590 A | 12/1997 | Masor et al. | |
| 5,712,256 A | 1/1998 | Kulkarni et al. | |
| 5,723,335 A | 3/1998 | Hutcerson et al. | |
| 5,756,323 A | * 5/1998 | Kallenbach et al. | ........... 435/6 |
| 5,786,189 A | 7/1998 | Locht et al. | |
| 5,804,566 A | 9/1998 | Carson et al. | |
| 5,840,705 A | 11/1998 | Tsukuda et al. | |
| 5,849,719 A | 12/1998 | Carson et al. | |
| 5,895,652 A | 4/1999 | Giampapa | |
| 5,919,456 A | 7/1999 | Puri et al. | |
| 5,922,766 A | 7/1999 | Acosta et al. | |
| 5,976,580 A | 11/1999 | Ivey et al. | |
| 5,980,958 A | 11/1999 | Naylor et al. | |
| 5,994,126 A | 11/1999 | Stienman et al. | |
| 6,022,853 A | 2/2000 | Kuberasampath et al. | |
| 6,194,388 B1 | 2/2001 | Krieg et al. | |
| 6,207,646 B1 * | 3/2001 | Krieg et al. | ................... 514/44 |
| 6,214,806 B1 | 4/2001 | Krieg et al. | |
| 6,218,371 B1 | 4/2001 | Krieg et al. | |
| 6,239,116 B1 | 5/2001 | Krieg et al. | |
| 6,339,068 B1 | 1/2002 | Krieg et al. | |
| 6,406,705 B1 | 6/2002 | Davis et al. | |
| 6,423,539 B2 | 7/2002 | Fong et al. | |
| 6,428,788 B1 | 8/2002 | Debinski et al. | |
| 6,429,199 B1 | 8/2002 | Krieg et al. | |
| 6,498,148 B1 | 12/2002 | Raz | |
| 6,514,948 B1 | 2/2003 | Raz et al. | |
| 6,534,062 B2 | 3/2003 | Raz et al. | |
| 6,552,006 B2 | 4/2003 | Raz et al. | |
| 6,562,798 B1 | 5/2003 | Schwartz | |
| 6,589,940 B1 | 7/2003 | Raz et al. | |
| 6,610,661 B1 | 8/2003 | Carson et al. | |
| 6,613,751 B2 | 9/2003 | Raz et al. | |
| 6,653,292 B1 | 11/2003 | Krieg et al. | |
| 2001/0034330 A1 | 10/2001 | Kensil | |
| 2001/0036462 A1 | 11/2001 | Fong et al. | |
| 2001/0044416 A1 | 11/2001 | McCluskie et al. | |

(Continued)

FOREIGN PATENT DOCUMENTS

| | | |
|---|---|---|
| EP | 0 286 224 | 10/1988 |
| EP | 0 302 758 | 11/1989 |

(Continued)

OTHER PUBLICATIONS

Mahairas, PNAS, vol. 96, 17:9739–9744, 1999.*
NCBI database, AR009571, Dec. 1998.*

(Continued)

Primary Examiner—Dave Trong Nguyen
(74) Attorney, Agent, or Firm—Klarquist Sparkman, LLP

(57) ABSTRACT

D type CpG oligodeoxynucleotides are provided herein that include a sequence represented by the following formula:

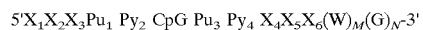

5'$X_1 X_2 X_3 Pu_1 Py_2$ CpG $Pu_3$ $Py_4$ $X_4 X_5 X_6 (W)_M (G)_N$-3' wherein the central CpG motif is unmethylated, Pu is a purine nucleotide, Py is a pyrimidine nucleotide, X and W are any nucleotide, M is any integer from 0 to 10, and N is any integer from 4 to 10. Methods of using these oligodeoxynucleotides to induce an immune response are provided.

13 Claims, 7 Drawing Sheets

U.S. PATENT DOCUMENTS

| | | |
|---|---|---|
| 2001/0046967 A1 | 11/2001 | Van Nest |
| 2002/0006403 A1 | 1/2002 | Yu et al. |
| 2002/0028784 A1 | 3/2002 | Van Nest |
| 2002/0042383 A1 | 4/2002 | Yew et al. |
| 2002/0042387 A1 | 4/2002 | Raz et al. |
| 2002/0055477 A1 | 5/2002 | Van Nest et al. |
| 2002/0064515 A1 | 5/2002 | Krieg et al. |
| 2002/0065236 A1 | 5/2002 | Yew et al. |
| 2002/0086295 A1 | 7/2002 | Raz et al. |
| 2002/0086839 A1 | 7/2002 | Raz et al. |
| 2002/0090724 A1 | 7/2002 | Taylor et al. |
| 2002/0091095 A1 | 7/2002 | Phillips et al. |
| 2002/0091097 A1 | 7/2002 | Bratzler et al. |
| 2002/0098199 A1 | 7/2002 | Van Nest et al. |
| 2002/0098205 A1 | 7/2002 | Choi et al. |
| 2002/0098980 A1 | 7/2002 | Choi et al. |
| 2002/0107212 A1 | 8/2002 | Van Nest et al. |
| 2002/0110569 A1 | 8/2002 | Granoff et al. |
| 2002/0111323 A1 | 8/2002 | Martin et al. |
| 2002/0136776 A1 | 9/2002 | Fang et al. |
| 2002/0137714 A1 | 9/2002 | Kandimalla et al. |
| 2002/0142974 A1 | 10/2002 | Kohn et al. |
| 2002/0142977 A1 | 10/2002 | Raz et al. |
| 2002/0142978 A1 | 10/2002 | Raz et al. |
| 2002/0156033 A1 | 10/2002 | Bratzler et al. |
| 2002/0164341 A1 | 11/2002 | Davis et al. |
| 2002/0165178 A1 | 11/2002 | Schetter et al. |
| 2002/0183272 A1 | 12/2002 | Johnston et al. |
| 2002/0197269 A1 | 12/2002 | Lingnau et al. |
| 2002/0198165 A1 | 12/2002 | Bratzler et al. |
| 2003/0003579 A1 | 1/2003 | Kadowaki et al. |
| 2003/0022849 A1 | 1/2003 | Chang |
| 2003/0022852 A1 | 1/2003 | Van Nest et al. |
| 2003/0026782 A1 | 2/2003 | Krieg |
| 2003/0026801 A1 | 2/2003 | Weiner et al. |
| 2003/0049266 A1 | 3/2003 | Fearon et al. |
| 2003/0050261 A1 | 3/2003 | Krieg et al. |
| 2003/0050263 A1 | 3/2003 | Krieg et al. |
| 2003/0050268 A1 | 3/2003 | Krieg et al. |
| 2003/0052839 A1 | 3/2003 | Binley et al. |
| 2003/0055014 A1 | 3/2003 | Bratzler |
| 2003/0059773 A1 | 3/2003 | Van Nest et al. |
| 2003/0060440 A1 | 3/2003 | Klinman et al. |
| 2003/0064064 A1 | 4/2003 | Dina |
| 2003/0072762 A1 | 4/2003 | Van de Winkel et al. |
| 2003/0073142 A1 | 4/2003 | Chen et al. |
| 2003/0078223 A1 | 4/2003 | Raz et al. |
| 2003/0091599 A1 | 5/2003 | Davis et al. |
| 2003/0092663 A1 | 5/2003 | Raz |
| 2003/0096417 A1 | 5/2003 | Fischer |
| 2003/0100527 A1 | 5/2003 | Krieg et al. |
| 2003/0104044 A1 | 6/2003 | Semple et al. |
| 2003/0104523 A1 | 6/2003 | Lipford et al. |
| 2003/0109469 A1 | 6/2003 | Carson et al. |
| 2003/0119773 A1 | 6/2003 | Raz et al. |
| 2003/0119774 A1 | 6/2003 | Foldvari et al. |
| 2003/0119776 A1 | 6/2003 | Phillips et al. |
| 2003/0125284 A1 | 7/2003 | Raz et al. |
| 2003/0129251 A1 | 7/2003 | Van Nest et al. |
| 2003/0130217 A1 | 7/2003 | Raz et al. |
| 2003/0133988 A1 | 7/2003 | Fearon et al. |
| 2003/0135875 A1 | 7/2003 | Ehrhardt et al. |
| 2003/0138413 A1 | 7/2003 | Vicari et al. |
| 2003/0138453 A1 | 7/2003 | O'Hagan et al. |
| 2003/0139364 A1 | 7/2003 | Krieg et al. |
| 2003/0143213 A1 | 7/2003 | Raz et al. |
| 2003/0143743 A1 | 7/2003 | Schuler et al. |
| 2003/0144229 A1 | 7/2003 | Klinman et al. |
| 2003/0147870 A1 | 8/2003 | Raz et al. |
| 2003/0148316 A1 | 8/2003 | Lipford et al. |
| 2003/0148976 A1 | 8/2003 | Krieg et al. |
| 2003/0148983 A1 | 8/2003 | Fontoura et al. |
| 2003/0157717 A1 | 8/2003 | Draghia-Akli |
| 2003/0158136 A1 | 8/2003 | Rice et al. |
| 2003/0165478 A1 | 9/2003 | Sokoll |
| 2003/0166001 A1 | 9/2003 | Lipford |
| 2003/0170273 A1 | 9/2003 | O'Hagan et al. |
| 2003/0171321 A1 | 9/2003 | Schmidt et al. |
| 2003/0175731 A1 | 9/2003 | Fearon et al. |
| 2003/0176373 A1 | 9/2003 | Raz et al. |
| 2003/0176389 A1 | 9/2003 | Raz et al. |
| 2003/0180320 A1 | 9/2003 | Darju et al. |
| 2003/0181406 A1 | 9/2003 | Schetter et al. |
| 2003/0185848 A1 | 10/2003 | Johnston et al. |
| 2003/0185900 A1 | 10/2003 | Choi et al. |
| 2003/0186921 A1 | 10/2003 | Carson et al. |
| 2003/0191079 A1 | 10/2003 | Krieg et al. |
| 2003/0199466 A1 | 10/2003 | Fearon et al. |
| 2003/0203861 A1 | 10/2003 | Carson et al. |
| 2003/0206967 A1 | 11/2003 | Choi et al. |
| 2003/0207287 A1 | 11/2003 | Short |
| 2003/0212026 A1 | 11/2003 | Krieg et al. |
| 2003/0212028 A1 | 11/2003 | Raz et al. |
| 2003/0216340 A1 | 11/2003 | Van Nest et al. |
| 2003/0219752 A1 | 11/2003 | Short |
| 2003/0220277 A1 | 11/2003 | Yew et al. |
| 2003/0224010 A1 | 12/2003 | Davis et al. |
| 2003/0225016 A1 | 12/2003 | Fearon et al. |
| 2003/0232780 A1 | 12/2003 | Carson et al. |
| 2004/0005588 A1 | 1/2004 | Cohen et al. |
| 2004/0006010 A1 | 1/2004 | Carson et al. |
| 2004/0006032 A1 | 1/2004 | Lopez |
| 2004/0006034 A1 | 1/2004 | Raz et al. |
| 2004/0009897 A1 | 1/2004 | Sokoll |
| 2004/0009942 A1 | 1/2004 | Van Nest |
| 2004/0009949 A1 | 1/2004 | Krieg |
| 2004/0013686 A1 | 1/2004 | Granoff et al. |
| 2004/0013688 A1 | 1/2004 | Wise et al. |
| 2004/0028693 A1 | 2/2004 | Wu et al. |

FOREIGN PATENT DOCUMENTS

| | | |
|---|---|---|
| EP | 0 468 520 A2 | 1/1991 |
| EP | 0 092 574 | 4/1992 |
| EP | 0 572 735 A1 | 12/1993 |
| EP | 0 855 184 A1 | 7/1998 |
| EP | 1 198 249 | 4/2002 |
| WO | WO 91/12811 | 9/1991 |
| WO | WO 92/03456 | 4/1992 |
| WO | WO 92/18522 | 10/1992 |
| WO | WO 92/21353 | 12/1992 |
| WO | WO 93/17115 | 9/1993 |
| WO | WO 94/19945 | 9/1994 |
| WO | WO 95/05853 | 3/1995 |
| WO | WO 95/18231 | 7/1995 |
| WO | WO 95/26204 | 10/1995 |
| WO | WO 96/02555 | 2/1996 |
| WO | WO 96/24380 | 2/1996 |
| WO | WO 96/35782 | 11/1996 |
| WO | WO 97/28259 | 1/1997 |
| WO | WO 98/29430 | 12/1997 |
| WO | WO 98/14210 | 4/1998 |
| WO | WO 98/16247 | 4/1998 |
| WO | WO 98/18810 | 5/1998 |
| WO | WO 98/32462 | 7/1998 |
| WO | WO 98/37919 | 9/1998 |
| WO | WO 98/38319 | * 9/1998 |
| WO | WO 98/49348 | 11/1998 |
| WO | WO 98/52581 | 11/1998 |
| WO | WO 98/55495 | 12/1998 |
| WO | WO 99/11275 | 3/1999 |
| WO | WO 99/37151 | 7/1999 |

| | | |
|---|---|---|
| WO | WO 99/51259 | 10/1999 |
| WO | WO 99/56755 | 11/1999 |
| WO | WO 99/58118 | 11/1999 |
| WO | WO 99/61056 | 12/1999 |
| WO | WO 99/62923 | 12/1999 |
| WO | WO 00/14217 | 3/2000 |
| WO | WO 00/20039 | 4/2000 |
| WO | WO 00/21556 | 4/2000 |
| WO | WO 00/06588 | 10/2000 |
| WO | WO 00/61151 | 10/2000 |
| WO | WO 00/62787 | 10/2000 |
| WO | WO 00/67023 | 11/2000 |
| WO | WO 00/67787 | 11/2000 |
| WO | WO 01/00232 | 1/2001 |
| WO | WO 01/02007 | 1/2001 |
| WO | WO 01/12223 | 2/2001 |
| WO | WO 01/12804 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 02/69369 | 9/2002 |

OTHER PUBLICATIONS

NCBI Database, A86868, Jan. 2000.*

Gene Bank database, AN:: Aq834558/c, Aug. 1999.*

Alama et al., Antisense Oligonucleotides as Therapeutic Agents,: *Pharmacol. Res.* 36: 171 (1997).

Ballas et al., "Induction of NK Activity in Murine and Human Cells by CpG Motifs in Oligodeoxynucleotides and Bacterial DNA," *J. Immun.* 157: 1840 (1996).

Klinman et al., "CpG Motifs Present in Bacterial DNA Rapidly Induce Lymphocytes to Secrete Interleukin 6, Interleukin 12 and Interferon γ," *Proc. Natl. Acad. Sci. USA* 93: 2879 (1996).

Kreig et al., "CpG Motifs in Bacterial DNA Trigger Direct B–Cell Activation," *Nature* 374: 546 (1995).

Krieg et al., "CpG Motifs in Bacterial DNA Trigger Direct B–Cell Activation," *Nature* 374: 546 (1995).

Liang et al., "Activation of Human B Cells by Phosphorothioate Oligodeoxynucleotides," *J. Clin. Invest.* 98: 1119 (1996).

Lonnberg et al., "Towards Genomic Drug Therapy with Antisense Oligonucleotides," *Ann. Med.* 28: 511 (1996).

McCluskie et al., "CpG DNA is a Potent Enhancer of Systemic & Mucosal Immune Response Against Hepatitis B Surface Antigen with Intra–Nasal Administration to Mice," *J. Immun.* 161: 4463 (1998).

Oberauer, "Not Non–Sense but Antisense—Applications of Antisense Oligonucleotides in Different Fields of Medicine," *Wein Klin Wochenschr* 109: 40 (1997).

Scanlon et al., "Oligonucleotides–Mediated Modulation of Mammalian Gene Expression," *FASEB J.* 9: 1288 (1995).

Yi et al., "Rapid Immune Activation by CpG Motifs in Bacterial DNA," *J. Immun.* 157: 5394 (1996).

Adya, et al., "Expansion of CREB's DNA recognition specificity by Tax results from interaction with Ala–Ala–Arg at positions 282–284 near the conserved DNA–binding domain of CREB". Proc. Natl. Acad. Sci. USA 91(12):5642–5646 (1994).

Agrawal, et al., "Pharmacokinetics of Oligonucleotides". Ciba. Found. Symp. 209:60–78 (1997), abstract only.

Agrawal, et al., "Pharmacokinetics and Bioavailability of Antisense Oligonucleotides Following Oral and Colorectal Administration of Experimental Animals". Handb. Exp. Pharmacol.: Antisense Research and Application 131:525–543 (1998).

Agrawal, "Antisense Oligonucleotides: Toward Clinical Trials". Tibtech 14:376–387 (1996).

Agrawal, et al., "In Vivo Pharmacokinetics of Phosphorothioate Oligonucleotides Containing Contiguous Guanosines". Antisense & Nucleic Acid Drug Development 7:245–249 (1997).

Agrawal, et al., "Absorption, Tissue Distribution and In Vivo Stability in Rats of a Hybrid Antisense Oligonucleotide Following Oral Administration". Biochemical Pharmacology 50(4):571–576 (1995).

Agrawal, et al., "Pharmacokinetics of Antisense Oligonucleotides". Clin. Pharmacokinet 28(1):7 (1995).

Agrawal, et al., "Antisense therapeutics: is it as simple as complementary base recognition?". Molecular Med. Today 6(2):72–81 (2000), abstract only.

Agrawal, et al., "Pharmacokinetics, biodistribution, and stability of oligodeoxynucleotide phosphorothioates in mice". Proc. Natl. Acad. Sci. USA 88:7595–7599 (1991).

Agrawal, "Medicinal Chemistry and Therapeutic Potential of CpG DNA". Trends in Molecular Medicine 8(3):114–121 (2002).

Amaral, et al., "*Leishmania amazonensis*: The asian rhesus macaques (*Macaca mulatta*) as an experimental model for study of cutaneous leishmaniasis". Exp. Parasitol. 82(1):34–44 (1996).

Anderson, "Human Gene Therapy". Nature 392:25–30 (Apr. 1998).

Anderson, et al., "TH2 and 'TH2–like' cells in allergy and asthma; pharmacological perspectives". TiPS 15:324–332 (1994).

Anfossi, et al., "An oligomer complementary to c–myb–encoded mRNA inhibits proliferation of human myeloid leukemia cell lines". Proc. Natl. Acad. Sci. USA 86:3379–3383 (May 1989).

Angier, "Microbe DNA seen as alien by immune system". New York Times Page C1, 2 pages (1995).

Azad, et al., "Antiviral activity of a phosphorothioate oligonucleotide complementary to RNA of the human cytomegalovirus major immediate–early region". Amtimicrobial Agents and Chemotherapy 37:1945–1954 (1993).

Azuma, "Biochemical and immunological studies on cellular components of tubercle bacilli", Kekkaku 69(9):45–55 (1992).

Azzoni, et al., "Sustained Impairment of IFN–γ Secretion in Suppressed HIV–Infected Patients Despite Mature NK Cell Recovery: Evidence for a Defective Reconstruction of Innate Immunity". J. Immunol. 168(11):5764–5770 (2002).

Banchereau, et al., "Immunobiology of Dendritic Cells". Ann. Rev. Immunol. 18:767–811 (2000).

Banchereau & Steinman, "Dendritic Cells and the Control of Immunity". Nature 392:245–252 (1998).

Barouch, et al., "Control of Viremia and Prevention of Clinical AIDS in Rhesus Monkeys by Cytokine–Augmented DNA Vaccination". Science 290:486–492 (Oct, 2000).

Bauer, et al., "Bacterial CpG–DNA Triggers Activation and Maturation of Human CD11c–, CD123+ Dendritic Cells". J. Immunol. 166:5000–5007 (2001).

Bayever, "Systemic administration of a phosphorothioate oligonucleotide with a sequence complementary to p53 for acute myelogenous leukemia and myelodysplastic syndrome: initial results of a Phase I trial". Antisense Res. Dev. 3:383–390 (1993).

Benimetskaya, et al., "Formation of a G–tetrad and higher order structures correlates with biological activity of the RelA (NF–kBp65) 'antisense' oligodeoxynucleotide". Nucleic Acids Research 25(13):2648–2656 (1997).

Bennett, et al., "DNA binding to human leukocytes: evidence for a recptor–mediated association, internalization, and degradation of DNA". J. Clin. Invest. 76(6):2182–2190 (1985).

Berg, et al., "Interleukin–10 is a central regulator fo the response to LPS in murine models of endotoxic shock and the Shwartzman reaction but not endotoxin tolerance". J. Clin. Invest. 96(5):2339–2347 (1995).

BIOLABS, "1988–1989 Catalog, Random Primer #s 1230, 1601, 1602". ().

Bishop, et al., "Intramolecular G–quartet Motifs Confer Nuclease Resistance to a Potent Anti–HIV Oligonucleotide". The Journal of Biological Chemistry 271(10):5698–5703 (Mar. 1996).

Blanchard, et al., "Interferon–γInduction by Lipopolysaccharide: Dependence of Interleukin 2 and Macrophages". The Journal of Immunology 136(3):963–970 (Feb. 1986).

Blanco, et al., "Induction of Dendritic Cell Differentiation by IFN–α in Systemic Lupus Erythermatosus". Science 294:1540–1543 (2001).

Blaxter, et al., "Genes expressed in *Brugia malayi* infective third stage larvae". Mol. Biochem. Parasitol. 77:77–93 (1996).

Boggs, et al., "Characterization and modulation of immune stimulation by modified oligonucleotides". Antisense Nucl. Acid Drug Dev. 7(5):461–471 (1997).

Boiarkina, et al., "Dietary supplemental from ground fish meat with DNA for treatment and prophylaxis". Vopr. Pitan 1:29–31 (1998), abstract only.

Branda, et al., "Immune stimulation by an antisense oligomer complemetary to the rev genes of HIV–1". Biochem. Pharmacol. 45(10):2037–2043 (1993).

Branda, et al., "Amplification of antibody production by phosphorothioate oligodeoxynucleotides". J. Lab Clin. Med. 128(3):329–338 (1996).

Briskin, et al., "Lipopolysaccharide–unresponsive mutant pre–B–cell lines blocked in NF–kappa B activation". Mol. Cell Bio. 10(1):422–425 (1990).

Burgess, "The antiproliferative activity of c–myb and c–myc antisense oligonucleotides in smooth muscle cells is caused by a nonantisense mechanism". Proc. Natl. Acad. Sci. USA 92:4051–4055 (Apr. 1995).

Calarota, et al., "Immune Responses in Asymptomatic HIV–1 Infected patients After HIV–DNA Immunization Followed by Highly Active Antiretroviral Threatment". J. Immunol. 163(4):2330–2338 (1999).

Chace, et al., "Regulation of differentiation in CD5+ and conventional B cells". Clin. Immunol. Immunopathol. 68(3):327–332 (1993).

Chang, et al., "The palindromic series I repeats in the simian cytomegalovirus major immediate–early promoter behave as both strong basal enhancers and cyclic AMP response elements". J. Virol. 64(1):264–277 (1990).

Chapuis, et al., "Differentiation of Human Dendritic Cells from Monocytes in vitro". Eur. J. Immunol. 27:431–441 (1997).

Chehimi, "Persistent Decreases in Blood Plasmacytoid Dendritic Cell Number and Function Despite Effective Highly Active Antiretroviral Therapy and Increased Blood Myeloid Dendritic Cells in HIV–Infected Individuals". J. Immunol. 168(9):4796–4801 (2002).

Chu, et al., "CpG oligodeoxynucleotides act as adjuvants that switch on T helper 1 (Th1) immunity". J. Exp. Med. 186(10):1623–1631 (1997).

Chun, et al., "Effect of interleukin–2 on the pool of latently infected, resting CD4+ T–cells in HIV–1–infected patients receiving highly active anti–retroviral therapy". Nature Med. 5(6):651–655 (1999).

Chun, et al., "Perspective: Latent reservoirs of HIV: Obstacles to the eradication of virus". Proc. Natl. Acad. Sci. USA 96:10958–10961 (1999).

Cohen, et al., "Exploring How to Get at—and Eradicate—Hidden HIV". Science 279:1854–1855 (1998).

Cohen & Fauci, et al., "HIV/AIDS in 1998—Gaining the Upper Hand?". JAMA 280(1):87–88 (1998).

Cook, et al., "Effect of a Single Ethanol Exposure in HIV Replication in Human Lymphocytes". J. Invest. Med. 45(5):265–271 (1997).

Cooper, et al., "Therapeutic Strategies for HIV Infection—Time To Think Hard". The New England Journal of Medicine 339(18):1319–1321 (1998).

Cowdery, et al., "Bacterial DNA induces NKcells to product IFN–gamma in vivo and increases the toxici of lipopolysaccharides". J. Immunol. 156(12):4570–4575 (1996).

Crosby, et al., "The early responses gene NGFI–C encodes a zinc finger transcriptional activator and is a member of the GCGGGGGCG (GSG) element–binding protein family". Mol. Cell Bio. 2:3835–3841 (1991).

Crystal, "Transfer of genes to humans: early lessons and obstacles to success". Science 270:404–410 (1995).

Cryz, et al., "Vaccine Delivery System—European Commission COST/STD Initiative Report of the Expert Panel VII". Vaccine 14(7):665–690 (1996).

D'Andrea, et al., "Interleukin 10 (IL–10) inhibits human lymphocyte interferon gamma–production by suppressing natural killer cell stimulatory factor/IL–12 synthesis in accessory cells". J. Exp. Med. 178(3):1041–1048 (1993).

Davey, et al., "HIV–1 and T–Cell dynamics after interruption of highly antiretroviral therapy (HAART) in patients with a history of sustained viral suppression". Proc. Natl. Acad. Sci. USA 96(26):15109–15114 (1999).

Davis, et al., "CpG DNA is a Potent Enhancer of Specific Immunity in Mice Immunized with Recombinant Hepatitis B Surface Antigen". J. Immunol. 160(2):870–876 (1998).

Davis, "Plasmid DNA expression systems for the purpose of immunization". Curr. Opin. Biotechnol. 8(5):635–646 ( Oct. 1997).

Dematos, et al., "Pulsing of Dendritic Cells with Cell Lysates from Either B16 Melanoma or MCA–106 Fibrosarcoma Yields Equally Effective Vaccines Against B16 Tumors in Mice". J. Surg. Oncol. 68:79–91 (1998).

Deml, et al., "Immunostimulatory CpG motifs trigger a T Helper–1 immune response to Human Immunodeficiency Virus Type–1 (HIV–1) gp160 envelope protein". Clin. Chem. Lab. Med. 37(3):199–204 (1999).

Dias et al., "Minireview: Antisense Oligonucleotides: Basic Concepts and Mechanisms," *Mol. Can. Ther.* 1:347–355, 2002.

Doerfler, et al., "On the Insertion of Foreign DNA into Mammalian Genomes: Mechanism and Consequences". Gene 157(1–2):241–254 (1995), abstract only.

Durham, et al., "Immunotherapy and Allergic Inflammation". Clin. Exp. Allergy 21 Suppl 1:206–210 (1991).

Eck, et al., "Chapter 5: Gene–Based Therapy". Goodman & Gilman's The Pharmacological Basis of Therapeutics 9th ed.:77–101 (1996).

Elkins, et al., "Bacterial DNA containing CpG motifs stimulates lymphocyte–dependent protection of mice against lethal infection with intracellular bacteria". J. Immunol. 162:2291–2298 (1999).

Englisch, et al., "Chemically modified oligonucleotides as probes and inhibitors". Angew. Chem. Int. Ed. Engl. 30:613–629 (1991).

Erb, et al., "Infection of mice with Mycobacterium bovis-badillus Calmette–Guerin (BCG) supresses allergen–induced airway eosinophilia". J. Exp. Med. 184(4):561–569 (1998).

Etlinger, "Carrier sequence selection—one key to successful vaccines". Immunology Today 13(2):52–55 (1992).

Fanslow, et al., "Effect of Nucleotide Restriction and Supplementation on Resistance to Experimental Murine Candidasis". J. Parenter. Enteral. Nutr. 12(1):49–52 Abstract (1988).

Fields, et al., "Murine Dendritic Cells Pulsed With Whole Tumor Lysates Mediate Potent Antitumor Immune Response in vitro and in vivo". Proc. Natl. Acad. Sci. USA 95:9482–9487 (1998).

Filion, et al., "Major Limitations in the use of Cationic Liposomes for DNA Delivery". Int. J. Pharmaceuticals 162:159–170 (1998).

Fox, "Mechanism of action of hydroxychloroquine as an antirheumatic drug". Chem. Abstracts 120:15, Abstract No. 182630 (1 page) (1994).

Freidag, et al., "CpG oligodeoxynucleotides and interleukin–12 improve the efficacy of *Mycobacterium bovis* BCG vaccination in mice challenged with M. tuberculosis". Infect. Immun. 68:2948–2953 (2000).

Gao, et al., "Phosphorothioate oligonucleotides are inhibitors of human DNA polymerases and Rnase H: Implications for antisense technology". Mol. Pharmacol. 41:223–229 (1992).

Garraud, "Regulation of Immunoglobin Production in Hyper–IgE (Job's) Syndrome". J. Allergy Clin. Immunol. 103(2 Pt 1):333–340 (Feb. 1999).

Gluckman, et al., "In Vitro Generation of Human Dendritic Cells and Cell Therapy". Cytokines Cell Mol. Ther. 3:187–196 (1997).

Gramzinski, et al., "Interleukin–12– and gamma interferon–dependent protection against malaria conferred by CpG oligodeoxynucleotide in mice". Infect. Immun. 69(3):1643–1649 (2001).

Gura, "Antisense has growing pains". Science 270:575–576 (1995).

Gursel, "Sterically Stabilized Cationic Liposomes Improve the Uptake and Immunostimulatory Activity of CpG Oligonucleotides". J. Immunol. 167(6):3324–3328 (2001).

Gursel, et al., "Differential and Competitive Activation of Human Immune Cells by Distinct Classes of CpG Oligodeoxynucleotide". J. Leuko. Biol. 71:813–820 (2002).

Hadden, et al., "Immunopharmacology". JAMA 268(20):2964–2969 (1992).

Hadden, et al., "Immunostimulants". TiPS 141:169–174 (1993).

Halpern, et al., "Bacterial DNA induces murine interferon-gamma production by stimulation of interleukin–12 and tumor necrosis factor–alpha". Cell Immunol. 167(1):72–89 (1996).

Haslett, et al., "Strong Human Immunodeficiency Virus (HIV) Specific CVD4+ T Cell Responses in a Cohort of Chronically Infected Patients are Associated with Interruptions in Anti–HIV Chemotherapy", J. Infect. Diseases 181:1264–1272 (2000).

Hatzfeld, "Release of early human hematopoietic progenitors from quiescence by antisense transformin owth factor β1 or Rb oligonucleotides". J. Exp. Med. 174:925–929 (1991).

Havlir, et al., "Maintenance Antiretroviral Therapies in HIV–Infected Subjects with Undetectable Plasma HIV RNA after Triple–Drug Therapy". The New England Journal of Medicine 339(18):1261–1268 (1998).

Hayashi, et al., "Enhancement of innate immunity against *Mycobacterium avium* infection by immunostimulatory DNA is mediated by indoteamine 2,3–dioxygenase". Infect. Immun. 69:6156–6164 (2001).

Hertl, et al., "Inhibition of Interferon–γ–Induced Intercellular Adhesion Molecule–1 Expression on Human Keratinocytes by Phosphorothioate Antisense Oligodeoxynucleotides is the Consequence of Antisense–Specific and Antisense–Non–Specific Effects". The Journal of Investigative Dermatology 104(5):813–818 (May 1995).

Highfield, "Sepsis: the more, the murkier". Biotechnology 12:828 (1994).

Hoeffler, et al., "Identification of multiple nuclear factors that interact with cyclic adenosine 3',5', monophosphate response element–binding protein and activating transcription factor–2 by protein–protein interactions". Mol. Endocrinol. 5(2):256–266 (1991).

Honess, et al., "Deviations from Expected Frequencies of CpG Dinucleotides in Herpesvirus DNAs May be Diagnostic of Differences in the States of Their Latent Genomes". J. Gen. Vir. 70(4):837–855 (1989).

Horspool, et al., "Nucleic acid vaccine–induces immune responses require CD28 costimulation and are regulated by CTLA4". J. Immunol. 160:2706–2714 (1998).

Hughes, et al., "Influence of Base Composition on Membrane Binding and Cellular Uptake of 10–mer Phosphorothioate Oligonucleotides in Chinese Hamster Ovary (CHRC5) Cells". Antisense Research and Development 4:211–215 (1994).

Iguchi–Ariga, et al., "CpG methylation of the cAMP–responsive enhancer/promoter sequence TGACGTCA abolishes specific factor binding as well as transcriptional activation". Genes Dev. 3(5):612–619 (1989).

Imami, et al., "Assessment of Type 1 and Type 2 Cytokines in HIV Type 1–Infected Individuals: Impact of Highly Active Antiretroviral Therapy". AIDS Research and Human Retroviruses 15(17):1499–1508 (1999).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531–6536 (2000).

Ishikawa, et al., "IFN induction and associated changes in splenic leukocyte distribution". J. Immunol. 150(9):3713–3727 (1993).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43–52 (1994).

Jakway, et al., "Growth regulation of the B lymphoma cell line WEHI–23 1 by anti–immunoglobulin, lipopolysaccharide, and other bacterial products". J. Immunol. 137(7):2225–2231 (1996).

Jaroszewski, et al., "Cellular uptake of antisense oligonucleotides". Adv. Drug Delivery Rev. 6(3):235–250 (1991).

Jilek, et al., "Antigen–Independent Suppression of the Allergic Immune Response to Bee Venom Phospholipase A2 by DNA Vaccination in CBA/J Mice". J. Immunol. 166:3612–3621 (2001).

Jones, et al., "Synthetic Oligonucleotides Containing CpG Motifs Enhance Immunogenicity of a Peptide Malaria Vaccine in Aotus Monkeys". Vaccine 17:3065–3071 (1999).

Juffermans, et al., "CpG oligodeoxynucleotides enhance host defense during murine tuberculosis". Infect. Immun. 70:147–152 (2002).

Kadowaki, et al., "Distinct CpG DNA and Polyinosinic–Polycytidylic Acid Double Stranded RNA, Respectively, Stimulate CD11c– Type 2 Dendritic Cell Precursoes and CD11c+ Dendritic cells to Produce Type I IFN". J. Immunol. 166:2291–2295 (2001).

Kataoka, et al., "Antitumor activity of synthetic oligonucleotides with sequences from cDNA encodin proteins of *Mycobacterium bovis* BCG". Jpn. J. Cancer Res. 83:244–247 (1992).

Kenney, et al., "Protective Immunity Using Recombinant Human IL–12 and Alum as Adjuvants in a Primate Model of *Cutaneous leishmaniasis*". J. Immunol. 163(8):4481–4488 (1999).

Khaled, et al., "Multiple mechanisms may contribute to the cellular anti–adhesive effects of phosphorothioate oligodeoxynucleotides". Nucleic Acids Research 24(4):737–745 (1996).

Kimura, et al., "Binding of oligoguanylate to scavenger receptors is required for oligonucleotides to augment NK cell activity and induce IFN". J. Biochem 116(5):991–994 (1994).

Kline, et al., "CpG motif oligonucleotides are effective in prevention of eosinophilic inflammation in a murine model of asthma". J. Invest. Med. 44(7):380A (1 page) (1996).

Kline, et al., "CpG oligonucleotides can reverse as well as prevent TH2–mediated inflammation in a murine model of asthma". J. Invest. Med. 45(7):298A (1 page) (1997).

Kline, et al., "Immune redirection by CpG oligonucleotides, Conversion of a Th2 response to a Th1 response in a murine model of asthma". J. Invest. Med. 45(3):282A (1 page) (1997).

Klinman, et al., "Immune recognition of foreign DNA: a cure for bioterrorism?". Immunity 11:123 (1 page) (1999).

Klinman, et al., "Repeated administration of synthetic oligodeoxynucteotides expressing CpG motifs provides tongterm protection against bacterial infection". Infect. Immun. 67:5658–5663 (1999).

Klinman, et al., "Activation of the innate immune system by CpG oligodeoxynucleotides: immunoprotective activity and safety". Springer Semin. Immunopathol. 22:173–183 (2000).

Kou, et al., "Analysis and Regulation of interferon–gamma production by peripheral blood lymphocytes from patients with bronchial asthma". Arerugi 43(3):483–491 (1994), abstract only.

Krieg, et al., "CpG motifs in bacterial DNA and their immune effect". Annu. Rev. Immunol. 20:709–760 (2002).

Kreig, et al., "Brief Communication: Oligodeoxynucleotide Modifications Determine the Magnitude of B–Cell Stimulation by CpG Motifs". Antisense & Nucleic Acid Drug Development 6:133–139 (1996).

Krieg, et al., "Phosphorothioate oligodeoxynucleotides: antisense or anti–protein?". Antisense Res. Dev. 5:241 (1 page) (1995).

Krieg, et al., "Uptake of oligodeoxyribonucleotides by lymphoid cells is heterogeneous and inducible". Antisense Res. Dev. 1(2):161–171 (1991).

Krieg, et al., "Leukocyte stimulation by oligodeoxynucleotides". Applied Antisense Oligonucleotide Tech. (BOOK):431–448 (1998).

Krieg, et al., "Causing a Commotion in the Blood: Immunotherapy Progresses from Bacteria to Bacterial DNA". Immunology Today 21(10):521–526 (2000).

Krieg, et al., "CpG DNA: A pathogenic factor in systemic lupus erythematosus?". J. Clin. Immunol. 15(6):284–292 (1995).

Krieg, et al., "CpG DNA induces sustained IL–12 expression in vivo and resistance to Listeria monocytogenes challenge". J. Immunol. 161:2428–2434 (1998).

Krieg, et al., "A role for endogenous retroviral sequences in the regulation of lymphocyte activation". J. Immunol. 143(8):2448–2451 (1989).

Krieg, "An inate immune defense mechanism based on the recognition of CpG motifs in microbial DNA". J. Lab. Clin. Med. 128(2):128–133 (Abstract) (1996).

Krieg, et al., "Modification of antisense phosphodiester oligodeoxynucleotides by a 5'cholesteryl moiety increases cellular association and improves efficacy". Proc. Natl. Acad. Sci. USA 90:1048–1052 (1993).

Krieg, et al., "The role of CpG dinucleotides in DNA vaccines". Trends in Microbiol. 6:23–27 (1998).

Krieger, et al., "Structures and Functions of Multiligand Lipoprotein Receptors: Macrophage Scavenger Receptors and LDL Receptor–Related Protein (LRP)". Annu. Rev. Biochem 63:601–637 (1994).

Krug, et al., "Identification of CpG Oligonucleotide Sequences with High Induction of IFN–α/β in Plasmacytoid Dendritic Cells". Eur. J. Immunol. 31:2154–2163 (2001).

Krug, et al., "Toll–like Receptor Expression Reveals CpG DNA as a Unique Microbial Stimulus for Plasmacytoid Dendritic Cells Which Synergizes With CD40 Ligand to Induce High Amounts of IL–12". Eur. J. Immunol. 31:3026–3037 (2001).

Kuchan, et al., "Nucleotides in Infant Nutrition: Effects of Immune Function". Pediatr. Adolesc. Med. Basel. Karger 8:80–94 (1998).

Kulkarni, et al., "Effect of Dietary Nucleotides on Response to Bacterial Infection". J. Parenter. Enteral. Nutr. 10(2):169–171 Abstract (1986).

Kuramoto, et al., "Oligonucleotide sequences required for natural killer cell activation". Jpn. J. Cancer Res. 83:1128–1131 (1992).

Lagrange, et al., "Immune Responses Directed Against Infectious and Parasitic Agents". Immunology (BOOK—ISBN:0471017604)(Chapter of Book; Ed—Jean–Francois Bach): (1978).

Lang, et al., "Guanosine–rich oligodeoxynucleotides induce proliferation of macrophage progenitors in cultures of murine bone marrow cells". Eur. J. Immunol. 29:3496–3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357–370 (Oct. 1998).

Ledergerber, et al., "Clinical Progression and Virological Failure on Highly Active Antiretroviral Therapy in HIV–1 Patients: a Prospective Cohort Study". The Lancet 353:863–868 (1999).

Lederman, et al., "Polydeooxyguanine Motifs in a 12–mer Phosphorothioate Oligodeooxynucleotide Augment Binding to the v3 Loop of the HIV–1 gp120 and Potency of HIV–1 Inhibition Independently of G–Tetrad Formation". Antisense & Nucleic Acid Drug Development 6:281–289 (1996).

Lee, et al., "An Oligonucleotide Blocks Interferon–γ Signal Transduction". Transplantation 62(9):1297–1301 (1996).

Leibson, et al., "Role of γ–interferon in antibody–producing responses". Nature 309:799–801 (1984).

Leonard, et al., "Conformation of guanine 8–oxoadenine base pairs in the crystal structure of d(CGCGCAATT(O8A)GCG)". Biochemistry 31(36):8415–8420 (1992).

Li, et al., "Long–Lasting Recovery in CDR T–Cell Function and Viral –Load Reduction After Highly Active Antiretroviral Therapy in Advanced HIV–1 Disease". The Lancet 351:1682–1686 (1998).

Lipford, et al., "CpG–containing synthetic oligonucleotides promote B and cytotoxic T cell responses to protein antigen: a new class of vaccine adjuvants". Eur. J. Immunol. 27(9):2340–2344 (1997).

Lipford, et al., "Immunostimulatory DNA: sequence–dependent production of potentially harmful or useful cytokines". Eur. J. Immunol. 27(12):3420–3426 (1997).

Macaya, et al., "Thrombin–binding DNA aptamer forms a unimolecular quadruplex structure in solution". Proc. Natl. Acad. Sci. USA 90:3745–3749 (Apr. 1993).

Macfarlane, et al., "Antagonism of immunostimulatory CpG–oligodeoxynucleotides by quinacrine, chloroquine, and structurally related compounds". J. Immunol. 160(3):1122–1131 (1998).

Maddon, "The Isolation and Nucleotide Sequence of a cDNA Encoding the T Cell Surface Protein T4: A New Member of the Immunoglobulin Gene Family". Cell 42(1):93–104 (1985).

Maltese, et al., "Sequence context of antisense RelA/NF–kB phohphorothioates determines specificity". Nucleic Acids Research 23(7):1146–1151 (1995).

Manzel, et al., "Lack of Immune Stimulation by Immobilized CpG–oligonucletide". Antisense & Nucleic Acid Drug Development 9(5):459–464 (1999).

Mastrangelo, et al., "Gene therapy for human cancer: an essay for clinicians". Seminars Oncology 23(1):4–21 (1996).

Matson, et al., "Nonspecific suppression of [3H]thymidine incorporation by control oligonucleotides". Antisense Res. Dev. 2(4):325–330 (1992).

McCluskie, et al., "Route and Method of DNA Vaccine Influence Immune Responses in Mice and Non–Human Primates". Molecular Med. 5(5):287–300 (1999).

McIntyre, et al., "A sense phosphorothioate oligonucleotide directed to the initiation codon of transcription factor NF–kappa B p65 causes sequence–specific immune stimulation". Antisense Res. Dev. 3(4):309–322 (1993).

McKenzie, "Nucleic Acid Vaccines". Immunologic Res. 24(3):225–244 (2001).

Merad, et al., "In vivo Manipulation of Dendritic Cells to Induce Therapeutic Immunity". Blood 99(5):1676–1682 (2002).

Messina, et al., "Stimulation of in vitro murine lymphocyte proliferation by bacterial DNA". Cell Immunol. 147(6):1759–1764 (1991).

Messina, et al., "The influence of DNA structure on the in vitro stimulation of murine lymphocytes by natural and synthetic polynucleotide antigens". J. Immunol. 147:148–157 (1993).

Mojcik, et al., "Administration of a phosphorothioate oligonucleotide antisense murine endogeneous retroviral MCF env causes immune effect in vivo in a sequence–specific manner". Clin. Immunol. Immunopathol. 67(2):130–136 (1993).

Moss & Ledman, "Immunication of the Immunocompromised Host". Clinical Focus on Primary Immune Deficiencies (1(1):1–3 (1998).

Mottram, et al., "A novel CDC2–related protein kinase from leishmania mexicana, LmmCRK1, is post–translationally regulated during the life cycle". J. Biol. Chem. 268(28):21044–21052 (1993).

Nyce, et al., "DNA antisense therapy for asthma in an animal model". Nature 385:721–725 (1997).

Ogg, et al., "Quantitation of HIV–1–Specific Cytotoxic T–Lymphocytes and Plasma Load of Viral RNA". Science 279:2103–2106 (1998).

Okada, et al., "Bone Marrow–Derived Dendritic Cells Pulsed With a Tumor–Specific Peptide Elicit Effective Anti-Tumor Immunity Against Intracranial Neoplasms". Int. J. Cancer 78:196–201 (1998).

Palucka, et al., "Dendritic Cells as the Terminal Stage of Monocyte Differentiation". J. Immunol. 160:4587–4595 (1999).

Papasavvas, et al., "Enhancement of Human Immunodeficiency Virus Type I–Specific CD4 and CD8 T Cell Responses in Chronically Infected Persons after Temporary Treatement Interruption". J. Infect. Diseases 182:766–775 (200).

Pialoux, et al., "A Randomized Trial of Three Maintenance Regimens Given After Three Months of Induction Therapy with Zidovudine, Lamivudine, and Indinavie in Previously Untreated HIV–1–Infected Patients". The New England Journal of Medicine 339(18):1269–1276 (1998).

Piscitelli, "Immune–Based Therapies for Treatment of HIV Infection". The Annals of Pharmacotherapy 30:62–76 (1996).

Pisetsky, et al., "Immunological Properties of Bacterial DNA". Ann. NY Acad. Sci. 772:152–163 (1995).

Pisetsky, "Immunological consequences of nucleic acid therapy". Antisense Res. Dev. 5:219–225 (1995).

Pisetsky, "The immunological properties of DNA". J. Immunol. 156:421–423 (1996).

Pisetsky, et al., "Stimulation of murine lymphocyte proliferation by a phosphorothioate oligonucleotide with antisense activity for hepes simplex virus". Life Science 54:101–107 (1994), abstract only.

Pisetsky, "Stimulation of in vitro proliferation of murine lymphocytes by synthetic oligodeoxynucleotides". Molecular Biol. Reports 18:217–221 (1993).

Plenat, "Animal models of antisense oligonucleotides: lessons for use in humans". J. Mol. Med. Today 2(6):250–257 (1996).

Prasad, et al., "Oligonucleotides Tethered to a Short Polyguanylic Acid Stretch are Targeted to Macrophages: Enhanced Antiviral Activity of a Vesicular Stomatitis Virus–Specific Antisense Oligonucleotide". Antimicrobial Agents and Chemotherapy 43(11):2689–2696 (Nov. 1999).

Quddus, et al., "Treating activated CD4+ T cells with either of two distinct DNA methyltransferase inhibitors, 5–azacytidine or procaniamide, is sufficient to cause a lupus–like disease in syngeneic mice". J. Clin. Invest. 92(1):38–53 (1993).

Ramanathan, et al., "Characterization of the Oligodeoxynucleotide–mediated Inhibition of Interferon–γ–induced Major Histocompatibility Complex Class I and Intercellular Adhesion Molecule–1". The Journal of Biological Chemistry 269(40):24564–24574 (Oct. 1994).

Ramanathan, et al., "Inhibition of Interferon–γ–Induced Major Histocompatibility Complex Class I Expression by Certain Oligodeoxynucleotides". Transplantation 57(4):612–615 (Feb. 1994).

Raz, "Deviation of the Allergic IgE to an IgG Response by Gene Immunotherapy". Int. Rev. Immunol. 18(3):271–289 (1999).

Raz, et al., "Preferential Induction of a Th1 Immune Response and Inhibition of Specific IgE Antibody Formation by Plasmid DNA Immunization". Proc. Natl. Acad. Sci. USA 93:5141–5145 (1996).

Raz, et al., "Intradermal gene immunization: the possible role of DNA uptake in the induction of cellular immunity to viruses". Proc. Natl. Acad. Sci. USA 91:9519–9523 (1994).

Ricci, et al., "T cells, cytokines, IgE and allergic airways inflammation". J. Invest. Allergol Clin. Immunol. 4(5):214–220 (1994).

Rojanasakul, "Antisense oligonucleotide therapeutics: drug delivery and targeting". Drug Delivery Reviews 18:115–131 (1996).

Roman, et al., "Immunostimulatory DNA sequences function as T helper–1–promoting aduvants". Nature Med. 3(8):849–854 (1997).

Rosenberg, et al., "Immune Control of HIV–1 After Early Treatment of Acute Infection". Nature 407:523–526 (2000).

Rosenberg, et al., "Vigorous HIV–1–Specific CD4+ T–Cell Responses Associated with Control of Viremia". Science 278:1447–1450 (1997).

Ruiz, et al., "Structured Treatment Interruption in Chronically HIV–1 Infected Patients After Long–Term Viral Suppression". AIDS 14:397–403 (2000).

Santini, et al., "Type I Interferon as a Powerful Adjuvant for Monocyte–derived Dendritic Cell Development and Activity In Vitro and in Hu–PBL–SCID Mice". J. Exp. Med. 191:1777–1788 (2000).

Sato, et al., "Immunostimulatory DNA sequences necessary for effective intradermal gene immunization". Science 273:352–354 (1996).

Schnell, et al., "Identification and characterization of a *Saccharomyces cerevisiae* gene (PAR 1) conferring resistance to iron chelators". Eur. J. Biochem. 200:487–493 (1991).

Schoofs, "Small Steps—A Limited Experiment Opens New Approach in Fight Against HIV". Wall Street Journal (Sep. 28, 2000).

Schubbert, et al., "Ingested Foreign (phage M13) DNA Survives Transiently in the Gastrointestinal Tract and Enters the Bloodstream of Mice". Mol. Gen. Genet. 242:495–504 (1994).

Schwartz, et al., "Endotoxin responsiveness and grain dust-induced inflammation in the lower respiratory tract". Am. J. Physiol. 267(5):609–617 (1994).

Schwartz, et al., "The role of endotoxin in grain dust–induced lung disease". Am. J. Respir. Crit. Care Med. 152(2):603–608 (1995).

Schwartz, et al., "CpG motifs in bacterial DNA cause inflammation in the lower respiratory tract". J. Clin. Invest. 100(1):68–73 (1997).

Sedegah, et al., "Intertukin 12 induction of interferon g–dependent protection against malaria". Proc. Natl. Acad. Sci. USA 91:10700–10792 (1994).

Sethi, et al., "Postexposure prophytaxis against prion disease with a stimulator of innate immunity". Lancet 360:229–230 (2002).

Shafer, et al., "Highly Active Antiretroviral Therapy (HAART) for the Treatment of Infection With Human Immunodeficiency Virus Type 1". Biomed. & Pharmachther. 53:73–86 (1999).

Shirakawa, et al., "The inverse association between tuberculin responses and atopic disorder". Science 275(5296):77–79 (1997).

Sidman, et al., "γ–Interferon is one of several direct B cell–maturing lymphokines". Nature 309:801–804 (1984).

Sparwasser, et al., "Macrophages sense pathogens via DNA motifs: induction of tumor necrosis factor–alpha–mediated shock". Eur. J. Immunol. 27(7):1671–1679 (1997).

Sparwasser, et al., "Bacterial DNA and immunostimulatory CpG oligonuceotides trigger maturation and activation of murine dendritic cells". Eur. J. Immunol. 28:2045–2054 (1998).

Spiegelberg, et al., "Recognition of T Cell Epitopes and Lymphokine Secretion by Rye Grass Allergen Lolium perenne I–Specific Human T Cell Clones". J. of Immunology 152:4706–4711 (1994).

Stacey, et al., "Immunostimulatory DNA as an adjuvant in vaccination against Leishmania major". Infect. Immun. 67:3719–3726 (1999).

Stein, et al., "Oligodeoxynucleotides as inhibitors of gene expression: a review". Cancer Res. 48:2659–2668 (1998).

Stull, et al., "Antigene, ribozyme, and aptamer nucleic acid drugs: progress and prospects". Pharm. Res. 12(4):465–483 (1995).

Su, et al., "Vaccination against Chlamydial Genital Tract Infection after Immunization with Dendritic Cells Pulsed Ex Vivo with Nonviable Chlamydiae". J. Exp. Med. 188:809–818 (1998).

Subramanian, et al., "Theoretical considerations on the 'spine of hydration' in the minor groove of d(CGCGAAT-TCGCG) d(CGGCTTAAGCGC): Monte Carlo computer simulation". Proc. Natl. Acad. Sci. USA 85:1836–1840 (1988).

Syme, et al., "Generation of Dendritic Cells ex vivo: Differences in Steady State versus Mobilized Blood from Patients with Breast Cancer, with Lymphoma, and from Normal Donors". J. Hematother. Stem Cell Res. 10:621–630 (2001).

Tanaka, et al., "An antisense oligonucleotide complementary to a sequence in I gamma 2b increases gamma 2b germhine transcripts, stimulates B cell DNA synthesis and inhibits immunoglobulin secretion". J. Exp. Med. 175:597–607 (1992).

Tarte, et al., "Extensive characterization of dendritic cells generated in serum–free conditions: regulation of soluble antigen uptake, apoptotic tumor cell phagocytosis, chemotaxis and T cell activation during maturation in vitro". Leukemia 14:2182–2192 (2000).

Thorne, "Experimental grain dust atmospheres generated by wet and dry aerosolization techniques". Am. J. Ind. Med. 25(1):109–112 (1994).

Tighe, et al., "Conjunction of Protein to Immunostimulatory DNA results in a Rapid Long–Lasting and Potent Induction of Cell–Mediated and Humoral Immunity". Eur. J. Immunol. 30:1939–1947 (2000).

Tokunaga, et al., "A synthetic single–stranded DNA, poly(dG, dC), induces interferon–$\alpha/\beta$ and –$\gamma$, augments natural killer activity and suppresses tumor growth". Jpn. J. Cancer Res. 79:682–686 (1988).

Tokunaga, et al., "Synthetic oligonucleotides with particular base sequences from the cDNA encoding proteins of *Mycobacterium bovis* BCG induce interferons and activate natural killer cells". Microbiol. Immunol. 36(1):55–66 (1992).

Uhlmann, et al., "Antisense oligonucleotides: a new therapeutic principle". Chem. Rev. 90:543–584 (1990).

Verdijk, et al., "Polyriboinosinic Polyribocytidylic Acid (Poly(I:C)) Induces Stable Maturation of Functionally Active Human Dendritic Cells". J. Immunol. 163:57–61 (1999).

Verma, et al., "Gene therapy—promises, problems and prospects". Nature 389:239–242 (Sep. 1997).

Verthelyi, et al., "Human Peripheral Blood Cells Differentially Recognize and Respond to Two Distinct CpG Motifs". J. Immunol. 166:2372–2377 (2001).

Verthelyi, et al., "CpG Oligodeoxynucleotides as Vaccine Adjuvants in Primates". J. Immunol. 168:1659–1663 (2002).

Vil'ner, "Effect of Amphotericin B on the interferonogenic activity of poly(G) poly (C) and poly(G,I).poly(C) in mice and their resistance to infection by the tick–borne encephalitis virus". Antibiotiki 27(11):827–830 (Nov. 1982), abstract.

Vil'ner, et al., "Effect of virazole on the antiviral activity of poly(G) X poly© and other polyribonucleotide interferongens". Antibiotiki 29(6):450–453 (1984), abstract.

Vil'ner, et al., "Evaluation of the size of the continuous poly(G) site necessary for the biological activity of the poly(G).poly(C) complex". Vopr Virusol 30(3):337–340 (1985), abstract.

Vil'ner, "Effect of the size of the continuous poly(G) site in poly(G,A).poly(C) complexes on their interferon–inducing activity and their capacity to stimulate the development of the immunity". Vopr Virusol 31(6):697–700 (1986), abstract.

Vil'ner, et al., "Dependence of the antiviral activity of the poly(G).poly(C) complex on the size of the continuous poly(C) segments". Vopr Virusol 33(3):331–335 (1988), abstract.

Wagner, "Bacterial CpG DNA Activates Immune Cells to Signal Infectious Danger". Adv. Immunol. 73:329–368 (1999).

Wagner, "Gene inhibition using antisense oligodeoxynucleotides". Nature 372:333–335 (1994).

Walker, et al., "Activated T Cells and Cytokines in Bronchoalveolar Lavages from Patients with Various Lung Diseases Associated with Eosinophilia". Am. J. Respir. Crit. Care Med. 150: 1038–1048 (1994).

Walker, et al., "Iminunostimulatory oligodeoxynucleotides promote protective immunity and provide systemic therapy for leishmaniasis via IL–12– and IFN–g–dependent mechanisms". Proc. Natl. Acad. Sci. USA 96:6970–6975 (1999).

Wallace, et al., "Oligonucleotide probes for the screening of recombinant DNA libraries". Methods Enzymol. 152:432–442 (1987).

Weiner, "The immunobiology and clinical potential of immunostimulatory CpG oligodeoxynucleotides". Leukocyte Bio. 68:455–463 (2000).

Weiner, et al., "Immunostimulatory oligodeoxynucleotides containing the CpG motif are effective as immune adjuvants in tumor antigen immunization". Proc. Natl. Acad. Sci. USA 94:10833–10837 (1997).

Weiss, "Upping the antisense ante: scientists bet on profits from reverse genetics". Science 139:108–109 (1991).

Whalen, et al., "DNA–Mediated Immunization to the Helatitis B Surface Antigen: Activation and Entrainment of the Immune Response". Ann. NY Acad. Sci. 772:64–76 (1995).

Whalen, "DNA vaccines for emerging infection diseases: what if?". Emerg. Infect. Dis. 2(3):168–175 (1996).

Wloch, et al., "The influence of DNA sequence on the immunostimulatory properties of plasmid DNA vectors". Hum. Gene Ther. 9(10):1439–1447 (Jul. 1998).

Woolridge, et al., "Immunostimulatory oligodeoxynucleotides containing CpG motifs enhance the efficacy of monoclonal antibody therapy of lymphoma". Blood 89:2994–2998 (1997).

Wu, et al., "Receptor–mediated gene delivery and expression in vivo". J. Biol. Chem. 263:14621–14624 (1988).

Wu–Pong, "Oligonucleotides: opportunities for drug therapy and research". Pharmaceutical Tech. 18:102–114 (1994).

Wyatt, et al., "Combinatorially selected guanosine–quartet structure is a potent inhibitor of human immunodeficiency virus envelope–mediated cell fusion". Proc. Natl. Acad. Sci. USA 91:1356–1360 (Feb. 1994).

Yamamoto, et al., "Ability of oligonucleotides with certain palindromes to induce interferon production and augment natural killer cell activity is associated with their base length". Antisense Res. Dev. 4:119–123 (1994).

Yamamoto, "Unique palindromic sequences in synthetic oligonucleotides are required to induce inf and augment INF–mediated natural killer activity". J. Immunol. 148(12):4072–4076 (1992).

Yamamoto, et al., "In vitro augmentation of natural killer cell activity and production of interferon–alpha/beta and –gamma with deoxyribonucleic acid fraction from *Mycobacterium bovis* BCG". Jpn. J. Cancer Res. 79:866–873 (1988).

Yamamoto, et al., "Synthetic oligonucleotides with certain palindromes stimulate interferon production of human peripheral blood lymphocytes in vitro". Jpn. J. Cancer Res. 85:775–779 (1994).

Yamamoto, et al., "Mode of action of oligonucleotide fraction extracted from *Mycobacterium bovis* BeG". Kekkaku 69(9):29–32 (1994).

Yamamoto, et al., "DNA from bacteria, but not vetebrates, induces interferons, activates natural killer cells, and inhibits tumor growth". Microbiol. Immunol. 36(9):983–997 (1992).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831–836 (1994).

Yaswen, et al., "Effects of Sequence of Thioated Oligonucleotides on Cultured Human Mammary Epithelial Cells". Antisense Research and Development 3:67–77 (1993).

Yew, et al., "Contribution of Plasmid DNA to Inflammation in the Lung After Administration of Cationic Lipid: pDNA Complexes". Hum. Gene Ther. 10(2):223–234 (1999).

Yi, et al., "IFN–γ promotes IL–6 and 1gM secretion in response to CpG motifs in bacterial DNA and oligodeoxynucleotides". J. Immunol. 156:558–564 (1996).

Zelphati, et al., "Inhibition of HIV–1 Replication in Cultured Cells with Antisense Oligonucleotides Encapsulated in Immunoliposomes". Antisense Res. Dev. 3:323 (1993).

Zhang, et al., "Antigen– and Isotype–Specific Immune Responses to a Recombinant Antigen–Allergen Chimeric (RAAC) Protein". J. Immunol. 151:791–799 (1993).

Zhao, et al., "Comparison of cellular binding and uptake of antisense phosphodiester, phosphorothioate, and mixed phosphorothioate and methylphosphonate oligonucleotides". Antisense Res. Dev. 3(1):53–66 (1993).

Zhao, et al., "Stage–specific oligonucleotide uptake in murine bone marrow B–Cell precursors". Blood 84(11):3660–3666 (1994).

Zheng, et al., "Contribution of Vascular Endothelial Growth Factor in the Neovascularization Process During the Pathogenesis of Herpetic Stromal Keratitis". J. Vriol. 75(20):9828–9835 (2001).

Zhu, et al., "Macaque blood–derived antigen–presenting cells elicit SIV–specific immune responses". J. Med. Primatol 29:182–192 (2000).

Zimmermann, et al., "CpG oligodeoxynucleotides trigger protective and curative Th1 responses in lethal murine leishmaniasis". J. Immunol. 160:3627–3630 (1998).

* cited by examiner

Fig. 1

A "D" ODNs require an unmethylated CpG

| | | | | | | | | | | | | | | | | | | | | |
|---|---|---|---|---|---|---|---|---|---|---|---|---|---|---|---|---|---|---|---|---|
| 1 | G | G | T | G | C | A | T | C | G | A | T | G | C | A | G | G | G | G | G | G |
| 2 | - | - | - | - | - | - | - | Ⓖ | Ⓒ | - | - | - | - | - | - | - | - | - | - | - |
| 3 | - | - | - | - | - | - | - | Ⓒ | G | - | - | - | - | - | - | - | - | - | - | - |
| 4 | - | - | - | - | - | - | - | C | Ⓐ | - | - | - | - | - | - | - | - | - | - | - |
| 5 | - | - | - | - | - | - | - | Ⓐ | Ⓐ | - | - | - | - | - | - | - | - | - | - | - |
| 6 | - | - | - | - | - | - | - | Ⓣ | Ⓒ | - | - | - | - | - | - | - | - | - | - | - |
| 7 | G | G | T | G | C | A | C | C | G | G | T | G | C | A | G | G | G | G | G | G |
| 8 | - | - | - | - | - | - | - | Ⓣ | G | - | - | - | - | - | - | - | - | - | - | - |

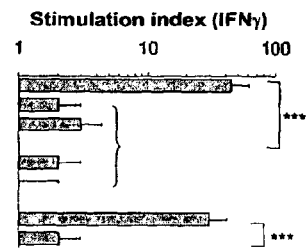

B "D" ODNs require a phosphodiester backbone.

| | | | | | | | | | | | | | | | | | | | | |
|---|---|---|---|---|---|---|---|---|---|---|---|---|---|---|---|---|---|---|---|---|
| 1 | G | G | T | G | C | A | T | C | G | A | T | G | C | A | G | G | G | G | G | G |
| 2 | - | - | - | - | - | - | - | : | : | - | - | - | - | - | - | - | - | - | - | - |
| 3 | - | - | - | - | - | - | - | : | : | - | - | - | - | - | - | - | - | - | - | - |
| 4 | - | - | - | - | - | - | - | : | : | - | - | - | - | - | - | - | - | - | - | - |
| 5 | - | - | - | - | - | - | - | : | : | - | - | - | - | - | - | - | - | - | - | - |

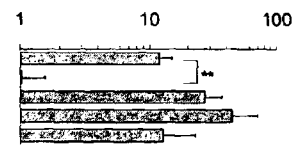

C Optimal "D" motif: pallindromic Pu Py CG Pu Py

| | | | | | | | | | | | | | | | | | | | | |
|---|---|---|---|---|---|---|---|---|---|---|---|---|---|---|---|---|---|---|---|---|
| 1 | G | G | T | G | C | A | T | C | G | A | T | G | C | A | G | G | G | G | G | G |
| 2 | - | - | - | - | - | A | C | : | : | G | T | - | - | - | - | - | - | - | - | - |
| 3 | - | - | - | - | T | G | T | : | : | A | T | - | - | - | - | - | - | - | - | - |
| 4 | - | - | - | - | C | A | T | : | : | A | C | - | - | - | - | - | - | - | - | - |
| 5 | - | - | - | - | - | A | C | : | : | A | T | - | - | - | - | - | - | - | - | - |
| 6 | - | - | - | - | - | A | Ⓐ | : | : | Ⓣ | T | - | - | - | - | - | - | - | - | - |
| 7 | - | - | - | - | - | A | T | : | : | Ⓣ | T | - | - | - | - | - | - | - | - | - |
| 8 | - | - | - | - | - | A | T | : | : | Ⓣ | Ⓐ | - | - | - | - | - | - | - | - | - |
| 9 | - | - | - | - | - | A | T | : | : | A | Ⓐ | - | - | - | - | - | - | - | - | - |
| 10 | - | - | - | - | - | Ⓣ | T | : | : | A | T | - | - | - | - | - | - | - | - | - |
| 11 | - | - | - | - | - | A | Ⓐ | : | : | G | Ⓖ | - | - | - | - | - | - | - | - | - |
| 12 | - | - | - | - | - | Ⓒ | T | : | : | A | Ⓖ | - | - | - | - | - | - | - | - | - |
| 13 | - | - | - | - | - | Ⓖ | C | : | : | Ⓣ | T | - | - | - | - | - | - | - | - | - |

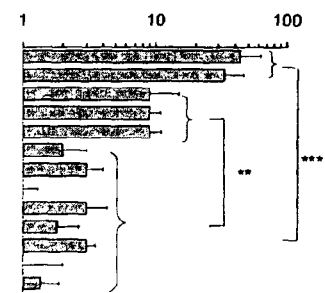

D Minimum size of immunostimulatory D ODN

| | | | | | | | | | | | | | | | | | | | | | |
|---|---|---|---|---|---|---|---|---|---|---|---|---|---|---|---|---|---|---|---|---|---|
| 1 | (22) | G | G | G | G | T | G | C | A | T | C | G | A | T | G | C | A | G | G | G | G | G | G |
| 2 | (20) | - | - | - | - | - | - | - | - | - | : | : | - | - | - | - | - | - | - | - | - | - | - |
| 3 | (18) | | - | - | - | - | - | - | - | - | : | : | - | - | - | - | - | - | - | - | - | | |
| 4 | (16) | | | - | - | G | - | G | - | - | : | : | - | - | - | G | G | - | - | | | | |
| 5 | (13) | | | | - | - | G | - | - | : | : | - | - | A | - | - | - | | | | | | |

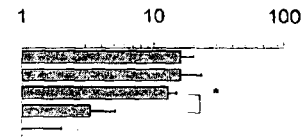

E "D" ODN require a pallindromic far flanking region

| | | | | | | | | | | | | | | | | | | | | |
|---|---|---|---|---|---|---|---|---|---|---|---|---|---|---|---|---|---|---|---|---|
| 1 | G | G | T | G | C | A | T | C | G | A | T | G | C | A | G | G | G | G | G | G |
| 2 | - | - | - | - | C* | G | T | : | : | A | C* | - | - | - | - | - | - | - | - | - |
| 3 | - | - | - | - | Ⓖ | A | - | : | : | A | T | - | - | - | - | - | - | - | - | - |
| 4 | - | - | - | - | C | - | - | : | : | - | - | Ⓐ | Ⓖ | - | - | - | - | - | - | - |

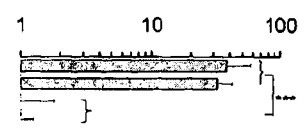

F Poly-G strings improves the activity of "D" ODNs

| | | | | | | | | | | | | | | | | | | | | |
|---|---|---|---|---|---|---|---|---|---|---|---|---|---|---|---|---|---|---|---|---|
| 1 | G | G | T | G | C | A | T | C | G | A | T | G | C | A | G | G | G | G | G | G |
| 2 | A | A | - | - | - | - | - | : | : | - | - | - | - | - | G | G | G | G | G | G |
| 3 | - | - | - | - | - | - | - | : | : | - | - | - | - | - | G | G | G | G | G | G |
| 4 | G | G | - | - | - | - | - | : | : | - | - | - | - | - | G | G | G | G | | |
| 5 | G | G | - | - | - | - | - | : | : | - | - | - | - | - | A | A | A | A | A | A |
| 6 | A | A | - | - | - | - | - | : | : | - | - | - | - | - | A | A | A | A | A | A |
| 7 | G | G | T | G | C | A | C | C | G | G | T | G | C | A | G | G | G | G | G | G |
| 8 | - | - | - | - | - | - | - | : | : | - | - | - | - | - | A | A | A | A | A | A |

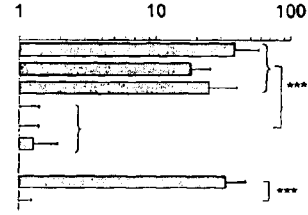

FIG. 4A
Human PBMC
FIG. 4B
Rhesus PBMC
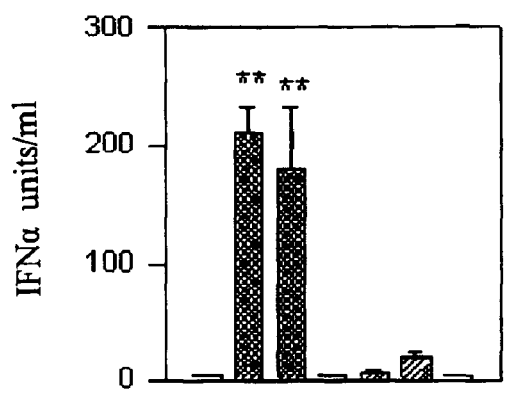
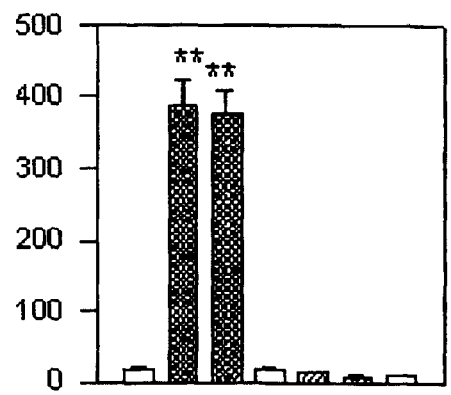
FIG. 4C
FIG. 4D
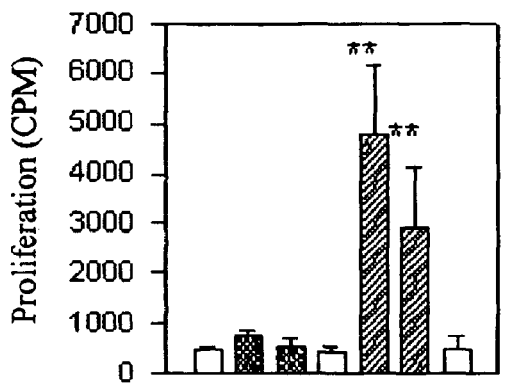
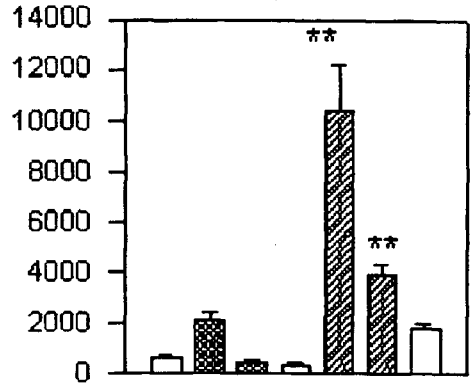
FIG. 4E
FIG. 4F
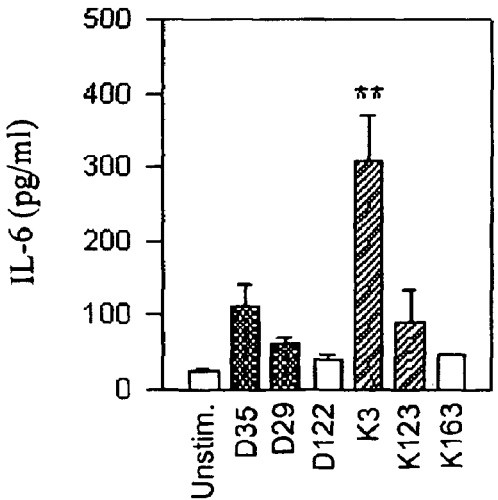
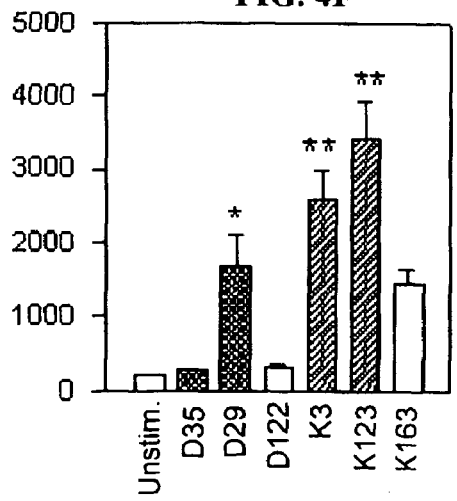

SEQUENCE LISTING

<160> NUMBER OF SEQ ID NOS: 120

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
ggtgcatcga tgcagggggg                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
ggtgcaccgg tgcagggggg                                              20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
atcgactctc gagcgttctc                                              20

<210> SEQ ID NO 4
<211> LENGTH: 11
<212> TYPE: DNA
<213> ORGANISM: Artificial Sequence
<220> FEATURE:
<223> OTHER INFORMATION: Oligonucleotide

<400> SEQUENCE: 4
tcgagcgttc t                                                       11

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
ggtgcacgcg tgcagggggg                                              20

<210> SEQ ID NO 6
<211> LENGTH: 12
<212> TYPE: DNA
<213> ORGANISM: Artificial Sequence
<220> FEATURE:
<223> OTHER INFORMATION: Oligonucleotide

<400> SEQUENCE: 6
tgcaggcttc tc                                                      12

<210> SEQ ID NO 7
<211> LENGTH: 20

```
<212> TYPE: DNA
<213> ORGANISM: Artificial Sequence
<220> FEATURE:
<223> OTHER INFORMATION: Oligonucleotide

<400> SEQUENCE: 7
ggtgcgtcga tgcagggggg                                                     20

<210> SEQ ID NO 8
<211> LENGTH: 19
<212> TYPE: DNA
<213> ORGANISM: Artificial Sequence
<220> FEATURE:
<223> OTHER INFORMATION: Oligonucleotide

<400> SEQUENCE: 8
tcgactctcg agcgttctc                                                      19

<210> SEQ ID NO 9
<211> LENGTH: 16
<212> TYPE: DNA
<213> ORGANISM: Artificial Sequence
<220> FEATURE:
<223> OTHER INFORMATION: Oligonucleotide

<400> SEQUENCE: 9
actctcgagc gttctc                                                         16

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide

<400> SEQUENCE: 10
ctcgagcgtt ctctcgagcg ttct                                                24

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
ggtgcatcga tacagggggg                                                     20

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide

<400> SEQUENCE: 12
tgcatcgatg cagggggg                                                       18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide

<400> SEQUENCE: 13
```

-continued tgcaccggtg caggggg                                     18

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide

<400> SEQUENCE: 14
tgcgtcgacg caggggg                                     18

<210> SEQ ID NO 15
<211> LENGTH: 16
<212> TYPE: DNA
<213> ORGANISM: Artificial Sequence
<220> FEATURE:
<223> OTHER INFORMATION: Oligonucleotide

<400> SEQUENCE: 15
gggcatgcat gggggg                                      16

<210> SEQ ID NO 16
<211> LENGTH: 18
<212> TYPE: DNA
<213> ORGANISM: Artificial Sequence
<220> FEATURE:
<223> OTHER INFORMATION: Oligonucleotide

<400> SEQUENCE: 16
tgcgtcgatg caggggg                                     18

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide

<400> SEQUENCE: 17
tgcgccggcg caggggg                                     18

<210> SEQ ID NO 18
<211> LENGTH: 18
<212> TYPE: DNA
<213> ORGANISM: Artificial Sequence
<220> FEATURE:
<223> OTHER INFORMATION: Oligonucleotide

<400> SEQUENCE: 18
tgcgccgatg caggggg                                     18

<210> SEQ ID NO 19
<211> LENGTH: 18
<212> TYPE: DNA
<213> ORGANISM: Artificial Sequence
<220> FEATURE:
<223> OTHER INFORMATION: Oligonucleotide

<400> SEQUENCE: 19
tgcatcgacg caggggg                                     18

<210> SEQ ID NO 20
<211> LENGTH: 18
<212> TYPE: DNA
<213> ORGANISM: Artificial Sequence

```
-continued

<220> FEATURE:
<223> OTHER INFORMATION: Oligonucleotide

<400> SEQUENCE: 20
tgcgtcggtg caggggggg                                              18

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide

<400> SEQUENCE: 21
ggtgcatcta tgcaggggggg                                            20

<210> SEQ ID NO 22
<211> LENGTH: 12
<212> TYPE: DNA
<213> ORGANISM: Artificial Sequence
<220> FEATURE:
<223> OTHER INFORMATION: Oligonucleotide

<400> SEQUENCE: 22
tcaagtgttc tc                                                     12

<210> SEQ ID NO 23
<211> LENGTH: 12
<212> TYPE: DNA
<213> ORGANISM: Artificial Sequence
<220> FEATURE:
<223> OTHER INFORMATION: Oligonucleotide

<400> SEQUENCE: 23
ttgttcgaac tc                                                     12

<210> SEQ ID NO 24
<211> LENGTH: 12
<212> TYPE: DNA
<213> ORGANISM: Artificial Sequence
<220> FEATURE:
<223> OTHER INFORMATION: Oligonucleotide

<400> SEQUENCE: 24
ttgttcgagc tc                                                     12

<210> SEQ ID NO 25
<211> LENGTH: 12
<212> TYPE: DNA
<213> ORGANISM: Artificial Sequence
<220> FEATURE:
<223> OTHER INFORMATION: Oligonucleotide

<400> SEQUENCE: 25
ttgttcgtac tc                                                     12

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide

<400> SEQUENCE: 26
ggtgtgtcga tgcaggggggg                                            20
```

<210> SEQ ID NO 27
<211> LENGTH: 12
<212> TYPE: DNA
<213> ORGANISM: Artificial Sequence
<220> FEATURE:
<223> OTHER INFORMATION: Oligonucleotide

<400> SEQUENCE: 27
ttgttcgttc tc                                                        12

<210> SEQ ID NO 28
<211> LENGTH: 12
<212> TYPE: DNA
<213> ORGANISM: Artificial Sequence
<220> FEATURE:
<223> OTHER INFORMATION: Oligonucleotide

<400> SEQUENCE: 28
tcgaatgctc tc                                                        12

<210> SEQ ID NO 29
<211> LENGTH: 12
<212> TYPE: DNA
<213> ORGANISM: Artificial Sequence
<220> FEATURE:
<223> OTHER INFORMATION: Oligonucleotide

<400> SEQUENCE: 29
tcggatgagc tc                                                        12

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
ggtgcatcgt tgcagggggg                                                20

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
ggtgcgtcga cgcagggggg                                                20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
ggtcgatcga tgcacggggg                                                20

<210> SEQ ID NO 33
<211> LENGTH: 12
<212> TYPE: DNA
<213> ORGANISM: Artificial Sequence
<220> FEATURE:
<223> OTHER INFORMATION: Oligonucleotide

```
<400> SEQUENCE: 33
tcgtatgtac tc                                                         12

<210> SEQ ID NO 34
<211> LENGTH: 12
<212> TYPE: DNA
<213> ORGANISM: Artificial Sequence
<220> FEATURE:
<223> OTHER INFORMATION: Oligonucleotide

<400> SEQUENCE: 34
acgaggcttc tc                                                         12

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
ggtgcatcga cgcagggggg                                                 20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
ggtgcatcga taggcggggg                                                 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
ggtgcaccga tgcagggggg                                                 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
cctgcatcga tgcagggggg                                                 20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39
ggtatatcga tatagggggg                                                 20

<210> SEQ ID NO 40
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
ggtggatcga tccagggggg                                            20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide

<400> SEQUENCE: 41
ggtgcaacgt tgcagggggg                                            20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
ggtgcatcga tagagggggg                                            20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
ggtgcatcgt agcagggggg                                            20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
ggtggttcga tgcagggggg                                            20

<210> SEQ ID NO 45
<211> LENGTH: 12
<212> TYPE: DNA
<213> ORGANISM: Artificial Sequence
<220> FEATURE:
<223> OTHER INFORMATION: Oligonucleotide

<400> SEQUENCE: 45
gtcggcgctg ac                                                    12

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
```

```
ggtgcaccgg tgcaaaaaaa                                              20

<210> SEQ ID NO 47
<211> LENGTH: 18
<212> TYPE: DNA
<213> ORGANISM: Artificial Sequence
<220> FEATURE:
<223> OTHER INFORMATION: Oligonucleotide

<400> SEQUENCE: 47
ggtgcatcga tagagggg                                                18

<210> SEQ ID NO 48
<211> LENGTH: 11
<212> TYPE: DNA
<213> ORGANISM: Artificial Sequence
<220> FEATURE:
<223> OTHER INFORMATION: Oligonucleotide

<400> SEQUENCE: 48
cgagcgttct c                                                       11

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide

<400> SEQUENCE: 49
ggtgcatcga tgcaaaaaaa                                              20

<210> SEQ ID NO 50
<211> LENGTH: 13
<212> TYPE: DNA
<213> ORGANISM: Artificial Sequence
<220> FEATURE:
<223> OTHER INFORMATION: Oligonucleotide

<400> SEQUENCE: 50
ggggtcgaca ggg                                                     13

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide

<400> SEQUENCE: 51
ggtgcataaa tgcagggggg                                              20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
ggtgcatcaa tgcagggggg                                              20

<210> SEQ ID NO 53
<211> LENGTH: 20
<212> TYPE: DNA
```

```
<213> ORGANISM: Artificial Sequence
<220> FEATURE:
<223> OTHER INFORMATION: Oligonucleotide

<400> SEQUENCE: 53
ggtgcattga tgcagggggg                                               20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide

<400> SEQUENCE: 54
ggtgcatcga tgcagggggg                                               20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide

<400> SEQUENCE: 55
ggtgcatgca tgcaggggggg                                              20

<210> SEQ ID NO 56
<211> LENGTH: 12
<212> TYPE: DNA
<213> ORGANISM: Artificial Sequence
<220> FEATURE:
<223> OTHER INFORMATION: Oligonucleotide

<400> SEQUENCE: 56
gtcagcgccg ac                                                       12

<210> SEQ ID NO 57
<211> LENGTH: 12
<212> TYPE: DNA
<213> ORGANISM: Artificial Sequence
<220> FEATURE:
<223> OTHER INFORMATION: Oligonucleotide

<400> SEQUENCE: 57
gtcggcgccg ac                                                       12

<210> SEQ ID NO 58
<211> LENGTH: 20
<212> TYPE: DNA
<213> ORGANISM: Artificial Sequence
<220> FEATURE:
<223> OTHER INFORMATION: Oligonucleotide

<400> SEQUENCE: 58
ggtgcactgg tgcagggggg                                               20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotide

<400> SEQUENCE: 59
ggtgtatcga tgcaaaaggg                                               20
```

```
<210> SEQ ID NO 60
<211> LENGTH: 20
<212> TYPE: DNA
<213> ORGANISM: Artificial Sequence
<220> FEATURE:
<223> OTHER INFORMATION: Oligonucleotide

<400> SEQUENCE: 60
ggtgccccgt tgcagggggg                                              20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotide

<400> SEQUENCE: 61
ggtgcaacgg ggcagggggg                                              20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotide

<400> SEQUENCE: 62
aatgcatcga tgcaaaaaaa                                              20

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
ggtgcaccgt ggcagggggg                                              20

<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
ggtgcatcga agcagggggg                                              20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide

<400> SEQUENCE: 65
ggtggatcga tgcagggggg                                              20

<210> SEQ ID NO 66
<211> LENGTH: 16
<212> TYPE: DNA
<213> ORGANISM: Artificial Sequence
<220> FEATURE:
```

```
<223> OTHER INFORMATION: Oligonucleotide

<400> SEQUENCE: 66
actcttgagt gttctc                                                   16

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
ggtgcatgta tgcagggggg                                               20

<210> SEQ ID NO 68
<211> LENGTH: 16
<212> TYPE: DNA
<213> ORGANISM: Artificial Sequence
<220> FEATURE:
<223> OTHER INFORMATION: Oligonucleotide

<400> SEQUENCE: 68
gggggatcga tggggg                                                   16

<210> SEQ ID NO 69
<211> LENGTH: 16
<212> TYPE: DNA
<213> ORGANISM: Artificial Sequence
<220> FEATURE:
<223> OTHER INFORMATION: Oligonucleotide

<400> SEQUENCE: 69
gggggaagct tcgggg                                                   16

<210> SEQ ID NO 70
<211> LENGTH: 13
<212> TYPE: DNA
<213> ORGANISM: Artificial Sequence
<220> FEATURE:
<223> OTHER INFORMATION: Oligonucleotide

<400> SEQUENCE: 70
ctcgagcgtt ctc                                                      13

<210> SEQ ID NO 71
<211> LENGTH: 16
<212> TYPE: DNA
<213> ORGANISM: Artificial Sequence
<220> FEATURE:
<223> OTHER INFORMATION: Oligonucleotide

<400> SEQUENCE: 71
actctcgagc gttcta                                                   16

<210> SEQ ID NO 72
<211> LENGTH: 14
<212> TYPE: DNA
<213> ORGANISM: Artificial Sequence
<220> FEATURE:
<223> OTHER INFORMATION: Oligonucleotide

<400> SEQUENCE: 72
tctcgagcgt tctc                                                     14
```

```
<210> SEQ ID NO 73
<211> LENGTH: 16
<212> TYPE: DNA
<213> ORGANISM: Artificial Sequence
<220> FEATURE:
<223> OTHER INFORMATION: Oligonucleotide

<400> SEQUENCE: 73
actctggagc gttctc                                                    16

<210> SEQ ID NO 74
<211> LENGTH: 12
<212> TYPE: DNA
<213> ORGANISM: Artificial Sequence
<220> FEATURE:
<223> OTHER INFORMATION: Oligonucleotide

<400> SEQUENCE: 74
tgcagcgttc tc                                                        12

<210> SEQ ID NO 75
<211> LENGTH: 12
<212> TYPE: DNA
<213> ORGANISM: Artificial Sequence
<220> FEATURE:
<223> OTHER INFORMATION: Oligonucleotide

<400> SEQUENCE: 75
tcgaggcttc tc                                                        12

<210> SEQ ID NO 76
<211> LENGTH: 12
<212> TYPE: DNA
<213> ORGANISM: Artificial Sequence
<220> FEATURE:
<223> OTHER INFORMATION: Oligonucleotide

<400> SEQUENCE: 76
gtcggcgttg ac                                                        12

<210> SEQ ID NO 77
<211> LENGTH: 12
<212> TYPE: DNA
<213> ORGANISM: Artificial Sequence
<220> FEATURE:
<223> OTHER INFORMATION: Oligonucleotide

<400> SEQUENCE: 77
gcgaggcttc tc                                                        12

<210> SEQ ID NO 78
<211> LENGTH: 12
<212> TYPE: DNA
<213> ORGANISM: Artificial Sequence
<220> FEATURE:
<223> OTHER INFORMATION: Oligonucleotide

<400> SEQUENCE: 78
gtcaacgccg ac                                                        12

<210> SEQ ID NO 79
<211> LENGTH: 12
<212> TYPE: DNA
<213> ORGANISM: Artificial Sequence
<220> FEATURE:
<223> OTHER INFORMATION: Oligonucleotide
```

-continued

```
<400> SEQUENCE: 79
tcgagcgttc tc                                                    12

<210> SEQ ID NO 80
<211> LENGTH: 12
<212> TYPE: DNA
<213> ORGANISM: Artificial Sequence
<220> FEATURE:
<223> OTHER INFORMATION: Oligonucleotide

<400> SEQUENCE: 80
acgagggttc tc                                                    12

<210> SEQ ID NO 81
<211> LENGTH: 12
<212> TYPE: DNA
<213> ORGANISM: Artificial Sequence
<220> FEATURE:
<223> OTHER INFORMATION: Oligonucleotide

<400> SEQUENCE: 81
gtcggcgtcg ac                                                    12

<210> SEQ ID NO 82
<211> LENGTH: 12
<212> TYPE: DNA
<213> ORGANISM: Artificial Sequence
<220> FEATURE:
<223> OTHER INFORMATION: Oligonucleotide

<400> SEQUENCE: 82
ccgaggcttc tc                                                    12

<210> SEQ ID NO 83
<211> LENGTH: 14
<212> TYPE: DNA
<213> ORGANISM: Artificial Sequence
<220> FEATURE:
<223> OTHER INFORMATION: oligonucleotide

<400> SEQUENCE: 83
actctttcgt tctc                                                  14

<210> SEQ ID NO 84
<211> LENGTH: 12
<212> TYPE: DNA
<213> ORGANISM: Artificial Sequence
<220> FEATURE:
<223> OTHER INFORMATION: Oligonucleotide

<400> SEQUENCE: 84
gtcgacgttg ac                                                    12

<210> SEQ ID NO 85
<211> LENGTH: 12
<212> TYPE: DNA
<213> ORGANISM: Artificial Sequence
<220> FEATURE:
<223> OTHER INFORMATION: Oligonucleotide

<400> SEQUENCE: 85
tgcagcgagc tc                                                    12

<210> SEQ ID NO 86
<211> LENGTH: 16
```

```
<212> TYPE: DNA
<213> ORGANISM: Artificial Sequence
<220> FEATURE:
<223> OTHER INFORMATION: Oligonucleotide

<400> SEQUENCE: 86
actctcgagg gttctc                                                    16

<210> SEQ ID NO 87
<211> LENGTH: 16
<212> TYPE: DNA
<213> ORGANISM: Artificial Sequence
<220> FEATURE:
<223> OTHER INFORMATION: Oligonucleotide

<400> SEQUENCE: 87
gggggaacgt tgggyg                                                    16

<210> SEQ ID NO 88
<211> LENGTH: 20
<212> TYPE: DNA
<213> ORGANISM: Artificial Sequence
<220> FEATURE:
<223> OTHER INFORMATION: Oligonucleotide

<400> SEQUENCE: 88
actctcgagc gttctcaaaa                                                20

<210> SEQ ID NO 89
<211> LENGTH: 16
<212> TYPE: DNA
<213> ORGANISM: Artificial Sequence
<220> FEATURE:
<223> OTHER INFORMATION: Oligonucleotide

<400> SEQUENCE: 89
catctcgagc gttctc                                                    16

<210> SEQ ID NO 90
<211> LENGTH: 12
<212> TYPE: DNA
<213> ORGANISM: Artificial Sequence
<220> FEATURE:
<223> OTHER INFORMATION: Oligonucleotide

<400> SEQUENCE: 90
gtcgtcgatg ac                                                        12

<210> SEQ ID NO 91
<211> LENGTH: 8
<212> TYPE: DNA
<213> ORGANISM: Artificial Sequence
<220> FEATURE:
<223> OTHER INFORMATION: Oligonucleotide

<400> SEQUENCE: 91 tcgagcgt                                                              8

<210> SEQ ID NO 92
<211> LENGTH: 12
<212> TYPE: DNA
<213> ORGANISM: Artificial Sequence
<220> FEATURE:
<223> OTHER INFORMATION: Oligonucleotide

<400> SEQUENCE: 92
```

-continued tcgttcgttc tc                                               12

<210> SEQ ID NO 93
<211> LENGTH: 12
<212> TYPE: DNA
<213> ORGANISM: Artificial Sequence
<220> FEATURE:
<223> OTHER INFORMATION: Oligonucleotide

<400> SEQUENCE: 93
tcgtttgttc tc                                               12

<210> SEQ ID NO 94
<211> LENGTH: 12
<212> TYPE: DNA
<213> ORGANISM: Artificial Sequence
<220> FEATURE:
<223> OTHER INFORMATION: Oligonucleotide

<400> SEQUENCE: 94
gtcgacgctg ac                                               12

<210> SEQ ID NO 95
<211> LENGTH: 12
<212> TYPE: DNA
<213> ORGANISM: Artificial Sequence
<220> FEATURE:
<223> OTHER INFORMATION: Oligonucleotide

<400> SEQUENCE: 95
tcgatgcttc tc                                               12

<210> SEQ ID NO 96
<211> LENGTH: 12
<212> TYPE: DNA
<213> ORGANISM: Artificial Sequence
<220> FEATURE:
<223> OTHER INFORMATION: Oligonucleotide

<400> SEQUENCE: 96
tcgccgcttc tc                                               12

<210> SEQ ID NO 97
<211> LENGTH: 12
<212> TYPE: DNA
<213> ORGANISM: Artificial Sequence
<220> FEATURE:
<223> OTHER INFORMATION: Oligonucleotide

<400> SEQUENCE: 97
gtcgacgccg ac                                               12

<210> SEQ ID NO 98
<211> LENGTH: 12
<212> TYPE: DNA
<213> ORGANISM: Artificial Sequence
<220> FEATURE:
<223> OTHER INFORMATION: Oligonucleotide

<400> SEQUENCE: 98
gtcatcgatg ca                                               12

<210> SEQ ID NO 99
<211> LENGTH: 14
<212> TYPE: DNA
<213> ORGANISM: Artificial Sequence

```
<220> FEATURE:
<223> OTHER INFORMATION: Oligonucleotide

<400> SEQUENCE: 99
actctttcga tctc                                                          14

<210> SEQ ID NO 100
<211> LENGTH: 12
<212> TYPE: DNA
<213> ORGANISM: Artificial Sequence
<220> FEATURE:
<223> OTHER INFORMATION: Oligonucleotide

<400> SEQUENCE: 100
gtcagcgtcg ac                                                            12

<210> SEQ ID NO 101
<211> LENGTH: 12
<212> TYPE: DNA
<213> ORGANISM: Artificial Sequence
<220> FEATURE:
<223> OTHER INFORMATION: Oligonucleotide

<400> SEQUENCE: 101
gtcaacgtcg ac                                                            12

<210> SEQ ID NO 102
<211> LENGTH: 12
<212> TYPE: DNA
<213> ORGANISM: Artificial Sequence
<220> FEATURE:
<223> OTHER INFORMATION: Oligonucleotide

<400> SEQUENCE: 102
tggagcgttc tc                                                            12

<210> SEQ ID NO 103
<211> LENGTH: 12
<212> TYPE: DNA
<213> ORGANISM: Artificial Sequence
<220> FEATURE:
<223> OTHER INFORMATION: Oligonucleotide

<400> SEQUENCE: 103
tgctgcgttc tc                                                            12

<210> SEQ ID NO 104
<211> LENGTH: 12
<212> TYPE: DNA
<213> ORGANISM: Artificial Sequence
<220> FEATURE:
<223> OTHER INFORMATION: Oligonucleotide

<400> SEQUENCE: 104
ttgagcgtac tc                                                            12

<210> SEQ ID NO 105
<211> LENGTH: 12
<212> TYPE: DNA
<213> ORGANISM: Artificial Sequence
<220> FEATURE:
<223> OTHER INFORMATION: Oligonucleotide

<400> SEQUENCE: 105
tgcttcgagc tc                                                            12
```

-continued

<210> SEQ ID NO 106
<211> LENGTH: 12
<212> TYPE: DNA
<213> ORGANISM: Artificial Sequence
<220> FEATURE:
<223> OTHER INFORMATION: Oligonucleotide

<400> SEQUENCE: 106
tgcaccgttc tc                                                          12

<210> SEQ ID NO 107
<211> LENGTH: 12
<212> TYPE: DNA
<213> ORGANISM: Artificial Sequence
<220> FEATURE:
<223> OTHER INFORMATION: Oligonucleotide

<400> SEQUENCE: 107
gtcaacgctg ac                                                          12

<210> SEQ ID NO 108
<211> LENGTH: 9
<212> TYPE: DNA
<213> ORGANISM: Artificial Sequence
<220> FEATURE:
<223> OTHER INFORMATION: Oligonucleotide

<400> SEQUENCE: 108 tcgagcgtt                                                               9

<210> SEQ ID NO 109
<211> LENGTH: 12
<212> TYPE: DNA
<213> ORGANISM: Artificial Sequence
<220> FEATURE:
<223> OTHER INFORMATION: Oligonucleotide

<400> SEQUENCE: 109
ttgagtgttc tc                                                          12

<210> SEQ ID NO 110
<211> LENGTH: 10
<212> TYPE: DNA
<213> ORGANISM: Artificial Sequence
<220> FEATURE:
<223> OTHER INFORMATION: Oligonucleotide

<400> SEQUENCE: 110
tcgagcgttc                                                             10

<210> SEQ ID NO 111
<211> LENGTH: 12
<212> TYPE: DNA
<213> ORGANISM: Artificial Sequence
<220> FEATURE:
<223> OTHER INFORMATION: Oligonucleotide

<400> SEQUENCE: 111
gtcggcgctg ac                                                          12

<210> SEQ ID NO 112
<211> LENGTH: 7
<212> TYPE: DNA
<213> ORGANISM: Artificial Sequence
<220> FEATURE:
<223> OTHER INFORMATION: Oligonucleotide

```
<400> SEQUENCE: 112 tcgagcg                                                              7

<210> SEQ ID NO 113
<211> LENGTH: 20
<212> TYPE: DNA
<213> ORGANISM: Artificial Sequence
<220> FEATURE:
<223> OTHER INFORMATION: Oligonucleotide

<400> SEQUENCE: 113
atgcactctg caggcttctc                                               20

<210> SEQ ID NO 114
<211> LENGTH: 12
<212> TYPE: DNA
<213> ORGANISM: Artificial Sequence
<220> FEATURE:
<223> OTHER INFORMATION: Oligonucleotide

<400> SEQUENCE: 114
gtcagcgctg ac                                                       12

<210> SEQ ID NO 115
<211> LENGTH: 7
<212> TYPE: DNA
<213> ORGANISM: Artificial Sequence
<220> FEATURE:
<223> OTHER INFORMATION: Oligonucleotide

<400> SEQUENCE: 115 tcgagcg                                                              7

<210> SEQ ID NO 116
<211> LENGTH: 10
<212> TYPE: DNA
<213> ORGANISM: Artificial Sequence
<220> FEATURE:
<223> OTHER INFORMATION: Oligonucleotide

<400> SEQUENCE: 116
tcgagcgttc                                                          10

<210> SEQ ID NO 117
<211> LENGTH: 9
<212> TYPE: DNA
<213> ORGANISM: Artificial Sequence
<220> FEATURE:
<223> OTHER INFORMATION: Oligonucleotide

<400> SEQUENCE: 117 tcgagcgtt                                                            9

<210> SEQ ID NO 118
<211> LENGTH: 12
<212> TYPE: DNA
<213> ORGANISM: Artificial Sequence
<220> FEATURE:
<223> OTHER INFORMATION: Oligonucleotide

<400> SEQUENCE: 118
gtcagcgctg ac                                                       12

<210> SEQ ID NO 119
```

```
-continued

<211> LENGTH: 20
<212> TYPE: DNA
<213> ORGANISM: Artificial Sequence
<220> FEATURE:
<223> OTHER INFORMATION: Oligonucleotide

<400> SEQUENCE: 119
atgcactctg caggcttctc                                              20

<210> SEQ ID NO 120
<211> LENGTH: 12
<212> TYPE: DNA
<213> ORGANISM: Artificial Sequence
<220> FEATURE:
<223> OTHER INFORMATION: Oligonucleotide

<400> SEQUENCE: 120
gtcggcgctg ac                                                      12
```

OLIGODEOXYNUCLEOTIDE AND ITS USE TO INDUCE AN IMMUNE RESPONSE

PRIORITY CLAIM

This is a continuation-in-part of U.S. application Ser. No. 09/958,713 filed on Oct. 11, 2001, which is the United States national phase application under 35 U.S.C. § 371 of PCT Application No. PCT/US00/09839 filed on Apr. 12, 2000, which claims priority to U.S. Provisional Patent Application No. 60/128,898 filed on Apr. 12, 1999, all of which are incorporated herein by reference in their entirety.

STATEMENT OF GOVERNMENT SUPPORT

This invention was supported in part by Military Interdepartmental Purchase Request MM8926. The Government of the United States has certain rights in this invention.

FIELD OF THE DISCLOSURE

The present invention relates to the induction of an immune response, specifically to oligodeoxynucleotides including a CpG motif and their use in inducing an immune response.

BACKGROUND

Cells of the immune system recognize and are activated by conserved pathogen associated molecular patterns (PAMPs) in infectious agents. The unmethylated CpG dimers embedded in bacterial DNA, as well as certain synthetic oligodeoxynucleotides (ODNs) containing unmethylated CpG sequences (termed a CpG motif) that emulated them, are more frequent in the genomes of bacteria and viruses than vertebrates. Recent studies suggest that immune recognition of these motifs may contribute to the host's innate immune response (Klinman et al., Proc. Natl. Acad. Sci. USA 93: 2879, 1996; Yi et al, J. Immun. 157: 5394, 1996; Liang et al., J. Clin. Invest. 98:1119, 1996; Krieg et al., 374 Nature 374: 546, 1995).

In mice, CpG DNA induces proliferation in almost all (>95%) of B cells and increases immunoglobulin (Ig) secretion. This B-cell activation by CpG DNA is T-cell independent and antigen non-specific. In addition to its direct effects on B cells, CpG DNA has also been shown to activate cells of the immune system (see, for example, International Patent Applications WO 95/26204, WO 96/02555, WO 98/11211, WO 98/18810, WO 98/37919, WO 98/40100, WO 98/52581, PCT/US98/047703, and PCT/US99/07335; U.S. Pat. No. 5,663,153).

Although bacterial DNA and certain oligonucleotides can induce a murine immune response, little is known about the immunostimulatory capacity of these materials for the human immune system (Ballas et al., 157 J. Immun. 157: 1840 1996). In addition, differences in the responsiveness of human and murine B cells to certain stimuli render it difficult to extrapolate results obtained from mouse to man.

In view of the above, there exists a need for oligonucleotides that induce an immune response in humans. In addition, there is a need for methods utilizing CpG containing oligonuceotides in the treatment of human diseases.

BRIEF SUMMARY OF SPECIFIC EMBODIMENTS

A substantially pure or isolated oligodeoxynucleotide (ODN) is disclosed herein that is at least about 16 nucleotides in length. The ODNs are referred to herein as D type ODNs, and are distinct from the previously described K type ODNs.

The oligodeoxynucleotide includes a sequence represented by the following formula:

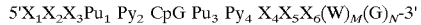

wherein the central CpG motif is unmethylated, Pu is a purine nucleotide, Py is a pyrimidine nucleotide, X and W are any nucleotide, M is any integer from 0 to 10, and N is any integer from 4 to 10. In one embodiment, $X_1X_2X_3$ and $X_4X_5X_6$ are self-complementary. In another embodiment, at least two G's are included at the 5' end of the molecule, such that the oligodeoxynucleotide includes a sequence represented by the formula:

These oligodexoynucleotides are also referred to as "D type" oligodeoxynucleotides. In one embodiment, $Pu_1$ $Py_2$ CpG $Pu_3$ $Py_4$ are phosphodiester bases. In one specific, non-limiting example, $Pu_1$ is an adenine and $Py_2$ is a tyrosine. In another specific, non-limiting example, $Pu_3$ is an adenine and $Py_4$ is a tyrosine.

These oligodeoxynucleotides stimulate cell types of the immune system to mount distinct immune responses. In one embodiment, the oligonucleotide induces production of a cytokine. Specific, non-limiting examples are interferon-gamma (IFN-γ), interferon-alpha (IFN-α), IP-10, or IL-10. In another embodiment, a method is provided for activating a cell of the immune system. These cells include, but are not limited to, dendritic cells, natural killer (NK cells), and monocytes. Thus by employing D type ODN, the immune system can be manipulated to support specific therapeutic goals.

Also disclosed herein is a delivery complex for D type oligodeoxynucleotides and pharmacological composition comprising the D-type oligodeoxynucleotides.

BRIEF DESCRIPTION OF THE FIGURES

FIG. 1 is a set of bar graphs illustrating the response of PBMC to K and D ODN. PBMC from 35 donors were stimulated for 72 h with K or D ODN (3 mM). D19 (GGTGCATCGATGCAGGGGGG, SEQ ID NO: 1) and D29 (GGTGCACCGGTGCAGGGGGG, SEQ ID NO: 2) exemplify the response of PBMC to ODN that selectively induce IFN-γ, whereas K3 (ATCGACTCTCGAG CGTTCTC, SEQ ID NO: 3) and K23 (TCGAGCGTTCT, SEQ ID NO: 4) exemplify ODN that induce IgM and IL-6 secretion and cell proliferation but little IFN-γ. Control ODN have the CG dimer reversed or the C in the CG dimer replaced by a T; therefore, control D (GGTGCACGCGTGCAGGGGGG, SEQ ID NO: 5) and control K (TGCAGGCTTCTC, SEQ ID NO: 6). Bases in bold-face type are phosphorodiester, and those in normal type are phosphorothioate. Cytokine and immunoglobulin (Ig) concentrations in supernatants were determined by ELISA, and cell proliferation was assessed by [$^3$H] thymidine uptake. All assays were done in triplicate. Statistical significance was determined by the nonparametric Mann-Whitney U test.

FIG. 2A is a set of sequences and a bar graph demonstrating that D ODNs require an unmethylated CpG. FIG. 2B is a set of sequences and a bar graph demonstrating that D ODNs require a phosphodiester backbone for optimal stimulation. FIG. 2C is a set of sequences and a bar graph demonstrating that a self complementary $Pu_1Py_2$ CpG $Pu_3Py_4$ increases the stimulation index. FIG. 2D is a set of sequences and a bar graph showing how size of an ODN affects stimulation index. FIG. 2E is a set of sequences and a bar graph demonstrating that increased stimulation is obtained with a self complementary flanking region. FIG. 2F is a set of sequences and a bar graph demonstrating that 3' poly-G sequences can be used to improve activity of D ODNs. The ODN shown here are representative of 120 ODN used to characterize the structural requirements of D ODN. CGs are underlined; immunostimulatory motifs are in bold; extended motifs are in italics; methylated bases have an asterisk; dots indicate identity; and shaded backgrounds identify phosphorodiester-linked bases. Important base changes in the sequence are circled. Data is expressed as stimulation indices, representing the fold increase in cytokine secretion relative to unstimulated cells from the same donor. Bars represent the mean and SE of 20 different experiments. The ODN shown do not induce significant levels of IgM or proliferation. Statistical significance was determined by the non-parametric Mann-Whitney U or nonparametric ANOVA: *, $p<0.05$; , $p<0.01$; *, $p<0.001$.

FIG. 4A–F show the results of a study where PBMC from 8–20 normal human donors (A, C and E) and 20 rhesus macaques were stimulated for 72 hours with a panel of "K", "D" or control ODN (3 μM). IL-6 and IFN-α (A and B) levels in culture supernatants were determined by ELISA while cell proliferation was assessed by [H]³ thymidine uptake (C and D). Note that D ODN induce the secretion of IFNα while K ODN induce cell proliferation and IL-6 production. All assays were performed in triplicate. Statistical significance was determined by ANOVA of log normalized data. * $p<0.05$; ** $p<0.01$.

DETAILED DESCRIPTION OF SEVERAL EMBODIMENTS

I. Abbreviations

A: adenine

Ab: antibody

APC: antigen presenting cell

C: cytosine

APC: antigen presenting cell

Figure 2:
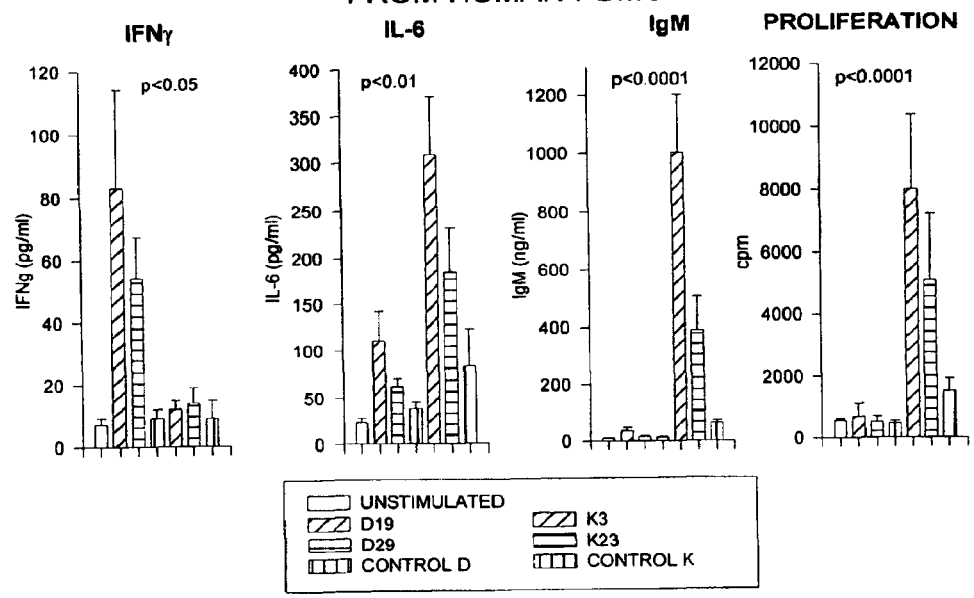
FIG. 2 is several sets of sequences and bar graphs showing the parameters governing D ODN induced immune activation.
Figure 3:
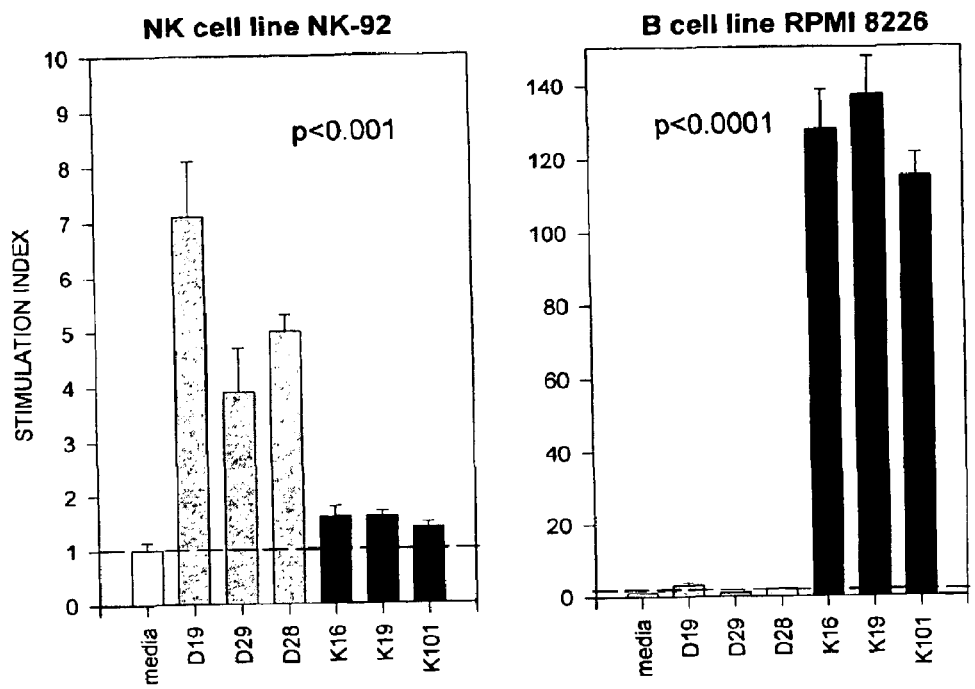
FIG. 3 shows the cell type-dependent response to CpG ODN. Fold increase in IFN-γ production by NK-92cells and IL-6-secreting cell number by RPMI 8226 cells in response to ODN (3 mM for NK cells and 1 mM for B cells). The number of cells secreting IL-6 was determined by ELISPOT, and the secretion of IFN-g was determined at 72 h in culture supernatants by ELISA. Sequences: D19, D29 (see FIG. 1), D28 (GGTGCGTCGATGCAGGGGGG, SEQ ID NO: 7), K16 (TC-GACTCTCGAGCGTTCTC, SEQ ID NO: 8), K19 (ACTCTCGAGCGTTCTC, SEQ ID NO:9), K101 (CTCGAGCGTTCT, SEQ ID NO: 10). Statistical significance determined by non-parametric Mann-Whitney U and non-parametric ANOVA tests.

CpG ODN: an oligodexoynucleotide (either a D or a K type) including a CpG motif.

DC: dendritic cell

FCS: fetal calf serum

G: guanine h: hour

HKLV: heat-killed leishmania vaccine

IFN-α: interferon alpha

IFN-γ: interferon gamma

IL-10: interleukin 10 mm: millimeter mRNA: messenger ribonucleic acid.

ODN: oligodeoxynucleotide

Pu: purine

Py: pyrimidine s.c.: subcutaneaous

T: thymine

μg: microgram

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. The term "comprises" means "includes." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. In case of conflict, the present specification, including explanations of terms, will control. In addition, the materials, methods, and examples are illustrative only and not intended to be limiting.

In order to facilitate review of the various embodiments of the invention, the following explanations of specific terms are provided:

Allergen: A substance that can induce an allergic or asthmatic response in a susceptible subject. The list of allergens is enormous and can include pollens, insect venoms, animal dander dust, fungal spores and drugs (e.g. penicillin). Examples of natural, animal and plant allergens include proteins specific to the following genera: Canine (*Canis familiaris*); *Dermatophagoides* (e.g. *Dermatophagoides farinae*); *Felis* (*Felis domesticus*); *Ambrosia* (*Ambrosia artemiisfolia*); *Lolium* (e.g. *Lolium perenne* or *Lolium multiflorum*); *Cryptomeria* (*Cryptomeria japonica*); *Alternaria* (*Alternaria alternata*); *Alder*; *Alnus* (*Alnus gultinosa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*). The term "allergy" refers to acquired hypersensitivity to a substance (allergen). An "allergic reaction" is the response of an immune system to an allegen in a subject allergic to the allergen. Allergic conditions include eczema, allergic rhinitis or coryza, hay fever, bronchial asthma, urticaria (hives) and food allergies, and other atopic conditions.

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes.

Anti-infectious agent: A substance (such as a chemical compound, protein, antisense oligonucleotide, or other molecule) of use in treating infection of a subject. Anti-infectious agents include, but are not limited to, anti-fungals, anti-virals, and antibiotics.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

Asthma: A disorder of the respiratory system characterized by inflammation, narrowing of the airways and increased reactivity of the airways to inhaled agents. Asthma is frequently, although not exclusively associated with atopic or allergic symptoms.

Autoimmune disorder: A disorder in which the immune system produces an immune response (e.g. a B cell or a T cell response) against an endogenous antigen, with consequent injury to tissues.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D and K type oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cancer: A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

Chemotherapy; chemotherapeutic agents: As used herein, any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

Cytokine: Proteins made by cells that affect the behavior of other cells, such as lymphocytes. In one embodiment, a cytokine is a chemokine, a molecule that affects cellular trafficking.

Dendritic cell (DC): Dendritic cells are the principle antigen presenting cells (APCs) involved in primary immune responses. Their major function is to obtain antigen in tissues, migrate to lymphoid organs and present the antigen in order to activate T cells.

When an appropriate maturational cue is received, DC are signaled to undergo rapid morphological and physiological changes that facilitate the initiation and development of immune responses. Among these are the up-regulation of molecules involved in antigen presentation; production of pro-inflammatory cytokines, including IL-12, key to the generation of Th1 responses; and secretion of chemokines that help to drive differentiation, expansion, and migration of surrounding naive Th cells. Collectively, these up-regulated molecules facilitate the ability of DC to coordinate the activation and effector function of other surrounding lymphocytes that ultimately provide protection for the host. Although the process of DC maturation is commonly associated with events that lead to the generation of adaptive immunity, many stimuli derived from the innate branch of the immune system are also capable of activating DC to initiate this process. In this manner, DC provide a link between the two branches of the immune response, in which their initial activation during the innate response can influence both the nature and magnitude of the ensuing adaptive response. A dendritic cell precursor is a cell that matures into an antigen presenting dendritic cell. In one embodiment, a dendritic cell is a plasmacytoid dendritic cell.

Differentiation: The process by which cells become more specialized to perform biological functions, and differentiation is a property that is totally or partially lost by cells that have undergone malignant transformation. For example, dendritic cell precursors undergo maturation to become APCs.

Epitope: An antigenic determinant. These are particular chemical groups or peptide sequences on a molecule that are antigenic, i.e. that elicit a specific immune response. An antibody binds a particular antigenic epitope.

Functionally Equivalent: Sequence alterations, for example in a D type ODN, that yield the same results as described herein. Such sequence alterations can include, but are not limited to, deletions, base modifications, mutations, labeling, and insertions.

Immune response: A response of a cell of the immune system, such as a B cell, T cell to a stimulus. In one embodiment, the response is specific for a particular antigen (an "antigen-specific response").

Immune system deficiency: A disease or disorder in which the subject's immune system is not functioning in normal capacity or in which it would be useful to boost a subject's immune response. Immune system deficiencies include those diseases or disorders in which the immune system is not functioning at normal capacity, or in which it would be useful to boost the immune system response. In one specific, non-limiting example, a subject with an immune system deficiency has a tumor or cancer (e.g. tumors of the brain, lung (e.g. small cell and non-small cell), ovary, breast, prostate, colon, as well as other carcinomas and sarcomas).

Infectious agent: An agent that can infect a subject, including, but not limited to, viruses, bacteria, and fungi.

Examples of infectious virus include: Retroviridae; Picornaviridae (for example, polio viruses, hepatitis A virus; enteroviruses, human coxsackie viruses, rhinoviruses, echoviruses); Calciviridae (such as strains that cause gastroenteritis); Togaviridae (for example, equine encephalitis viruses, rubella viruses); Flaviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bungaviridae (for example, Hantaan viruses, bunga viruses, phleboviruses and Nairo viruses); Arena viridae (hemorrhagic fever viruses); Reoviridae (e.g., reoviruses, orbivirses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* sps (such as. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelii*.

Examples of infectious fungi include, but are not limited to, *Cryptococcus neoformans, Histoplasma capsulatum, Coccidioides immitis, Blastomyces dermatitidis, Chlamydia trachomatis, Candida albicans*.

Other infectious organisms (such as protists) include: *Plasmodium falciparum* and *Toxoplasma gondii*.

Interferon alpha: At least 23 different variants of IFN-α are known. The individual proteins have molecular masses between 19–26 kDa and consist of proteins with lengths of 156–166 and 172 amino acids. All IFN-α subtypes possess a common conserved sequence region between amino acid positions 115–151 while the amino-terminal ends are variable. Many IFN-α subtypes differ in their sequences at only one or two positions. Naturally occurring variants also include proteins truncated by 10 amino acids at the carboxy-terminal end.

There are at least 23 different IFN-α genes. They have a length of 1–2 kb and are clustered on human chromosome 9p22. Based upon the structures two types of IFN-alpha genes, designated class I and II, are distinguished. They encode proteins of 156–166 and 172 amino acids, respectively.

IFN-α is assayed by a cytopathic effect reduction test employing human and bovine cell lines. Minute amounts of IFN-α can be assayed also by detection of the Mx protein specifically induced by this interferon. A sandwich ELISA employing bi-specific monoclonal antibodies for rapid detection is also available.

Interferon gamma: IFN-γ is a dimeric protein with subunits of 146 amino acids. The protein is glycosylated at two sites, and the pI is 8.3–8.5. IFN-γ is synthesized as a precursor protein of 166 amino acids including a secretory signal sequence of 23 amino acids. Two molecular forms of the biologically active protein of 20 and 25 kDa have been described. Both of them are glycosylated at position 25. The 25 kDa form is also glycosylated at position 97. The observed differences of natural IFN-γ with respect to molecular mass and charge are due to variable glycosylation patterns. 40–60 kDa forms observed under non-denaturing conditions are dimers and tetramers of IFN-γ. The human gene has a length of approximately 6 kb. It contains four exons and maps to chromosome 12q24.1.

IFN-γ can be detected by sensitive immunoassays, such as an ELISA test that allows detection of individual cells producing IFN-γ. Minute amounts of IFN-γ can be detected indirectly by measuring IFN-induced proteins such as Mx protein. The induction of the synthesis of IP-10 has been used also to measure IFN-gamma concentrations. In addition, bioassays can be used to detect IFN-γ, such as an assay that employs induction of indoleamine 2,3-dioxygenase activity in 2D9 cells.

Interferon Inducible Protein 10: A cytokine that is 98 amino acids in length that has homology to platelet factor-4, and is a chemokine. The human IP-10 genes contains four exons and maps to chromosome 4q12-21.

Interleukin-10: IL-10 is a homodimeric protein with subunits having a length of 160 amino acids that is a cytokine. Human IL-10 shows 73 percent amino acid homology with murine IL-10. The human IL-10 gene contains four exons.

IL10 inhibits the synthesis of a number of cytokines such as IL-2 and IFN-γ in Th1 subpopulations of T-cells but not of Th2. IL10 can be detected with an ELISA assay. In addition, the murine mast cell line D36 can be used to bioassay human IL10. The intracellular factor can be detected also by flow cytometry.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Maturation: The process in which an immature cell, such as dendritic cell, changes in form or function to become a functional mature cell, such as an APC.

Neoplasm: An abnormal cellular proliferation, which includes benign and malignant tumors, as well as other proliferative disorders.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phophorothioate modified phosphate backbone (wherein at least one of the phosphate oxygens is replaced by sulfur). Other stabilized oligonucleotides include: non-ionic DNA analogs, such as alkyl- and aryl-phophonates (in which the charged phosphonate oxygen is replaced by an alkyl or aryl group), phophodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence and stimulates (e.g. has a mitogenic effect or induces cytokine production) vertebrate immune cells. The cytosine, guanine is unmethylated.

An "oligonucleotide delivery complex" is an oligonucleotide associated with (e.g. ionically or covalently bound to; or encapsulated within) a targeting means (e.g. a molecule that results in a higher affinity binding to a target cell (e.g. B-cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, J. immunol. 167: 3324, 2001)

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoimmune disorder. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide preparation is one in which the peptide or protein is more enriched than the peptide or protein is in its natural environment within a cell. Preferably, a preparation is purified such that the protein or peptide represents at least 50% of the total peptide or protein content of the preparation.

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence. In several embodiments, a self-complementary nucleic acid sequence includes 3, 4, 5, 6 or more bases that could form hydrogen bonds with 3, 4, 5, 6 or more bases, respectively, of the same nucleic acid sequence.

Therapeutically effective dose: A dose sufficient to prevent advancement, or to cause regression of the disease, or which is capable of relieving symptoms caused by the disease, such as pain or swelling.

Vaccine: A preparation of attenuated microorganisms (including but not limited to bacteria and viruses), living microorganisms, antigen, or killed microorganisms, administered for the prevention, amelioration or treatment of infectious disease.

A. CpG Oligodeoxynucleotides

K type CpG ODNs have been previously described. K ODNs which exhibit the greatest immunostimulatory activity share specific characteristics. These characteristics differ from those of the Formula II or D ODN (see below). In addition, K ODN have specific effects on the cells of the immune system, which differ from the effects of D ODN. For example, K ODN stimulate proliferation of B cells and stimulate the production of IL-6.

The K ODNs at least about 10 nucleotides and include a sequence represented by either Formula I:

$$5'\ N_1N_2N_3T\text{-}CpG\text{-}WN_4N_5N_6\ 3'$$

wherein the central CpG motif is unmethylated, W is A or T, and $N_1$, $N_2$, $N_3$, $N_4$, $N_5$, and $N_6$ are any nucleotides.

These Formula I or K ODN, stimulate B cell proliferation and the secretion of IgM and IL-6, processes involved in the body's humoral immunity, such as the production of antibodies against foreign antigens. In one embodiment, the K ODNs induce a humoral immune response.

In one embodiment, K type oligonucleotides of the formula

$$5'\ N_1N_2N_3T\text{-}CpG\text{-}WN_4N_5N_6\ 3'$$

contain a phosphate backbone modification. In one specific, non-limiting example, the phosphate backbone modification is a phosphorothioate backbone modification (i.e., one of the non-bridging oxygens is replaced with sulfur, as set forth in International Patent Application WO 95/26204, herein incorporated by reference). In one embodiment, K ODNs have a phophorothioate backbone, and at least one unmethylated CpG dinucleotide. Eliminating the CpG dinucleotide motif from the K ODN significantly reduces immune activation. Incorporating multiple CpGs in a single K ODN increases immune stimulation. Preferably, the K ODN are at least 12 bases long. In addition, K ODN containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

D type ODNs differ both in structure and activity from K type ODNs. The unique activities of D type ODNs are disclosed below (see section C). For example, as disclosed herein, D oligodeoxynucleotides stimulate the release of cytokines from cells of the immune system. In specific, non-limiting examples D type oligonucleotides stimulate the release or production of IP-10 and IFN-α by monocytes and/or plasmacitoid dendritic cells and the release or production of IFN-γ by NK cells. The stimulation of NK cells by D oligodeoxynucleotides can be either direct or indirect.

With regard to structure, in one embodiment, a CpG motif in a D type oligonucleotides has been described by Formula II:

$$5'\ RY\text{-}CpG\text{-}RY\ 3'$$

wherein the central CpG motif is unmethylated, R is A or G (a purine), and Y is C or T (a pyrimidine). D-type oligonucleotides include an unmethylated CpG dinucleotide. Inversion, replacement or methylation of the CpG reduces or abrogates the activity of the D oligonucleotide.

In one embodiment, a D type ODN is at least about 16 nucleotides in length and includes a sequence represented by Formula III:

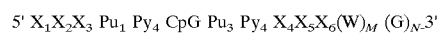

$$5'\ X_1X_2X_3\ Pu_1\ Py_4\ CpG\ Pu_3\ Py_4\ X_4X_5X_6(W)_M\ (G)_N\ 3'$$

wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1\ Py_2\ CpG\ Pu_3\ Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN these nucleotides are termed the 5' far flanking region. Nucleotides 3' of $X_4X_5X_6$ in the D ODN are termed the 3' far flanking region.

In one specific non-limiting example, $Py_2$ is a cytosine. In another specific, non-limiting example, $Pu_3$ is a guanidine. In yet another specific, non limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific not limiting example, N is from about 4 to about 8. In another specific, non-limiting example, N is about 6.

D-type CpG oligonucleotides can include modified nucleotides. Without being bound by theory, modified nucleotides can be included to increase the stability of a D-type oligonucleotide. Without being bound by theory, because phosphorothioate-modified nucleotides confer resistance to exonuclease digestion, the D ODN are "stabilized" by incorporating phosphorothioate-modified nucleotides. In one embodiment, the CpG dinucleotide motif and its immediate flanking regions include phosphodiester rather than phosphorothioate nucleotides. In one specific non-limiting example, the sequence $Pu_1\ Py_2\ CpG\ Pu_3\ Py_4$ includes phosphodiester bases. In another specific, non-limiting example, all of the bases in the sequence $Pu_1\ Py_2\ CpG\ Pu_3\ Py_4$ are phosphodiester bases. In yet another specific, non-limiting example, $X_1X_2X_3$ and $X_4X_5X_6(W)_M\ (G)_N$ include phosphodiester bases. In yet another specific, non-limiting example, $X_1X_2X_3\ Pu_1\ Py_2\ CpG\ Pu_3\ Py_4\ X_4X_5X_6(W)_M\ (G)_N$ include phosphodiester bases. In further non-limiting examples the sequence $X_1X_2X_3$ includes at most one or at most two phosphothioate bases and/or the sequence $X_4X_5X_6$ includes at most one or at most two phosphotioate bases. In additional non-limiting examples, $X_4X_5X_6(W)_M\ (G)_N$ includes at least 1, at least 2, at least 3, at least 4, or at least 5 phosphothioate bases. Thus, a D type oligodeoxynucleotide can be a phosphorothioate/phosphodiester chimera.

As disclosed herein, any suitable modification can be used in the present invention to render the D oligodeoxynucleotide resistant to degradation in vivo (e.g., via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D type oligodeoxynucleotides can also be modified to contain a secondary structure (e.g., stem loop structure). Without being bound by theory, it is believed that incorporation of a stem loop structure renders and oligodeoxynucleotide more effective.

In a further embodiment, $Pu_1\ Py_2$ and $Pu_3\ Py_4$ are self-complementary. In another embodiment, $X_1X_2X_3$ and $X_4X_5X_6$ are self complementary. In yet another embodiment $X_1X_2X_3\ Pu_1\ Py_2$ and $Pu_3\ Py_4\ X_4X_5X_6$ are self complementary.

Specific non-limiting examples of a D type oligonucleotide wherein $Pu_1\ Py_2$ and $Pu_3\ Py_4$ are self-complementary include, but are not limited to, AT<u>CG</u>AT, AC<u>CG</u>GT, ATCGAC, ACCGAT, GT<u>CG</u>AC, or GC<u>CG</u>GC. Without being bound by theory, the self-complementary base sequences can help to form a stem-loop structure with the CpG dinucleotide at the apex to facilitate immunostimulatory functions. Thus, in one specific, non-limiting example, D type oligonucleotides wherein $Pu_1\ Py_2$ and $Pu_3\ Py_4$ are self-complementary induce higher levels of IFN-γ production from a cell of the immune system (see below). The self-complementary need not be limited to $Pu_1\ Py_2$ and $Pu_3\ Py_4$. Thus, in another embodiment, additional bases on each side of the three bases on each side of the CpG-containing hexamer form a self-complementary sequence (see above).

One specific, non-limiting example of a sequence wherein $Pu_1\ Py_2$ and $Pu_3\ Py_4$ are self-complementary but wherein the far-flanking sequences are not self-complementary is

GGTGCATCGATACAGGGGGG (ODN D 113, SEQ ID NO:11).

This oligodeoxynucleotide has a far flanking region that is not self complementary and induces high levels of IFN-γ and IFN-α.

Another specific, non-limiting example of a D oligodeoxynucleotides is:

GGTGCGTCGATGCAGGGGGG (D28, SEQ ID NO:7).

This oligodeoxynucleotide is of use for inducing production and/or release of cytokines from immune cells, although it lacks a self-complementary motif.

In one embodiment, the D type oligodeoxynucleotides disclosed herein are at least about 16 nucleotides in length. In a second embodiment, a D type oligodeoxynucleotide is at least about 18 nucleotides in length. In another embodiment, a D type oligodeoxynucleotide is from about 16 nucleotides in length to about 100 nucleotides in length. In yet another embodiment, a D type oligodexoynucleotide is from about 16 nucleotides in length to about 50 nucleotides in length. In a further embodiment, a D type oligodeoxynucleotide is from about 18 nucleotides in length to about 30 nucleotides in length.

In another embodiment, the oligodeoxynucleotide is at least 18 nucleotides in length, and at least two G's are included at the 5' end of the molecule, such that the oligodeoxynucleotide includes a sequence represented by Formula IV:

$$5'\ GGX_1X_2X_3\ Pu_1\ Py_2\ CpG\ Pu_3\ Py_4\ X_4X_5X_6(W)_M\ (G)_N\text{-}3'.$$

The D type oligodeoxynucleotide can include additional G's at the 5' end of the oligodeoxynucleotide. In one specific example, about 1 or about 2 G's are included at the 5' end of an olgiodeoxynucleotide including a sequence as set forth as Formula IV.

Examples of a D type oligodeoxynucleotide include, but are not limited to, 5'XXTGCATCGATGCAGGGGGG 3' (SEQ ID NO: 12)

5'XXTGCACCGGTGCAGGGGGG3' (SEQ ID NO: 13),

5'XXTGCGTCGACGCAGGGGGG3' (SEQ ID NO: 14),

5'XXTGCGTCGATGCAGGGGGG3' (SEQ ID NO: 16),

5'XXTGCGCCGGCGCAGGGGGG3' (SEQ ID NO: 17),

5'XXTGCGCCGATGCAGGGGGG3' (SEQ ID NO: 18),

5'XXTGCATCGACGCAGGGGGG3' (SEQ ID NO: 19),

5'XXTGCGTCGGTGCAGGGGGG3' (SEQ ID NO: 20), wherein X any base, or is no base at all. In one specific, non-limiting example, X is a G.

The oligodeoxynucleotides disclosed herein can be synthesized de novo using any of a number of procedures well known in the art. For example, the oligodeoxynucleotides can be synthesized as set forth in U.S. Pat. No. 6,194,388, which is herein incorporated by reference in its entirety. A D type oligodeoxynucleotide may be synthesized using, for example, the B-cyanoethyl phophoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

B. Delivery Complexes and Pharmaceutical Compositions

In one embodiment, a D type oligodeoxynucleotide is included in delivery complex. The delivery complex can include the D type ODN and a targeting means. Any suitable targeting means can be used. For example, a D type oligodeoxynucleotide can be associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of an oligodeoxynucleotide delivery complexes include a D type oligodeoxynucleotide associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the oligodeoxynucleotide is released in a functional form at the target cells.

In one embodiment, a pharmacological composition is provided that includes a D type oligonucleotide and a pharmacologically acceptable carrier. Pharmacologically acceptable carriers (e.g., physiologically or pharmaceutically acceptable carriers) are well known in the art. A suitable pharmacological composition can be formulated to facilitate the use of a D type ODN in vivo and/or ex vivo. Such a composition can be suitable for delivery of the active ingredient to any suitable host, such as a patient for medical application, and can be manufactured in a manner that is itself known, e.g., by means of conventional mixing, dissolving, granulating, dragee-making, levigating, emulsifying, encapsulating, entrapping or lyophilizing processes.

Pharmacological compositions for use can be formulated in a conventional manner using one or more pharmacologically (e.g., physiologically or pharmaceutically) acceptable carriers comprising excipients, as well as optional auxiliaries that facilitate processing of the active compounds into preparations which can be used pharmaceutically. Proper formulation is dependent upon the route of administration chosen, and whether use will be an in vivo or an ex vivo use. For use in vivo, administration can be either systemic or local. In addition, one of skill in the art can readily select a suitable route of administration, including, but not limited to intravenous, intramuscular, intraperitoneal, transmucosal, subcutaneous, transdermal, transnasal, and oral administration.

Thus, for injection, the active ingredient can be formulated in aqueous solutions, preferably in physiologically compatible buffers. For transmucosal administration, penetrants appropriate to the barrier to be permeated are used in the formulation. Such penetrants are generally known in the art. For oral administration, the active ingredient can be combined with carriers suitable for inclusion into tablets, pills, dragees, capsules, liquids, gels, syrups, slurries, suspensions and the like. For administration by inhalation, the active ingredient is conveniently delivered in the form of an aerosol spray presentation from pressurized packs or a nebuliser, with the use of a suitable propellant. The active ingredient can be formulated for parenteral administration by injection, e.g., by bolus injection or continuous infusion. Similarly, D type oligodeoxynucleotides can be formulated for intratracheal or for inhalation. Such compositions can take such forms as suspensions, solutions or emulsions in oily or aqueous vehicles, and can contain formulatory agents such as suspending, stabilizing and/or dispersing agents. Other pharmacological excipients are known in the art.

C. Method of Inducing an Immune Response

A method is disclosed herein for stimulating a cell of the immune system. The method includes contacting the cell with an effective amount of a D type oligodeoxynucleotide disclosed herein, thereby stimulating the cell (see also PCT Application Nos. WO0061151A3, WO9956755A1, WO9840100A1, WO9818810A1, WO0122990A2; which are herein incorporated by reference in their entirety).

In contrast, D type oligodeoxynucleotides have different immunostimulatory activities. As disclosed herein, administration of a D type oligodexoynucleotide activates monocytes and/or natural killer cells, and induces the maturation of dendritic cells. Furthermore, a D type oligodeoxynucleotide can be used to increase the production of cytokines (for example IP-10, IFN-α or IFN-γ) by a cell of the immune system.

Administration of the D type oligodeoxynucleotide can be by any suitable method. For example, the ODN can be administered in vivo or ex vivo.

Thus, in one embodiment, a method is also disclosed herein for producing an immune response in a subject. The subject can be any mammal, particularly a primate, such as a human. The method includes administering a D type oligodeoxynucleotide to the subject, thereby inducing the immune response. In yet one embodiment, the immune response includes induction of the maturation of a dendritic cell or the activation of a natural killer cell and/or a monocyte. In a further embodiment, the immune response includes the production of a cytokine, such as, for example, IL-10, IP-10, IFN-α or IFN-γ.

In one embodiment, a method is provided for inducing an immune response in a subject wherein the method includes contacting a monocyte or a dendritic cell precursor in vitro with a D type oligodeoxynucleotide to produce an activated antigen presenting cell. The monocytes or dendritic cell precursors can be contacted with the D type oligodeoxynucleotides in the presence of or in the absence of antigen. The activated antigen presenting cell is then administered to the subject to induce an immune response.

In another embodiment, a method is provided herein for inducing an immune response in a subject that includes contacting a monocyte or a dendritic cell precursor in vitro with a D type oligodeoxynucleotide to produce an activated antigen presenting cell. The monocytes or dendritic cell precursors can be contacted with the D type oligodeoxynucleotides in the presence of or in the absence of antigen. Lymphocytes or natural killer are then contacted with the activated antigen presenting cells in vitro, or with cytokines secreted by the activated antigen presenting cells in vitro, to produce activated lymphocytes or activated natural killer cells. The activated lymphocytes or natural killer cells are administered to the subject to induce the immune response.

In order to induce an immune response, a D type oligodeoxynucleotide is administered either alone or in conjunction with another molecule. Co-administration includes administering the molecule and the D type oligodeoxynucleotide at the same time, or sequentially. The other molecule can be any other agent, such as a protein, an antigenic epitope, a hydrocarbon, lipid, mitogen, an anti-infectious agent (such as antiviral, antifungal, or anti-bacterial agent) or a vaccine (such as a live, attenuated, or heat-killed vaccine).

Without being bound by theory, when administered to a subject, it is believed that the ODNs initially act on antigen presenting cells (e.g., B cells, macrophages and dendritic cells). These cells then release cytokines, which activate natural killer (NK) cells. The activation of natural killer cells may be direct (e.g. through contact of the NK cell with a D type ODN) or indirect (e.g. by activating the secretion of cytokines, which then activate the natural killer cells). Either a cell-mediated or humoral immune response then occurs in the host.

As disclosed herein, D type oligodeoxynucleotides are a unique type of CpG containing oligodeoxynucleotides that have specific effects on the cells of the immune system. For several examples, D type oligonucleotides activate natural killer cells and monocytes, and induce the maturation of dendritic cells. In other examples, D type oligodeoxynucleotides increase production of cytokines such as IP-10, IL-10, IFNα and IFN-γ. These effects are different from the effects of K type oligodeoxynucleotides. As previously described, K type oligodeoxynucleotides support B cell proliferation, and induce the production of IL-6. Thus, the elucidation of the immunostimulatory effects of D type oligodeoxynucleotides allows for customizing or tailoring of the type of immune obtained by administration of oligodeoxynucleotides. For example, a K type oligodeoxynucleotide can be utilized when production of IL-6 is desired, whereas D type oliogdeoxynucleotides can be used when production of IFN-γ is desired.

In one embodiment, a D type oligodeoxynucleotide is administered to a subject, such as a subject that has an autoimmune disease. Specific, non-limiting examples of autoimmune diseases include, but are not limited to diabetes, rheumatoid arthritis, lupus erythematosus, and multiple sclerosis. In one embodiment, the subject has cancer.

Also disclosed herein are methods of use to treat, prevent, or ameliorate an allergic reaction in a subject. An allergy refers to an acquired hypersensitivity to a substance (i.e., an allergen). Allergic conditions include eczema, allergic rhinitis or coryza, hay fever, bronchial asthma, uticaria (hives), food allergies, and other atopic conditions. The list of allergens is extensive and includes pollens, insect venoms, animal dander, dust, fungal spores, and drugs (e.g., penicillin). Examples of natural, animal, and plant allergens can be found in International Patent Application WO 98/18810. In one embodiment a D-type oligodeoxynucleotide administered to a subject to treat an allergic condition such as allergic asthma. In another embodiment, the D type oligodeoxynucleotide is administered in combination with any suitable anti-allergenic agent. Suitable anti-allergenic agents include those substances given in treatment of the various allergic conditions described above, examples of which can be found in the Physicians' Desk Reference (1998).

In another embodiment, a D type oligodeoxynucleotide is administered to a subject that has a neoplasm. The D-type oligodeoxynucleotide is administered either alone or in combination with any suitable anti-neoplastic agent, such as a chemotherapeutic agent or radiation. Suitable neoplasms include, but are not limited to, solid tumors such as cancers of the brain, lung (e.g., small cell and non-small cell), ovary, breast, prostate, and colon, as well as carcinomas and sarcomas. Without being bound by theory, it is believed that the D type oligodeoxynucleotide increases the immune response to the neoplasm, and thus is involved in the reduction of tumor burden.

In a further embodiment, a method is provided to enhance the efficacy of any suitable vaccine. Suitable vaccines include those directed against Leishmania, Hepatitis A, B, and C, examples of which can be found in the Physicians' Desk Reference (1998), and DNA vaccines directed against, for example, malaria. (See generally Klinman et al., 17 Vaccine 17: 19, 1999; McCluskie and Davis, J. Immun. 161:4463, 1998).

D type oligodeoxynucleotides can be used to treat, prevent, or ameliorate any condition associated with an infectious agent. The D type oligodeoxynucleotide can be administered to a subject infected with the infectious agent alone or in combination with any suitable anti-infectious agent, such as an antiviral, anti-fungal or anti-bacterial agent (see Physicians' Desk Reference, 1998). Specific, non-limiting examples of infectious agents conditions associated with infectious agents are tularemia, francisella, schistosomiasis, tuberculosis, malaria, and leishmaniasis. Examples of infectious agents are viruses, bacteria, fungi, and other organisms (e.g., protists) can be found in International Patent Application WO 98/18810.

The D type oligodeoxynucleotides disclosed herein can also be used with any suitable antisense therapy. Suitable antisense agents are those that specifically bind either with a target DNA or a target RNA and inhibit expression of the target sequence (see Lonnberg et al., Ann. Med. 28: 511, 1996; Alama et al., Pharmacol. Res. 36: 171, 1997; Scanlon et al., FASEB J. 9: 1288, 1995; Oberbauer, 109 Wien Klin Wochenschr 109: 40, 1997).

The present invention is further described in the following examples. These examples are intended only to illustrate the invention and are not intended to limit the scope of the invention in any way.

EXAMPLES

Example 1

Cytokine Production

The oligodeoxynucleotides disclosed herein can be used to produce an immune response. In one embodiment, an immune response can be measured by cytokine production. As shown herein, K type oligodexoynucleotides can be used to increase the production of the cytokines IL-6 and induce cell proliferation. D type oligodeoxynucleotides induce the production of IFN-γ.

Human peripheral blood mononuclear cells (PBMC) were isolated, as described elsewhere (Ballas et al., J. Allergy Clin. Immunol. 85: 453, 1990; Ballas a Rasmussen, J. Immunol. 45:1039, 1990; Ballas and Rasmussen, J. Immunol. 150: 17, 1993). Oligodeoxynucleotides (ODNs) were synthesized on a DNA synthesizer (Applied Biosystems Inc., Foster City, Calif.), as described elsewhere (Beacage and Caruthers, Tetrahedron Letters 22: 1859, 1981). In some ODNs, the normal DNA backbone phosphodiesterase linkages were replaced with phosphorothioate linkages, as described elsewhere (Agrawal et al., Proc. Natl. Acad. Sci. USA 94: 2620, 1997; Agrawal TIB TECH 14: 376, 1996). To reduce degradation of the ODNs, those that did not have an entire phosphorothioate backbone contained phosphorothioate linkages at the 5' and 3' ends. Cells were incubated for approximately 72 hrs with the various ODNs. IL-6 and TNF-γ levels were determined by ELISA using anti-IL-6 and anti-TNF-γ antibodies, as described elsewhere (Maniatis et al., *Molecular Cloning: A Laboratory Manual*, Cold Spring Harbor Laboratory Press, New York, 1989). Cell proliferation was determined by [$^3$H] thymidine incorporation, as described elsewhere (Liang et al., J Clin. Invest. 98:1121, 1996).

IL-6 levels and cell proliferation are set forth in Table 1: Induction of a Humoral Immune Response In Vitro. These data demonstrate that a sequence containing 5' $N_1N_2N_3T$-CpG-$WN_4N_5N_6$ 3', wherein the central CpG motif is unmethylated, W is A or T, and $N_1$, $N_2$, $N_3$, $N_4$, $N_5$, and $N_6$ are any nucleotides, (K type oligodeoxynucleotides) induce a the production of IL-6 and a humoral immune response. However, D type oligodeoxynucleotides induce only low levels of IL-6 production.

In addition, maximum induction was observed for K type ODNs that contained a phosphorothioate backbone. IFN-γ levels and cell proliferation are set forth in Table 1. These data demonstrate that D type oligonucletotides increase production of IFN-γ. Maximum induction occurred with ODNs containing phosphodiesterase linkages.

TABLE 1

| ODN | SEQUENCE | | IFN-g* | | IL-6* | | IgM* | | PROLIF* | |
|---|---|---|---|---|---|---|---|---|---|---|
| media | (None) | | 0.9 | 0.8 | 0.7 | 1 | 0.5 | 0.5 | 0.9 | 0.6 |
| D ODN | | | | | | | | | | |
| DV104 | GGTGCATCGATGCAGGGGGG | (SEQ ID NO:1) | 47.7 | 64.7 | 30.8 | 31 | 10.2 | 12.3 | 2.9 | 1.7 |
| DV19 | GGTGCATCGATGCAGGGGGG | (SEQ ID NO:1) | 44.0 | 71.8 | 12.5 | 17 | 9.6 | 21.0 | 3.1 | 3.1 |
| DV29 | GGTGCACCGGTGCAGGGGGG | (SEQ ID NO:2) | 35.9 | 38.9 | 3.8 | 4 | 2.5 | 2.9 | 1.7 | 1.2 |
| DV35 | GGTGCATCGATGCAGGGGGG | (SEQ ID NO:1) | 33.3 | 63.6 | 28.0 | 29 | 5.7 | 8.4 | 2.0 | 1.1 |
| DV28 | GGTGCGTCGATGCAGGGGGG | (SEQ ID NO:7) | 32.2 | 45.3 | 13.8 | 23 | 9.0 | 14.3 | 2.8 | 2.0 |
| DV106 | GGTGTGTCGATGCAGGGGGG | (SEQ ID NO:26) | 29.9 | 71.4 | 7.5 | 6 | 32.2 | 94.5 | 2.9 | 1.8 |
| DV116 | TGCATCGATGCAGGGGGG | (SEQ ID NO:12) | 25.1 | 28.9 | 28.3 | 25 | 6.2 | 3.3 | 2.6 | 1.6 |
| DV113 | GGTGCATCGATACAGGGGGG | (SEQ ID NO:11) | 21.1 | 15.3 | 144.8 | 255 | 4.0 | 4.2 | 4.7 | 5.6 |
| DV34 | GGTGCATCGATGCAGGGGGG | (SEQ ID NO:1) | 16.2 | 19.1 | 3.6 | 6 | 2.4 | 2.6 | 3.2 | 4.5 |
| DV102 | GGTGCATCGTTGCAGGGGGG | (SEQ ID NO:30) | 15.8 | 39.4 | 6.6 | 7 | 24.0 | 58.0 | 2.1 | 1.1 |
| DV32 | GGTGCGTCGACGCAGGGGGG | (SEQ ID NO:31) | 14.5 | 18.0 | 2.7 | 5 | 1.4 | 2.1 | 2.8 | 0.9 |
| DV117 | GGTCGATCGATGCACGGGGG | (SEQ ID NO:32) | 13.4 | 14.6 | 25.8 | 23 | 19.6 | 22.8 | 6.2 | 2.7 |
| DV37 | GGTGCATCGATGCAGGGGGG | (SEQ ID NO:1) | 13.0 | 19.6 | 13.3 | 21 | 38.0 | 33.0 | 4.8 | 3.6 |
| DV25 | GGTGCATCGATGCAGGGGGG | (SEQ ID NO:1) | 12.2 | 7.9 | 2.0 | 3 | 2.1 | 2.7 | 0.9 | 0.7 |
| DV30 | GGTGCATCGACGCAGGGGGG | (SEQ ID NO:35) | 11.3 | 8.1 | 2.4 | 3 | 6.4 | 6.9 | 2.4 | 1.2 |
| dv120 | GGTGCATCGATAGGCGGGGG | (SEQ ID NO:36) | 8.7 | 11.5 | 1.0 | 1 | 3.5 | 1.1 | 1.9 | 1.0 |
| DV27 | GGTGCACCGATGCAGGGGGG | (SEQ ID NO:37) | 8.5 | 7.3 | 2.9 | 4 | 3.3 | 4.9 | 1.9 | 1.5 |
| dv119 | CCTGCATCGATGCAGGGGGG | (SEQ ID NO:38) | 7.5 | 9.1 | 2.0 | 1 | 1.6 | 0.4 | 1.0 | 0.3 |
| D142 | GGTATATCGATATAGGGGGG | (SEQ ID NO:39) | 7.3 | 1.1 | 15.9 | 5 | 22.5 | 5.0 | 2.0 | 1.0 |
| d143 | GGTGGATCGATCCAGGGGGG | (SEQ ID NO:40) | 6.4 | 4.5 | 16.0 | 8 | 47.0 | 12.0 | 2.0 | 1.0 |
| D CONTROLS | | | | | | | | | | |
| dv17 | GGTGCAACGTTGCAGGGGGG | (SEQ ID NO:41) | 2.3 | 1.5 | 5.0 | 4 | 8.0 | 2.0 | 4.0 | 2.0 |
| DV78 | GGTGCATCGATAGAGGGGGG | (SEQ ID NO:42) | 0.8 | 0.5 | 2.0 | 4 | 4.2 | 3.0 | 1.4 | 0.9 |
| DV96 | GGTGCATCGTAGCAGGGGGG | (SEQ ID NO:43) | 1.1 | 0.7 | 1.5 | 2 | 1.1 | 2.9 | 1.2 | 0.3 |
| DV95 | GGTGGTTCGATGCAGGGGGG | (SEQ ID NO:44) | 2.1 | 2.2 | 2.5 | 3 | 1.2 | 1.8 | 1.2 | 0.7 |
| DV93 | GGTGCATCGATGCAGGGGGG | (SEQ ID NO:1) | 0.9 | 1.3 | 11.9 | 26 | 2.7 | 3.5 | 1.5 | 0.6 |
| DV92 | GGTGCACCGGTGCAAAAAAA | (SEQ ID NO:46) | 0.4 | 0.7 | 2.0 | 3 | 0.8 | 1.2 | 1.4 | 0.8 |

TABLE 1-continued

| ODN | SEQUENCE | | IFN-g* | | IL-6* | | IgM* | | PROLIF* | |
|---|---|---|---|---|---|---|---|---|---|---|
| DV81 | GGTGCATCGATAGAGGGG | (SEQ ID NO:47) | 0.8 | 1.1 | 1.2 | 2 | 1.2 | 1.6 | 1.4 | 0.6 |
| DV77 | GGTGCATCGATGCAGGGGGG | (SEQ ID NO:1) | 1.0 | 1.6 | 9.5 | 13 | 82.1 | 181.9 | 6.5 | 12.2 |
| DV76 | GGTGCATCGATGCAAAAAAA | (SEQ ID NO:49) | 1.6 | 1.5 | 1.3 | 2 | 1.2 | 1.5 | 1.7 | 0.4 |
| DV71 | GGGGTCGACAGGG | (SEQ ID NO:50) | 1.4 | 2.2 | 1.8 | 2 | 0.7 | 0.5 | 1.2 | 1.0 |
| DV49 | GGTGCATAAATGCAGGGGGG | (SEQ ID NO:51) | 1.5 | 1.2 | 1.3 | 2 | 1.0 | 1.0 | 1.2 | 1.0 |
| DV48 | GGTGCATCAATGCAGGGGGG | (SEQ ID NO:52) | 1.0 | 0.5 | 1.2 | 2 | 1.0 | 1.0 | 1.2 | 1.0 |
| DV47 | GGTGCATTGATGCAGGGGGG | (SEQ ID NO:53) | 1.2 | 0.5 | 1.5 | 2 | 1.0 | 1.0 | 1.2 | 1.0 |
| DV45 | GGTGCATC*GATGCAGGGGGG | (SEQ ID NO:54) | 3.4 | 2.9 | 7.0 | 14 | 0.8 | 1.5 | 1.3 | 0.3 |
| DV26 | GGTGCATGCATGCAGGGGGG | (SEQ ID NO:55) | 7.6 | 15.3 | 0.0 | 0 | 0.6 | 1.0 | 1.3 | 1.4 |
| DV20 | GGTGCATGCATGCAGGGGGG | (SEQ ID NO:55) | 2.3 | 4.2 | 2.1 | 2 | 1.0 | 1.8 | 1.1 | 0.8 |
| DV122 | GGTGCATTGATGCAGGGGGG | (SEQ ID NO:53) | 0.9 | 1.5 | 1.3 | 1 | 2.0 | 0.4 | 0.7 | 0.3 |
| DV114 | GGTGCACTGGTGCAGGGGGG | (SEQ ID NO:58) | 1.8 | 2.0 | 1.8 | 2 | 1.2 | 1.2 | 1.0 | 0.6 |
| DV111 | GGTGTATCGATGCAAAAGGG | (SEQ ID NO:59) | 5.8 | 5.1 | 12.3 | 13 | 4.8 | 7.6 | 4.4 | 8.0 |
| DV108 | GGTGCCCCGTTGCAGGGGGG | (SEQ ID NO:60) | 1.2 | 1.4 | 1.7 | 3 | 1.0 | 1.5 | 1.0 | 0.2 |
| DV107 | GGTGCAACGGGGCAGGGGGG | (SEQ ID NO:61) | 2.5 | 3.3 | 7.7 | 15 | 0.4 | 0.6 | 1.1 | 0.4 |
| DV105 | AATGCATCGATGCAAAAAAA | (SEQ ID NO:62) | 1.1 | 1.8 | 2.4 | 3 | 1.2 | 1.5 | 1.0 | 0.4 |
| DV103 | GGTGCACCGTGGCAGGGGGG | (SEQ ID NO:63) | 9.4 | 16.8 | 8.7 | 12 | 5.4 | 8.4 | 1.7 | 1.9 |
| DV100 | GGTGCATCGAAGCAGGGGGG | (SEQ ID NO:64) | 3.4 | 3.5 | 7.2 | 6 | 21.0 | 24.0 | 9.1 | 5.9 |
| d79 | GGTGGATCGATGCAGGGGGG | (SEQ ID NO:65) | 0.6 | 0.5 | 1.0 | 1 | 23.0 | 2.0 | | |
| d145 | GGTGCACGCGTGCAGGGGGG | (SEQ ID NO:5) | 4.8 | 0.8 | 2.5 | 4 | 16.8 | 3.0 | | |
| d144 | GGTGCATGTATGCAGGGGGG | (SEQ ID NO:67) | 0.0 | 0.0 | 0.6 | 1 | 1.3 | 2.0 | | |
| AA20 | GGGGGATCGATGGGGG | (SEQ ID NO:68) | 2.7 | 5.1 | 3.1 | 3 | 2.2 | 2.5 | 1.6 | 1.2 |
| AA3M | GGGGGAAGCTTCGGGG | (SEQ ID NO:69) | 2.2 | 3.2 | 1.1 | 2 | 0.4 | 0.8 | 1.2 | 1.0 |
| K ODN | | | | | | | | | | |
| K22 | CTCGAGCGTTCTC | (SEQ ID NO:70) | 9.3 | 1.8 | 43.3 | 20 | 131.8 | 94.0 | 18.3 | 3.3 |
| DV84 | ACTCTCGAGCGTTCTA | (SEQ ID NO:71) | 1.1 | 1.6 | 42.6 | 91 | 79.7 | 105.3 | 18.5 | 25.8 |
| K21 | TCTCGAGCGTTCTC | (SEQ ID NO:72) | 7.2 | 2.8 | 39.6 | 17 | 237.6 | 194.2 | 34.6 | 9.3 |
| K82 | ACTCTGGAGCGTTCTC | (SEQ ID NO:73) | 1.9 | 0.1 | 38.5 | 5 | 25.5 | 16.8 | 10.7 | 0.6 |
| K30 | TGCAGCGTTCTC | (SEQ ID NO:74) | 9.5 | 10.5 | 30.8 | 31 | 253.1 | 256.3 | 7.0 | 6.9 |
| k31 | TCGAGGCTTCTC | (SEQ ID NO:75) | 22.1 | 26.3 | 30.7 | 18 | 290.3 | 150.6 | 12.9 | 9.0 |
| K39 | GTCGGCGTTGAC | (SEQ ID NO:76) | 7.0 | 11.0 | 27.3 | 22 | 100.3 | 137.9 | 16.1 | 6.3 |
| K16 | TCGACTCTCGAGCGTTCTC | (SEQ ID NO:8) | 3.1 | 3.1 | 25.2 | 21 | 72.7 | 79.5 | 22.3 | 20.6 |
| K3 | ATCGACTCTCGAGCGTTCTC | (SEQ ID NO:3) | 9.0 | 22.7 | 22.6 | 17 | 113.5 | 60.0 | 25.0 | 19.4 |
| k23 | TCGAGCGTTCTC | (SEQ ID NO:79) | 5.2 | 8.3 | 21.9 | 28 | 111.3 | 145.4 | 28.3 | 16.0 |
| DV110 | TCGAGGCTTCTC | (SEQ ID NO:75) | 2.2 | 2.2 | 21.8 | 25 | 70.3 | 142.8 | 19.6 | 19.8 |
| K40 | GTCGGCGTCGAC | (SEQ ID NO:81) | 11.3 | 14.3 | 20.7 | 11 | 127.1 | 222.2 | 11.0 | 5.0 |
| DV101 | CTCGAGCGTTCT | (SEQ ID NO:10) | 2.6 | 2.2 | 20.0 | 26 | 28.0 | 34.3 | 25.3 | 28.3 |
| DV89 | ACTCTTTCGTTCTC | (SEQ ID NO:83) | 1.6 | 1.6 | 19.7 | 23 | 169.1 | 390.3 | 6.7 | 7.2 |
| K34 | GTCGACGTTGAC | (SEQ ID NO:84) | 4.3 | 5.3 | 17.2 | 8 | 265.8 | 273.4 | 11.3 | 6.7 |

TABLE 1-continued

| ODN | SEQUENCE | | IFN-g* | | IL-6* | | IgM* | | PROLIF* | |
|---|---|---|---|---|---|---|---|---|---|---|
| DV86 | ACTCTCGAGCGTTCTC | (SEQ ID NO:9) | 0.8 | 1.6 | 16.9 | 37 | 36.0 | 40.7 | 5.1 | 3.0 |
| K83 | ACTCTCGAGGGTTCTC | (SEQ ID NO:86) | 0.0 | 0.0 | 16.5 | 5 | 16.9 | 9.7 | 6.9 | 0.7 |
| K19 | ACTCTCGAGCGTTCTC | (SEQ ID NO:9) | 4.8 | 7.9 | 14.8 | 16 | 151.0 | 223.6 | 23.4 | 16.1 |
| DV88 | ACTCTCGAGCGTTCTCAAAA | (SEQ ID NO:88) | 1.9 | 3.0 | 14.5 | 14 | 49.7 | 55.0 | 10.2 | 11.5 |
| DV85 | CATCTCGAGCGTTCTC | (SEQ ID NO:89) | 0.9 | 1.5 | 12.0 | 11 | 82.0 | 126.8 | 12.2 | 13.0 |
| K73 | GTCGTCGATGAC | (SEQ ID NO:90) | 4.5 | 5.2 | 11.7 | 7 | 99.2 | 110.7 | 17.7 | 13.2 |
| DV109 | TCGAGCGTTCT | (SEQ ID NO:4) | 2.2 | 2.2 | 11.3 | 9 | 28.4 | 46.4 | 14.5 | 12.6 |
| D123 | TCGTTCGTTCTC | (SEQ ID NO:92) | 3.3 | 1.6 | 9.6 | 12 | 50.9 | 72.3 | 39.3 | 30.5 |
| D124 | TCGTTTGTTCTC | (SEQ ID NO:93) | 3.0 | 2.0 | 7.3 | 6 | 63.2 | 88.6 | 34.1 | 28.1 |
| K46 | GTCGACGCTGAC | (SEQ ID NO:94) | 3.5 | 5.1 | 5.2 | 2 | 21.9 | 15.1 | 8.7 | 5.0 |
| D139 | TCGATGCTTCTC | (SEQ ID NO:95) | 2.2 | 1.4 | 5.1 | 4 | 97.8 | 157.5 | 39.1 | 27.9 |
| D137 | TCGCCGCTTCTC | (SEQ ID NO:96) | 1.4 | 0.5 | 4.3 | 2 | 78.7 | 107.6 | 31.6 | 22.3 |
| K47 | GTCGACGTCGAC | (SEQ ID NO:54) | 3.8 | 7.1 | 3.9 | 1 | 14.1 | 6.2 | 5.8 | 2.3 |
| K72 | GTCATCGATGCA | (SEQ ID NO:98) | 1.8 | 2.3 | 3.7 | 3 | 95.6 | 79.3 | 11.0 | 5.4 |
| DV90 | ACTCTTTCGATCTC | (SEQ ID NO:99) | 1.6 | 2.0 | 3.6 | 4 | 19.2 | 24.8 | 4.6 | 5.7 |
| K37 | GTCAGCGTCGAC | (SEQ ID NO:100) | 10.8 | 19.5 | 3.4 | 1 | 52.4 | 63.0 | 6.4 | 2.2 |
| k25 | TCGAGCGTTCT | (SEQ ID NO:4) | 3.6 | 3.7 | 2.9 | 4 | 17.9 | 24.8 | | |
| D127 | TGGAGCGTTCTC | (SEQ ID NO:102) | 2.3 | 1.6 | 2.8 | 3 | 89.7 | 136.4 | 21.4 | 11.9 |
| D138 | TGCTGCGTTCTC | (SEQ ID NO:103) | 0.7 | 0.7 | 2.1 | 1 | 69.0 | 105.5 | 18.4 | 12.1 |
| D125 | TTGAGCGTACTC | (SEQ ID NO:104) | 3.3 | 3.2 | 2.0 | 1 | 35.1 | 53.8 | 7.8 | 5.2 |
| D134 | TGCTTCGAGCTC | (SEQ ID NO:105) | 1.8 | 0.8 | 1.8 | 1 | 17.7 | 24.8 | 9.1 | 5.7 |
| D136 | TGCACCGTTCTC | (SEQ ID NO:106) | 1.7 | 0.2 | 1.7 | 1 | 69.2 | 106.5 | 12.1 | 7.9 |
| CONTROL K ODN | | | | | | | | | | |
| DV89 | ACTCTTTCGTTGTC | (SEQ ID NO:83) | 1.6 | 1.6 | 19.7 | 23 | 169.1 | 419.7 | 6.7 | 7.2 |
| d112 | TGCAGGCTTCTC | (SEQ ID NO:6) | 16.0 | 28 | 20.4 | 32.6 | | | | |
| DV112 | TTGAGTGTTCTC | (SEQ ID NO:109) | 2.1 | 2.7 | 16.0 | 28 | 20.4 | 32.6 | 9.8 | 10.8 |
| DV112 | TTGAGTGTTCTC | (SEQ ID NO:109) | 2.1 | 2.7 | 16.0 | 28 | 20.4 | 32.6 | 9.8 | 10.8 |
| K41 | GTCGGCGCTGAC | (SEQ ID NO:120) | 5.7 | 7.4 | 13.3 | 8 | 29.1 | 24.7 | 8.8 | 5.7 |
| DV109 | TCGAGCGTTCT | (SEQ ID NO:4) | 3.4 | 4.0 | 11.3 | 9 | 28.4 | 46.4 | 14.5 | 12.6 |
| k10 | ATGCACTCTGCAGGCTTCTC | (SEQ ID NO:119) | 2.7 | 4.5 | 6.1 | 7 | 27.3 | 28.8 | 5.7 | 5.4 |
| K38 | GTCAGCGCTGAC | (SEQ ID NO:118) | 1.4 | 1.9 | 4.5 | 3 | 4.5 | 1.3 | 2.2 | 1.1 |
| k29 | TCGAGCG | (SEQ ID NO:112) | 19.7 | 25.9 | 4.2 | 5 | | | 2.8 | 3.6 |
| k26 | TCGAGCGTTC | (SEQ ID NO:45) | 6.6 | 4.9 | 4.1 | 1 | | | 22.3 | 24.4 |
| k27 | TCGAGCGTT | (SEQ ID NO:108) | 4.6 | 3.4 | 3.7 | 5 | | | 4.1 | 3.7 |
| K36 | GTCAACGCTGAC | (SEQ ID NO:107) | 2.2 | 3.3 | 3.4 | 2 | 8.6 | 2.0 | 5.5 | 2.8 |
| K35 | GTCAACGTCGAC | (SEQ ID NO:101) | 21.8 | 41.9 | 3.3 | 2 | 15.9 | 13.9 | 5.0 | 2.8 |
| K44 | GTCGACGCCGAC | (SEQ ID NO:97) | 4.1 | 6.0 | 3.0 | 2 | 9.4 | 6.3 | 2.6 | 1.2 |
| k28 | TCGAGCGT | (SEQ ID NO:91) | 21.5 | 26.2 | 2.9 | 3 | | | 6.7 | 9.1 |

TABLE 1-continued

| ODN | SEQUENCE | | IFN-g* | | IL-6* | | IgM* | | PROLIF* | |
|---|---|---|---|---|---|---|---|---|---|---|
| AA19 | GG<u>GGG</u>AACGTT<u>G</u>GGGG | (SEQ ID NO:87) | 9.4 | 14.6 | 2.2 | 1 | 4.7 | 4.5 | 1.5 | 0.5 |
| D135 | TGCAGCGAGCTC | (SEQ ID NO:85) | 1.4 | 0.5 | 1.8 | 2 | 4.3 | 6.6 | 3.4 | 1.5 |
| D141 | <u>CCG</u>AGGCTTCTC | (SEQ ID NO:82) | 1.3 | 0.4 | 1.7 | 2 | 53.7 | 99.0 | 12.8 | 9.0 |
| D126 | ACG<u>AGGTT</u>CTC | (SEQ ID NO:80) | 2.6 | 0.8 | 1.7 | 1 | 75.5 | 107.5 | 15.2 | 8.7 |
| K42 | GTCAACGCCGAC | (SEQ ID NO:78) | 2.6 | 3.1 | 1.7 | 1 | 5.7 | 5.3 | 4.3 | 3.7 |
| D140 | <u>GCG</u>AGGCTTCTC | (SEQ ID NO:77) | 1.2 | 0.5 | 1.5 | 1 | 56.7 | 85.4 | 10.9 | 7.0 |
| d121 | ACTCTTGAGTGTTCTC | (SEQ ID NO:66) | 3.6 | 6.2 | 1.0 | 1 | 10.2 | 18.5 | 17.3 | 44.5 |
| K45 | GTCGGCGCCGAC | (SEQ ID NO:57) | 5.7 | 6.6 | 0.4 | 1 | 18.3 | 22.1 | 10.1 | 4.3 |
| K43 | GTCAGCGCCGAC | (SEQ ID NO:56) | 2.1 | 1.6 | 0.3 | 1 | 6.9 | 8.6 | 5.1 | 5.7 |
| K24 | CGAGCGTTCTC | (SEQ ID NO:48) | 4.9 | 5.1 | 0.1 | 0 | 0.7 | 1.0 | 1.0 | 0.1 |

Underlined bases are phosphodiester.
* indicates methylated CG. Bold indicates self-complementary sequences.
Sequence identifier is noted below the nucleic acid sequence.
For each heading (IFN-g, IL-6, IgM, PROLIF (proliferation)) first column is average and second column is standard deviation.

The foregoing data demonstrates the induction of an immune response in human cells, as exemplified by PBMC. Specifically, the results demonstrate that K type oligodeoxynucleotides induce IL-6, cell proliferation and a humoral response, while D type oligodeoxynucleotides induce the production of IFN-γ.

Example 2

Production of IL-6

The following example demonstrates induction of an immune response, as measured by cytokine production, by K type oligodeoxynucleotides. Specifically, it is demonstrated that production of the cytokine IL-6 can be induced by K type oligodeoxynucleotides, and that B cells are stimulated by K type oligodeoxynucleotides.

A human B cell line (RPMI 8226) was maintained according to the manufacturers recommendations. ODNs were synthesized as described in Example 1. In some ODNs, the normal DNA phosphodiesterase linkages were replaced with phosphorothioate linkages, as described in Example 1. To reduce degradation of the ODNs, those that did not have an entire phosphorothioate backbone contained phosphorothioate linkages at the ends. The cells were incubated with various ODNs for 14 hrs. IL-6 production was determined by ELISA using anti-IL-6 antibodies, as described in Example 1.

IL-6 levels are set forth in Table 1. These data confirm that a sequence containing 5' $N_1N_2N_3$T-CpG-W$N_4N_5N_6$ 3', which are linked by phosphorothioate bonds and wherein the central CpG motif is unmethylated, W is A or T, and $N_1$, $N_2$, $N_3$, $N_4$, $N_5$, and $N_6$ are any nucleotides, is desirable to induce a humoral immune response.

The foregoing data demonstrates the induction of an immune response in human cells by K type oligodeoxynucleotides, as exemplified by the human B cell line RPMI 8226, and as measured by production of the cytokine IL-6.

Example 3

Exemplary Material and Methods

The following example delineates material and methods that were used to investigate the induction of an immune response by D-type ODNs. Exemplary D type ODNs are shown in Table 2 below.

TABLE 2

| | | IFNq | |
|---|---|---|---|
| ODN | | AVG | SD |
| Media | | 0.9 | 0.8 |
| DV104 | GG<u>TGCATCGATGCAG</u>GGGG (SEQ ID NO:1) | 47.7 | 64.7 |
| DV19 | GG<u>TGCATCGATGCAG</u>GGGG (SEQ ID NO:1) | 44.0 | 71.8 |
| DV29 | GG<u>TGCACCGGTGCAG</u>GGGG (SEQ ID NO:2) | 35.9 | 38.9 |
| DV35 | GG<u>TGCATCGATGCAG</u>GGGG (SEQ ID NO:1) | 33.3 | 63.6 |
| DV28 | GG<u>TGCGTCGATGCAG</u>GGGG (SEQ ID NO:7) | 32.2 | 45.3 |
| DV106 | GG<u>TGTGTCGATGCAG</u>GGGG (SEQ ID NO:26) | 29.9 | 71.4 |
| DV116 | TG<u>CATCGATGCAG</u>GGGG (SEQ ID NO:12) | 25.1 | 28.9 |
| DV113 | GG<u>TGCATCGATACAG</u>GGGG (SEQ ID NO:11) | 21.1 | 15.3 |
| DV34 | GG<u>TGCATCGATGCAG</u>GGGG (SEQ ID NO:1) | 16.2 | 19.1 |
| DV102 | GG<u>TGCATCGTTGCAG</u>GGGG (SEQ ID NO:30) | 15.8 | 39.4 |
| DV32 | GG<u>TGCGTCGACGCAG</u>GGGG (SEQ ID NO:31) | 14.5 | 18.0 |
| DV117 | GG<u>TCGATCGATGCAC</u>GGGG (SEQ ID NO:32) | 13.4 | 14.6 |
| dv37 | GGTGC<u>ATCGAT</u>GCAGGGGG (SEQ ID NO:1) | 13.0 | 19.6 |

TABLE 2-continued

| ODN | | IFNq | |
|---|---|---|---|
| | | AVG | SD |
| DV25 | GGTGCATCGATGCAGGGGGG (SEQ ID NO:1) | 12.2 | 7.9 |
| DV30 | GGTGCATCGACGCAGGGGGG (SEQ ID NO:35) | 11.3 | 8.1 |
| dv120 | GGTGCATCGATAGGCGGGGG (SEQ ID NO:36) | 8.7 | 11.5 |
| DV27 | GGTGCACCGATGCAGGGGGG (SEQ ID NO:37) | 8.5 | 7.3 |
| dv119 | CCTGCATCGATGCAGGGGGG (SEQ ID NO:38) | 7.5 | 9.1 |
| D142 | GGTATATCGATATAGGGGGG (SEQ ID NO:39) | 7.3 | 1.1 |
| d143 | GGTGGAT*C*GATCCAGGGGGG (SEQ ID NO:40) | 6.4 | 4.5 |

UNDERLINED = PHOSPHODIESTER; *METHYLATED C

Normal PBMC were obtained from the National Institutes of Health Department of Transfusion Medicine (Bethesda, Md.). The human myeloma cell line RPMI 8226 (CCL-155; American Type Culture Collection, Manassas, Va.) and the NK-92 human NK cell line (a kind gift of Dr. J. Ortaldo, National Cancer Institute, Frederick, Md.) were grown in RPMI 1640 supplemented with 10% FCS, penicillin/streptomycin, L-glutamine, HEPES, sodium pyruvate, and 2-ME in a 5% $CO_2$ in-air incubator. Medium for NK-92 cells was supplemented with IL-2 (200 IU/ml; R&D Systems, Minneapolis, Minn.) and IL-15 (15 ng/ml; Endogen, Boston, Mass.).

Oligodeoxynucleotides

ODN were synthesized at the Center for Biologics Evaluation and Research core facility. All had <0.1 endotoxin U/ml endotoxin at ODN concentrations of 1 mg/ml.

Antibodies

Abs against human IFN-g (Endogen), IL-6 (R&D Systems), and IgM (Se-rotec, Oxford, U.K.) were used for ELISA and enzyme-linked immunospot (ELISPOT) assays. FITC- and/or CyChrome-labeled Abs against human CD3, CD4, CD14, CD11c, CD16, CD56, CD83, HLA-DR, IL-6, and IFN-γ were obtained from BD PharMingen (San Diego, Calif.) or BD Bio-sciences (San Jose, Calif.) and used as recommended by the manufacturer. Neutralizing Abs to IL-12 were obtained from R&D Systems, and Abs to IL-18 were kindly provided by Dr. Howard Young (National Cancer Institute).

Mononuclear Cell Preparation

Mononuclear cells were separated by density gradient centrifugation over Ficoll-Hypaque as described (17). Cells were washed three times and cultured in RPMI 1640 medium supplemented with 10% heat-inactivated FCS for 72 h at 53 10 5 cells/well in the presence of 1–3 mM ODN.

ELISA and ELISPOT Assays

Ninety-six-well microtiter plates (Millipore, Bedford, Mass.) were coated with anti-cytokine Ab or anti-IgM and blocked with PBS-5% BSA (17,18). Cytokines and Ig in culture sups or secreted by individual cells were detected colorimetrically using biotin-labeled Abs followed by phosphatase conjugated avidin and then phosphatase-specific colorimetric substrate. Standard curves were generated to quantitate ELISA results using known amounts of recombinant cytokine or purified IgM. The detection limit of the assays was: 6 pg/ml for IFN-g, 20 pg/ml for IL-6, and 10 ng/ml for IgM. Stimulation index was calculated by the formula: (value for stimulated cells 2 background)/(value for unstimulated cells 2 background). In cases where cytokine/Ig production was below assay sensitivity, the lower limit of detection was used to calculate the stimulation indices. All assays were performed in triplicate.

Proliferation Assays

A total of 10 5 PBMC/well were incubated with 3 mM of ODN for 68 h, pulsed with 1 mCi of [$^3$H]thymidine, and then harvested 4 h later. The proliferation index represents the fold difference between stimulated and unstimulated cells. All assays were performed in triplicate.

Intracellular Cytokine Staining and Flow Cytometry

PBMC were cultured for 8 h (K type) or 24 h (D type) with 3 mM of various ODN. Brefeldin A (20 mg/ml) was added to the cultures after 2 or 12 h, respectively. Cells were harvested with warm PBS-0.02% EDTA and washed. PBMC (1 3 10 6/sample) were fixed and permeabilized using the Fix & Perm cell permeabilization kit (Caltag, Burlingame, Calif.) as recommended by the manufacturer. Cells were then stained with PE-conjugated anti-IL-6 or anti-IFN g plus specified FITC- or Cy Chrome-conjugated Abs against cell surface markers for 30 min in darkness. After labeling, the cells were washed twice, and 40,000 events per sample were analyzed by FAC-Scan flow cytometry (BD Biosciences). Cell Quest software (BD Bio-sciences) was used for data analysis.

Statistical Analysis

Statistically significant differences were determined using a two-tail non-parametric Mann-Whitney U test and non-parametric ANOVA.

Example 4

Response of Human Peripheral Blood Mononuclear Cells (PBMC) to CpG ODN

Response of human PBMC to CpG ODN Novel ODN were studied for their ability to stimulate human PBMC to proliferate and/or secrete Ig or cytokines. As shown in FIG. 1, two structurally distinct ODN classes were identified that stimulated PBMC from 0.95% of the donors. Those of the K type stimulated significantly greater cell proliferation ($p<0.0001$) and induced higher levels of IL-6 (240 vs 85 pg/ml; $p<0.01$) and IgM(695 vs 20 ng/ml; $p<0.0001$) than D ODN. In contrast, D ODN were stronger inducers of IFN-g (70 vs 13 pg/ml; $p<0.05$). FIG. 1 illustrates the response of PBMC to K and D ODN.

Type D ODN

Modifications were introduced in various regions of D ODN to identify the critical sequences and structures that account for the ability of these ODN to induce IFN-γ. To standardize results from the large number of subjects and experiments included in the analysis, the magnitude of each response is presented as fold increase over cells from the same subject incubated in medium alone. The general magnitude of these responses was comparable to that shown in FIG. 1.

FIG. 2 illustrates the parameters governing D ODN induced immune activation. All D-type ODNs contain an unmethylated CpG dinucleotide (FIG. 2). Inversion, replacement, or methylation of the CpG reduces or abrogates reactivity (FIG. 2A, line 1 vs lines 2–6, and line 7 vs line 8;

p<0.0001). In addition, the results demonstrate that D ODN are stimulatory only if the CpG dinucleotide and its immediate flanking regions are composed of phosphodiester (shown in gray) rather than phosphorothioate nucleotides (FIG. 2B, line 1 vs line 2; p<0.001). Because phosphorothioate-modified nucleotides confer resistance to exonuclease digestion, they are incorporated at the ends of the ODN to improve activity (FIG. 2B, lines 1 and 5 versus lines 3 and 4; p<0.07). Unless otherwise stated, all D ODN studied were phosphorothioate/phosphodiester chimeras.

As shown in FIG. 2, the level of immune stimulation induced by D ODN was demonstrated to be influenced by the bases flanking the CpG dinucleotide. Self-complementary hexamers consisting of a Pu Py CG Pu Py were the most active, as exemplified by ATCGAT and ACCGGT (FIG. 2C, lines 1 and 2). Substituting a Pu for a Py, or vice versa, significantly reduced or eliminated ODN activity (circled nucleotides in FIG. 2C, lines 1 and 2 vs lines 6–13; p<0.0001. By comparison, hexamers that maintained the PuPyCGPuPy sequence, but are non self-complementary induced lower levels of IFN-g production (FIG. 2C, lines 1 and 2 vs lines 3–5; p<0.001). Sequential deletion experiments showed that the minimum length of an active D ODN is 16 bp (FIG. 2D; p<0.01). This finding suggested that sequences outside the central hexamer might influence D ODN activity.

Indeed, stimulation was maximal when the three bases on each side of the CpG-containing hexamer formed a self-complementary sequence (FIG. 2E, lines 1 and 2 versus lines 3 and 4; p<0.0001). Without being bound by theory, computer modeling of D ODN suggested that these self-complementary base sequences help form a stem-loop structure with the CpGdi nucleotide at the apex at 37° C. The ends of the ODN also contribute to its activity, with the inclusion of more than four Gs at the 39 end significantly increased function (FIG. 2F, lines 1–3 versus lines 4 and 5; p<0.001). Thus, modifications in any of the three areas (the central hexamer, the region flanking the hexamer, or the poly G tail) can be used to influence ODN activity.

Type K ODN

K ODN trigger cell proliferation and the secretion of IgM and IL-6, but little IFN-g (see Table 1 and FIG. 1). These ODN have a phosphorothioate backbone and at least one unmethylated CpG dinucleotide.

TABLE 5

Rules Governing K ODN Induced Immune Activation

| | | Stimulation Index | | | | |
|---|---|---|---|---|---|---|
| | | IL-6 | | Proliferation | | IgM |
| Assay Subject #: | | 1 | 2 | 1 | 2 | 1 | 2 |
| A. Multiple CpGs induce more stimulation | | | | | | | |
| 1 ATCGACTCTCGAGCGTTCTC | (SEQ ID NO:3) | 50 | 57 | 13 | 30 | 138 | 71 |
| 2 TCGAGCGTTCTC | (SEQ ID NO:79) | 35 | 40 | 15 | 37 | 19 | 79 |
| 3 TCGAGGCTTCTC | (SEQ ID NO:75) | 28 | 12 | 8 | 25 | 8 | 22 |
| 4 TGCAGGCTTCTC | (SEQ ID NO:6) | 1 | 0 | 5 | 7 | 5 | 4 |
| B. Minimum size of stimulatory "K" ODN | | | | | | | |
| 1 TCGACTCTCGAGCGTTCTC | (SEQ ID NO:8) | 20 | 23 | 37 | 72 | >100 | 100 |
| 2 ACTCTCGAGCGTTCTC | (SEQ ID NO:9) | 20 | 18 | 30 | 46 | >100 | 100 |
| 3 TCTCGAGCGTTCTC | (SEQ ID NO:72) | 16 | 40 | 28 | 41 | >100 | 100 |
| 4 TCGAGCGTTCTC | (SEQ ID NO:79) | 23 | 15 | 13 | 25 | >100 | 80 |
| 5 CTCGAGCGTTCT | (SEQ ID NO:10) | 21 | 14 | 16 | 21 | 95 | 92 |
| 6 TCGAGCGTTCT | (SEQ ID NO:4) | 10 | 4 | 15 | 35 | 45 | 78 |
| 7 TCGAGCGTTC | (SEQ ID NO:116) | 6 | 5 | 17 | 40 | 35 | 82 |
| 8 TCGAGCGTT | (SEQ ID NO:117) | 1 | 7 | 5 | 7 | 32 | 25 |
| 9 TCGAGCGT | (SEQ ID NO:91) | 1 | 5 | 1 | 13 | 25 | 12 |
| 10 TCGAGCG | (SEQ ID NO:115) | 1 | 1 | 1 | 5 | 9 | 4 |
| C: CpG motifs located at the 5' end of the ODN are most stimulatory | | | | | | | |
| 1 TCGAGCGTTCTC | (SEQ ID NO:79) | 12 | 40 | 52 | 59 | 80 | >100 |
| 2 TCGAGGCTTCTC | (SEQ ID NO:75) | 6 | 12 | 51 | 61 | >100 | >100 |
| 3 TGCTTCGAGCTC | (SEQ ID NO:105) | 4 | 3 | 12 | 16 | 20 | 60 |
| 4 GCGAGGCTTCTC | (SEQ ID NO:121) | 5 | 12 | 18 | 14 | >100 | >100 |

TABLE 5-continued

Rules Governing K ODN Induced Immune Activation

| | | | Stimulation Index | | | | |
|---|---|---|---|---|---|---|---|
| | | | IL-6 | | Proliferation | | IgM |
| Assay Subject #: | | | 1 | 2 | 1 | 2 | 1 | 2 |

| | | | | | | | | |
|---|---|---|---|---|---|---|---|---|
| 5 | TGCAGCGAGCTC | (SEQ ID NO:85) | 5 | 2 | 4 | 4 | 1 | 16 |
| 6 | CGAGCGTTCTC | (SEQ ID NO:48) | <1 | <1 | 1 | 1 | <1 | 2 |

D. Optimization of the 5' CpG flanking region

| | | | | | | | | |
|---|---|---|---|---|---|---|---|---|
| 1 | TCGATGCTTCTC | (SEQ ID NO:95) | 5 | 12 | 60 | 67 | 100 | 9 |
| 2 | TCGAGGCTTCTC | (SEQ ID NO:75) | 6 | 12 | 51 | 61 | 160 | 5 |
| 3 | ACGAGGCTTCTC | (SEQ ID NO:34) | 3 | 3 | 18 | 23 | 110 | 11 |
| 4 | GCGAGGCTTCTC | (SEQ ID NO:127) | 3 | 1 | 18 | 14 | 72 | 6 |
| 5 | CCGAGGCTTCTC | (SEQ ID NO:82) | 4 | 1 | 15 | 25 | 25 | 7 |
| 6 | TGCTTCGAGCTC | (SEQ ID NO:105) | 3 | 1 | 12 | 16 | 60 | 40 |
| 7 | TGCAGCGAGCTC | (SEQ ID NO:82) | 2 | 1 | 4 | 4 | 16 | 8 |

E. Optimization of the 3' CpG flanking region

| | | | | | | | | |
|---|---|---|---|---|---|---|---|---|
| 1 | TCGTTTGTTCTC | (SEQ ID NO:93) | 8 | 8 | 28 | 31 | >100 | >100 |
| 2 | TCGTATGTACTC | (SEQ ID NO:33) | 8 | 8 | 26 | 32 | 2 | 33 |
| 3 | TCGGATGAGCTC | (SEQ ID NO:29) | 6 | 8 | 9 | 20 | 28 | 41 |
| 4 | TCGAATGCTCTC | (SEQ ID NO:28) | 3 | 5 | 14 | 22 | 6 | 14 |
| 5 | TTGTTCGTTCTC | (SEQ ID NO:27) | 3 | 4 | 15 | 14 | 19 | 26 |
| 6 | TTGTTCGTACTC | (SEQ ID NO:25) | 2 | 4 | 14 | 13 | 15 | 72 |
| 7 | TTGTTCGAGCTC | (SEQ ID NO:24) | 2 | 4 | 6 | 4 | 6 | 16 |
| 8 | TTGTTCGAACTC | (SEQ ID NO:24) | 2 | 2 | 11 | 5 | 1 | 1 |

Over 200 novel ODN were synthesized, and their ability to activate PBMC from multiple donors examined. PBMC were stimulated for 72 hours in the presence of ODN (1 μM added at time 0). Cytokine and antibody secretion in the supernatants were assessed by ELISA, while proliferation was determined by [H]$^3$ uptake. Examples of general findings are presented in this Table. Results are expressed as fold increase over unstimulated cells.

As with D ODN, eliminating the CpG dinucleotide from a K type ODN significantly reduced immune activation (Table 3A, line 3 versus line 4; p, 0.02). Incorporating multiple CpGs in a single ODN increased immune stimulation (Table 3A, lines 1–3). To determine the minimum length of a stimulatory K ODN, nucleotides were sequentially deleted from each end. ODN at least 12 bases long consistently induced strong immune cell activation, whereas shorter ODN were relatively less active (Table IB, lines 1–5 vs lines 6–10). CpG motifs at the 5' end were the most stimulatory (Table 3C, line 2 vs line 3 and line 4 vs line 5), although at least one base upstream of the CpG was required (Table 3C, line 1 vs line 6). Indeed, a thymidine in the immediate 5' position (Table 3D, lines 1 and 2 vs lines 3–5 and line 6 vs line 7) and a 3' TpT or a TpA (Table 3E, lines 1 and 2 vs lines 3 and 4 and lines 5 and 6 vs line 7) yielded the most active K ODN. Modifications >2 bp from the CpG dinucleotide had relatively less effect on ODN activity.

Example 5

Cellular Targets of K and D ODN

The phenotype of the cells stimulated to produce cytokine was determined by combined cell surface and intracytoplasmic staining. As seen in Table 4, D ODN selectively stimulated CD3−CD16+CD56+CD14-cells to produce IFN-γ, consistent with the direct activation of NK cells.

TABLE 4

Phenotype of PBMC stimulated by CpG ODN to secrete cytokines

A. Phenotype of PBMC activated by "D" ODN to produce IFNγ

| Cell surface marker | % positive cells |
|---|---|
| CD16 | 91 |
| CD56 | 99 |
| CD3 | 5 |
| CD24 | <1 |

B. Phenotype of PBMC activated by "K" ODN to produce IL-6

| Cell surface marker | % positive cells |
|---|---|
| CD83 | 93 |

TABLE 4-continued

Phenotype of PBMC stimulated by CpG ODN to secrete cytokines

| | |
|---|---|
| CD14 | 70 |
| CD11c | 69 |
| CD19 | 13 |
| CD16 | <1 |

Freshly isolated PBMC were stimulated with K" (8 hr) or D (24 hr) ODN. Cells were fixed, permeabilized and stained with PE-anti-IL-6 or anti-IFNγ. Results are representative of 4–10 experiments.

Without being bound by theory, the effect appears to be direct because D ODN do not induce a significant increase in IL-12 secretion. Moreover, studies using neutralizing anti-IL-12, which reduce the production of IFN-g by PBMCs stimulated with PHA (44% p, 0.05) or with bacillus Calmette-Guerin (77%; p, 0.05), did not decrease the IFN-γ production induced by CpG-ODN. By comparison, K ODN stimulated CD14+, CD11c+, and CD83+ cells to produce IL-6, indicating that they were of monocyte/dendritic cell lineage (Table 4B). K ODN also stimulated a fraction of CD19+ B cells to release IL-6.

To confirm these findings, human NK, T, and B cell lines were tested for their responsiveness to K and D ODN. The NK-92 cell line responded exclusively to D ODN by secreting IFN-γ, whereas the human RPMI 8226 B cell line was stimulated by K ODN to release IL-6. Non-CpG ODN did not stimulate either cell line.

Thus, as disclosed herein, there are two structurally distinct types of CpG ODN that stimulate different cellular elements of the immune system to mount divergent responses. K type ODN induce monocytes/dendritic cells to produce IL-6 and B cells to proliferate and secrete IgM, whereas D type ODN support NK production of IFN-γ (see Table 1). These CpG ODN can be used as vaccine adjuvants, anti-allergens, and immunoprotective agents, as disclosed herein.

The CpG motifs at the center of K and D ODN differ. The optimal K motif contains a thymidine immediately 5' of the CpG, and a TpT or TpA 3' of the CpG. By comparison, optimally active D type ODN contain Pu-Py dimers on each side of the CpG. D ODN also are longer. In one embodiment, the CpG flanking regions are self-complementary. Two dimensional computer modeling further suggested that this self-complementary sequence facilitates the formation of a hairpin loop that exposes the CpG at the apex. Without being bound by theory, this stem-loop structure contributes to the recognition of D ODN because IFN-γ production declines when the length or binding strength of the palindrome is reduced (FIG. 2E). Without being bound by theory, the inclusion of poly G at the 3' end of the ODN likely further confers a structural benefit. Alternatively, the poly Gs may improve the efficiency of cellular uptake.

As demonstrated herein, K and D ODNs activate distinct cell types. K ODN activate monocytes and B cells to secrete IL-6, whereas D type ODN stimulate NK cells to secrete IFN-γ (Table 1). It is believed that this difference is not due to differential uptake of the ODNs, as monocytes and NK cells take up both D and K ODNs. Without being bound by theory, K and D type ODNs activate their target cells directly, as 1) CpG ODN stimulate cloned cell lines to secrete cytokines; 2) cytokine mRNA appears within minutes of ODN stimulation; and 3) ELISPOT studies show that the CpG ODN induced rapid increase (two to five-fold) in IL-6 and IFN-γ secreting PBMC (5 and 18 hour after stimulation, respectively). Moreover, flow cytometric analysis of cells stimulated to secrete IFN-γ by CpG ODN were CD3– even after 72 h of stimulation, indicating that the increased IFN-γ in supernatents is not due to the secondary activation of T cells.

Example 6

Further Evidence of Differing Functions of D and K ODNs

Material and Methods

Oligonucleotides and antibodies: ODN were synthesized at the CBER core facility. Sequences of the CpG ODN used in this study are: 5'-T<u>CGAGCG</u>TTCTC-3' (K23, SEQ ID NO: 79) and 5'-GGtgcat<u>cg</u>atgcagggGG-3' (D35, SEQ ID NO: 1). The control for K ODN was: 5'-TCAAGTGTTCTC-3' (SEQ ID NO: 122) and for D ODN was: 5'-GgtgcatctatgcaggggGG-3' (SEQ ID NO: 123). In this example, bases shown in capital letters are phosphorothioate while those in lower case are phosphodiester. CpG dinucleotides are underlined. All FITC, PE and cychrome labeled Mabs were purchased from Pharmingen (San Jose, Calif.). All ODNs used in this study contained <0.1 U/mg of endotoxin.

Cell cultures: PBMC from normal donors (provided by the NIH Department of Transfusion Medicine) were isolated by Ficoll-Hypaque density gradient centrifugation (Verthelyi, D, et al., J. Immunol. 166:2372–2377, 2000). Countercurrent centrifugal elutriation was used to isolate monocytes that were >95% pure. $0.5-4 \times 10^6$ cells/ml were cultured in RPMI 1640 containing 5% FCS, 50 U/ml penicillin, 50 μg/ml streptomycin, 0.3 mg/mL L-glutamine, 0.1 mM non-essential amino acids, 1 mM sodium pyruvate, 10 mM HEPES and $10^{-5}$ M 2-mercaptoethanol. Cells were stimulated with ODN for 8–72 h with 1–3 μM ODN, depending upon the assay.

Analysis of cell proliferation: PBMC were cultured in complete medium plus 3 μM ODN for 72 h. To study B cell proliferation, cells were loaded with 10 nM of CFSE (Molecular Probes Inc., Eugene, Oreg.) as described before (24). Proliferation of CD11c+ monocytes was monitored by adding 10 μM of BrdU (Pharmingen, San Jose, Calif.) for the last 18 h of culture. Staining for BrdU was performed as recommended by the manufacturers.

ELISA assays: 96-well microtiter plates (Millipore, Bedford, Mass.) were coated with anti-cytokine or anti-IgM Ab and blocked with PBS-5% BSA (8). The plates were incubated for 2 h with culture supernatants from PBMC ($5 \times 10^5$/ml) that had been stimulated for 8–24 h with ODN as described above. IL-6, IFNγ and IgM were detected colorimetrically using biotin-labeled antibodies followed by phosphatase-conjugated avidin and a phosphatase specific colorimetric substrate (Verthelyi, D, et al., J. Immunol. 166:2372–2377, 2000). The detection limit of the assays was: 6 pg/ml for IFNγ, 20 pg/ml for IL-6, and 10 ng/ml for IgM. All assays were performed in triplicate.

Staining for cell surface markers and Intracellular cytokine: Cultured cells were washed in cold PBS, fixed, and stained with fluorescent labeled anti-CD69 (24 h), anti-CD25 (72 h), anti-CD83 (72 h) or anti-CD86 (72 h). To detect intracytoplasmic cytokine, cells incubated with ODN for 8 h were washed, fixed, permeabilized (as per manufacturer's instructions, Caltag, Calif.) and stained with 4 μg/ml PE-conjugated anti-IL-6 or 2 μg/ml PE-conjugated anti-IFNγ (Pharmingen, San Jose, Calif.) plus various FITC and Cy-Chrome labeled surface markers for 30' at RT. Samples were washed and analyzed (20,000–40,000 events) on a FACScan flow cytometer (Becton Dickinson, San Jose, Calif.) after gating on live cells with proper electronic compensation. The data were analyzed using CELLQuest software (Becton Dickinson Immunocytometry Systems, San Jose, Calif.).

Analysis of cell-surface binding and internalization of ODN: PBMC ($4 \times 10^6$/ml) were incubated with biotinylated ODN (1–3 μM) for 10' at 4° C. (binding experiments) or 37° C. for 1 h (uptake experiments). To detect internalized ODN, surface bound ODN was blocked with 100 μg/ml of "cold" streptavidin. After washing, these cells were permeabilized, fixed, and stained with PE-conjugated streptavidin (1 μg/ml) plus FITC or Cy-Chrome conjugated cell surface markers.

Confocal Microscopy Elutriated monocytes ($4 \times 10^6$/ml) were incubated with Cy-3 or FITC labeled K and/or D ODN at 37° C. for 1 h. The cells were washed, and mounted using the Prolong antifade kit (Molecular Probes, Oregon, USA). Subcellular localization of Cy3 and FITC labeled ODN was determined by confocal microscopy under 1000× magnification (LSM5 PASCAL, Carl Zeiss In., Thornwood, N.Y.).

Binding and Internalization of CpG ODN.

The ability of human PBMC to bind and internalize CpG ODN was examined using fluorescent-labeled K23 and D35 ODN. Both types of ODN bound rapidly to the surface of virtually all human monocytes at 4° C. A significant fraction of B lymphocytes (20–45%) and NK cells (~10–20%) also bound these ODN. Simultaneous staining with K and D ODN showed that the same cells were binding both types of ODN. In contrast, interaction with T cells barely exceeded background levels.

To monitor internalization, PBMC were incubated with biotin-labeled ODN for 60' at 37° C. Surface-bound ODN was blocked with excess strepavidin, and internalized ODN detected by staining fixed, permeabilized cells with FITC-avidin. The fraction of monocytes, B lymphocytes and NK cells that internalized K23 and D35 ODN was similar to the fraction of each cell type that bound these ODN. Similar results were obtained using other D and K ODN. No internalization was observed when cells were incubated with ODN for 10' at 4° C., suggesting that ODN uptake involves metabolic activity.

The ratio of membrane bound: internalized ODN was compared. Based on differences in mean fluorescence intensity, it was calculated that target cells internalized approximately half of the ODN that had bound to their cell surface. For all cell types, the absolute magnitude of D ODN uptake exceeded that of K ODN. For example, the amount of labeled D ODN that bound to and was taken up by monocytes exceeded that of equimolar K ODN by ~2-fold throughout the functional concentration range of these agents ($p<0.001$). To achieve equivalent levels of binding and uptake required that "D" ODN be used at a 4-fold lower concentration than K (e.g. 0.75 vs 3.0 μM).

The intracellular localization of these two types of ODN was examined by confocal microscopy of labeled monocytes. K and D ODN largely occupied discrete areas within the same cell, although there was a limited degree of co-localization. D ODN largely occupied punctuated vesicles, whereas K ODN were more diffusely distributed, staining the nucleus as well as cytoplasmic vesicles. This difference in localization was associated with the presence or absence of a poly G tail, since control (non-CpG) ODN with a poly G tail showed the same distribution pattern as did D ODN. In contrast, the fluorescent dyes used did not influence distribution, since switching dyes had no effect on ODN localization pattern.

Differential Effect of K Versus D ODN on B Cell Function

Whole PBMC were treated with optimal concentrations of K23 and D35 ODN. K ODN rapidly activated CD19$^+$ B cells, reflected by a significant increase in the expression of the CD69 early activation marker and the CD25 late activation marker ($p<0.001$). K ODN also triggered a >10-fold increase in B cell proliferation ($p<0.05$), a >10-fold increase in IgM production ($p<0.01$), and a 5-fold increase in the number of B cells secreting IL-6 ($p<0.001$). The effect of K23 exceeded that of D35 (and of a control for the K type ODN of the same structure but lacking the critical CpG motif) by >10-fold in each of these functional assays. D ODN were not entirely inactive, however, since they induced a modest increase in CD25 and CD69 expression by CD19$^+$ B cells.

Differential Effect of K Versus D ODN on NK Cells

NK cells were identified by their expression of the CD16 surface marker. D ODN stimulated approximately 25% of these cells to increase expression of CD25 and CD69 ($p<0.001$). Consistent with previous studies, D ODN also triggered a significant increase in IFNγ secretion by NK cells ($p<0.05$). By comparison, neither K ODN nor a non-CpG control for the D ODN significantly stimulated IFNγ production (see also Table 1). K23 did induce a modest increase in the number of NK cells expressing CD25 and CD69 ($p<0.05$). None of these ODN induced NK cells to proliferate.

Differential Effect of K Versus D ODN on Monocytes

K and D ODN had disparate effects on purified monocytes. K23 stimulated CD14$^+$ monocytes to proliferate ($p<0.05$) and secrete IL-6 ($p<0.001$), while D35 had no effect in these assays (Table 5). Instead, D (but not K) ODN stimulated monocytes to mature into CD83$^+$/CD86$^+$ dendritic cells (DC) ($p<0.001$, Table 5). The divergent effects of K versus D ODN on monocytes persisted throughout the physiologic concentration range of both types of ODN, and was observed using a variety of D and K ODN, indicating that these differences were not due to variation in ODN binding or uptake. Although both types of ODN increased CD69 and CD25 expression, D ODN up-regulated these activation markers in monocytes significantly more effectively ($p<0.001$, Table 5).

TABLE 5

Effects of D ODN
% of Cells Expressing/Producing

| ODN type | CD25 | CD 69 | IL-6 | L-6 (ng/ml) | Proliferation (SI) | DC maturation |
|---|---|---|---|---|---|---|
| K23 | 32.8 ± 1.1 | 39.7 ± 5.3 | 24.1 ± 2.4 | 2.0 ± 0.3 | 7.0 ± 1.4 | 3.5 ± 0.3 |
| D35 | 48.6 ± 7.5 | 82.1 ± 2.4 | 4.6 ± 0.3 | 0.8 ± 0.1 | 1.0 ± 0.5 | 23.7 ± 2.0 |
| K23 + D35 | 44.7 ± 13.9 | 53.8 ± 12.5 | ND | 2.2 ± 0.1 | 2.8 ± 1.7 | 5.2 ± 0.8 |
| "K" control | 21.8 ± 2.2 | 30.2 ± 2.5 | 5.1 ± 0.6 | <.03 | 2.1 ± 1.6 | 1.8 ± 0.1 |

PBMC or elutriated monocytes were stimulated with 3 uM of ODN for 8–72 h. The percent of $CD14^+$ monocytes induced to secrete IL-6 was determined by intracytoplasmic staining. Due to the down-regulation of CD14, CD11c was used to monitor the expression of CD25 and CD69 by stimulated cells. The percent of $CD83^+/CD86^+$ dendritic cells in culture was determined after 72 h. IL-6 levels in culture supernatants were determined by ELISA, while proliferation was evaluated BrDU incorporation. Results represent the mean ± SD of 5 independent experiments.

Competition Between K and D ODN at the Single Cell Level

The above findings suggested that monocytes responded differently to stimulation by K versus D ODN. There are two possible explanations for this observation: either i) these two types of ODN were triggering the same cells to mount distinct types of immune response or ii) K and D ODN were acting on different subpopulations of monocytes. The latter explanation seemed unlikely, given that confocal microscopy showed that the same cells were binding and internalizing both types of ODN.

To clarify this situation, monocytes were treated simultaneously with D35 plus K23. At optimally stimulatory concentrations, these ODN did not cross-compete for uptake or binding. Yet when their function was analyzed, co-administration of K ODN reduced the ability of D ODN to trigger monocyte differentiation by 70% (p<0.001). The inhibitory effect of K ODN on the activity of D ODN was sequence specific and concentration dependent, since control non-CpG ODN did not significantly interfere with the activity of D ODN. Conversely, D ODN significantly reduced the ability of K ODN to induce monocytes to proliferate (p<0.05). As above, the inhibitory effect of D on the activity of K ODN was sequence specific and concentration dependent.

A very different pattern emerged when B and NK cells were studied. In these cells, the co-administration of D with K ODN was not inhibitory. Rather, the ability of K ODN to stimulate B cells to proliferate and secrete IL-6 and IgM was unaffected by the presence of D ODN, and the ability of D ODN to stimulate NK cells to secrete IFNγ was not reduced by inclusion of K ODN.

Example 7

D ODN Enhance Tumor Lysis

Reports of tumor regression following systemic bacterial infection stimulated research into immune adjuvants as a strategy for tumor treatment. Immunostimulatory oligodeoxynucleotides (ODNs) containing the CpG motif have been demonstrated to induce the production of various cytokines, natural killer cells, monocytes, lymphocytes and dendritic cells (see above). Thus, short-term bladder transitional cell carcinoma (TCC) cultures were treated with CpG ODN immunostimulated PBMC and the cultures were analyzed for evidence of tumor lysis.

Materials and Methods

Papillary TCCs from 4 patients were cultured. Peripheral blood mononuclear cells (PBMCs) were obtained from each patient. In matched cultures, the tumor cells were treated with PBMCs stimulated in-vitro with: 1) CpG ODN in the presence or and absence of tumor cells, 2) bacillus Calmette-Guerin (BCG) stimulated PBMCs (positive control and standard of care), 3) unstimulated PBMCs, and/or 4) BCG or CpG ODN in the absence of the patient's PBMCs (negative controls).

The morphologic and lytic characteristics of these cultures were compared with those of untreated matched tumor cell cultures. A chromium based CTL assay method was used for quantitative comparison of tumor lysis.

Results

PBMCs that were stimulated in vitro with CpG ODN type D in the presence of tumor cells lysed 30–70% of the tumor cells from 3 of 4 patients.

TABLE 6

| | Percent lysis |
|---|---|
| PBMC + TCC | 4 + 5 |
| PBMC + TCC + D ODN | 41 + 15 |
| PBMC + TCC + K ODN | 3 + 3 |
| PBMC + TCC + CONTROL ODN | 3 + 2 |
| PBMC + TCC + BCG | 71 + 24 |

Thus, CpG ODN immunostimulation was associated with enhancement of tumor lysis comparable to that of BCG. K ODN did not enhance tumor lysis. Similarly, tumor lysis was not enhanced in the absence of CpG ODN (the negative control).

Example 8

Primates Provide a Model System for the Study of CpG ODN

Figure 5A:
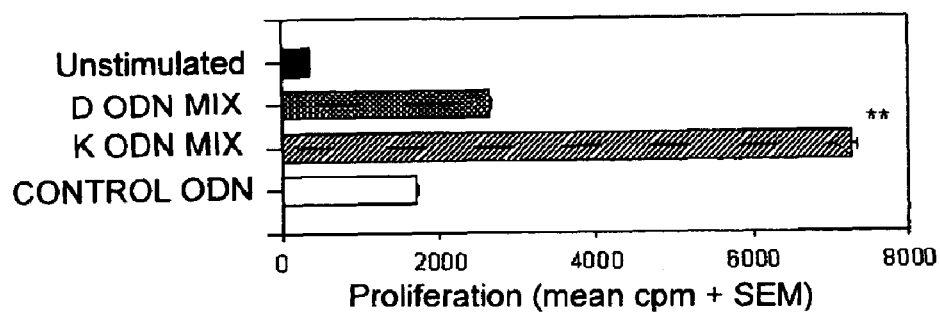
FIG. 5A–C shows the results of a study where PBMC from rhesus macaques (N=12–20) were stimulated in vitro for 72 hours with a mixture of D19, D29 and D35 (1 μM each) or K3 and K123 (1.5 μM each). D122 and K163 were used in the control ODN mixture. Levels of IL-6 (B) and IFNα (C) in culture supernatants were measured by ELISA, while proliferation was measured by [H]³-thymidine uptake (A). Statistical significance was determined by ANOVA of the normalized data. ** $p<0.01$.
Figure 5B:
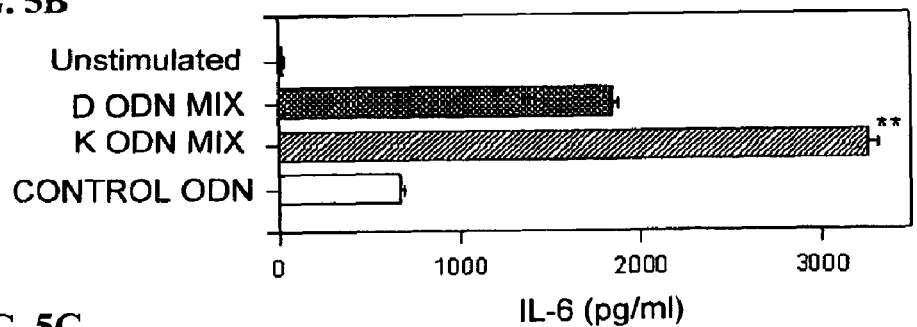
Figure 5C:
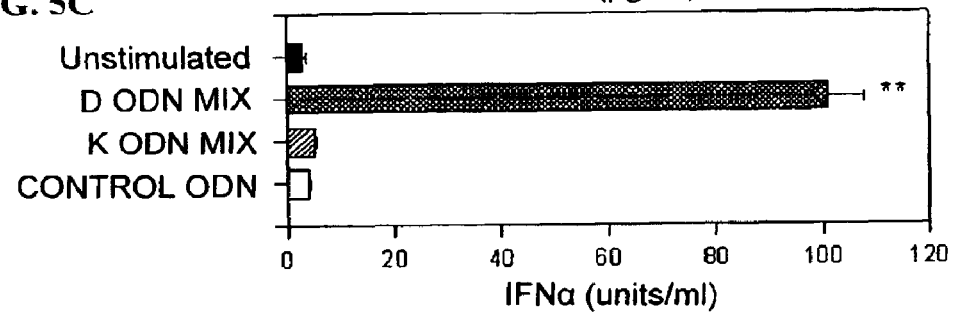

Primate PBMCs respond in a similar manner as human PBMCs to CpG ODN. To demonstrate the similarities, PBMC from normal human donors and Rhesus macaques were stimulated with a panel of K, D or control ODNs, and the IL-6 and IFN-α levels produced were monitored (FIGS. 4 and 5). In both human and monkey PBMC cultures, D ODNs induced the secretion of IFN-α, while K ODNs induced cells proliferation and IL-6 production. Thus, rhesus macaques provide a accurate model system for studying the effects of ODNs in vitro.

Figure 6:
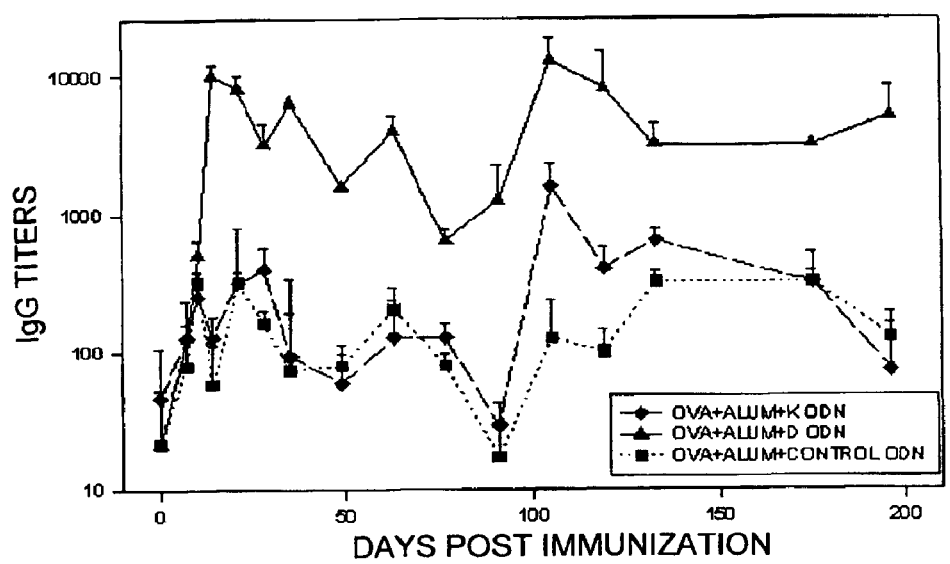
FIG. 6 shows the results of a study where Macaques (3/group) were immunized on day 0 s.c. with 4 μg of OVA plus 125 μg of alum and 250 μg of a mixture of (D19+D29), (K3+K23) or control (AA3M) ODN. Monkeys were boosted 12 weeks later (black arrow). Serum IgG anti-OVA titers were determined by ELISA. Values represent the geometric mean titer±SEM. The anti-OVA IgG titers in the group that received "D" ODN are significantly higher ($p<0.01$).

In order to establish that rhesus macaques were a model system for in vivo experiments, macaques were treated an antigen (OVA) and with either D type (D19 and D29) or K type (K3 and K23) ODNs, or with a control ODN (A23). The anti-OVA IgG titers in the group that received D ODN were significantly higher (FIG. 6), thus demonstrating that D ODN can increase the immune response to a protein antigen in vivo. Thus, rhesus macaque monkeys provide an in vivo model system to study the effects of ODNs.

Example 9

Effect of D ODN on PBMC from Primates

As disclosed in this example, rhesus macaques provide a useful model for assessing the activity of CpG ODN in vivo. In vitro studies established that PBMC from rhesus macaques responded to the same panel of K and D ODN that were highly active on human PBMC. CpG ODN were co-administered with a mixture of ovalbumin plus alum. The ODN significantly boosted the antigen-specific IgG response of macaques, with D being superior to K ODN. A cutaneous leishmania infection model was then used to examine whether CpG ODN could boost protective immunity in primates. The nature, severity, duration and histopathology of the cutaneous disease caused by *L. major* in macaques is quite similar to that in humans (for example see. Amaral et al., *Exp Parasitol* 82:34, 1996). Results indicate that D ODN significantly improve the protection conferred by co-administered heat-killed leishmania vaccine (HKLV).

Materials and Methods Utilized

Rhesus monkeys: Healthy 3 year old female rhesus macaques (*M. mulata*) were obtained from the FDA colony in South Carolina. All studies were ACUC approved and were conducted in an AAALAC accredited facility. Animals were monitored daily by veterinarians. No systemic or local adverse reactions to CpG ODN, OVA or HKLV immunizations were observed. Treatments were administered and peripheral blood samples obtained from ketamine anesthetized animals (10 mg/kg, Ketaject, Phoenix Pharmaceuticals, St Joseph, Md.).

Vaccination groups and protocol: Two in vivo studies were conducted. 1) 3 monkeys/group were immunized subcutaneously (s.c.) and boosted 12 weeks (wk) later with a mixture of 4 μg of ovalbumin, 250 μg ODN and 125 μg of alum (Rehydragel HPA, Reheis, Berkeley Heights, N.J.). 2) 5–6 monkeys/group were immunized s.c. and boosted 4 weeks later with 250 μg of GMP grade HKLV (Biobras, Montes Claros, Brazil) plus 125 μg of alum, as previously described (27). The HKLV was administered alone or combined with 500 μg of ODN. Preliminary studies established that this dose of ODN was active in vivo and well-tolerated. Animals were exposed to non-viable *L. amazonensis* metacycle promastigotes on week 8, a treatment that induced no disease and no change in antibody titer or proliferative response to *Leishmania* antigens when compared to control animals. Animals were challenged on the forehead on week 14 with $10^7$ viable *L. major* (WHOM/IR//173) metacyclic promastigotes i.d. The monkeys developed a typical self-limited in situ lesion characterized by erythema, induration, and ulceration. Lesion size, which reflects the severity of infection, was measured weekly.

Oligodeoxynucleotides: ODN were synthesized by the CBER Core Facility. All ODN had less than <0.1 EU of endotoxin per mg of ODN as assessed by a Limulus amebocyte lysate assay (QCL-1000, BioWhittaker). The following ODN were used in this work:

| D19: | GGTGCATCGATGCAGGGGGG | (SEQ ID NO:1) |
|---|---|---|
| D29: | GGTGCACCGGTGCAGGGGGG | (SEQ ID NO:2) |
| D35: | GGTGCATCGATGCAGGGGGG | (SEQ ID NO:1) |

-continued

| D122: | GGTGCATTGATGCAGGGGGG | (SEQ ID NO:53) |
|---|---|---|
| K3: | ATCGACTCTCGAGCGTTCTC | (SEQ ID NO:3) |
| K123: | TCGTTCGTTCTC | (SEQ ID NO:92) |
| K23: | TCGAGCGTTCTC | (SEQ ID NO:79) |
| K163: | TTGAGTGTTCTC | (SEQ ID NO:109) |
| AA3M: | GGGCATGCATGGGGGG | (SEQ ID NO:124) |

Mononuclear cell preparation: Human and monkey mononuclear cells were isolated by density gradient centrifugation of PBMC over Ficoll-Hypaque as described (see above). Cells were washed 3 times and cultured in RPMI 1640 supplemented with 10% heat-inactivated FCS (FCS), 1.5 mM L-glutamine and 100 U/ml of penicillin/streptomycin at $5 \times 10^5$ cells/well in the presence of 3 μM ODN. Supernatants were collected after 72 hours and tested by ELISA for cytokine and antibody levels.

ELISA: 96-well microtiter plates (Millipore Corp., Bedford, Mass.) were coated with Abs that cross-reactively recognized human and macaque IL-6 (R&D, Minneapolis, Minn.), IFN-α (PBL Biomedical Laboratories, New Brunswick, N.J.), and IgG (Boehringer-Mannheim Biochemicals, Germany). The plates were blocked with PBS-5% BSA. Culture supernatants from PBMC cultures were added, and their cytokine content quantitated by the addition of biotin-labeled anti-cytokine Ab followed by phosphatase-conjugated avidin and phosphatase-specific colorimetric substrate. Standard curves were generated using known amounts of recombinant human cytokine or purified Ig. All assays were performed in triplicate. Titers of antibodies to ovalbumin in sera were assayed on OVA-coated plates.

ELIspot: The number of PBMC secreting IFN-γ in response to soluble leishmania antigen (SLA) were determined by ELIspot as described (Hagiwara *Cytokine* 7:815, 1995). Briefly, Millipore 96-well filtration plates (Millipore Corp., Bedford, Mass.) were coated overnight at 4° C. with 1 μg/ml of anti-human IFN-γ antibodies (Clone GZ4, Alexis, San Diego, Calif.) in PBS and then blocked with PBS-5% BSA for 2 hr. The plates were overlaid with $5 \times 10^5$ cells/well (1–2 series/monkey) and incubated at 37° C. in a humidified 5% $CO_2$ in air incubator for 18 hr in the presence of 25 μg soluble leishmania antigen (SLA). The plates were then washed with water-0.025% Tween and overlaid with biotin conjugated anti-human IFN-γ (clone 76-B-1,Mabtech, Sweden). After 2 hr the plates were washed again and then overlaid with alkaline phosphatase-conjugated streptavidin. Spots were visualized by the addition of 5-bromo-4-chloro-3-indolyl phosphate (Kirkegaard and Perry Laboratories, Gaithersburg, Md.) and counted using the KS ELIspot Imagine System (Carl Zeiss, Inc., Thornwood, N.Y.).

Cell proliferation assay: $10^5$ PBMC/well were incubated with 3 μM of ODN for 68 h, pulsed with 1 μCi of [$^3$H] thymidine and harvested 4 h later. All assays were performed in triplicate.

Statistical Analysis: Statistically significant differences were determined using a 2-tailed non-parametric ANOVA with Dunnett's post test analysis. Differences in lesion sizes were tested by repeated-measures ANOVA using the Proc Mixed procedure from the Statistical Analysis System (SAS). RESULTS:

Response of PBMC from Human and Non-human Primates to K and D ODN

As disclosed herein, human PBMC respond to two structurally distinct classes of CpG ODN. D type ODN triggered the secretion of IFN-γ and IFN-α whereas K ODN induced human PBMC to proliferate and secrete IL-6 and IgM (Table 1). D and K ODN that strongly activated human cells were tested for their ability to stimulate PBMC from rhesus macaques.

The response of rhesus PBMC to "D" ODN was evaluated on the basis of IFN-γ production. Results show that macaque PBMC are activated by the same D ODN that stimulate human PBMC (p<0.002, FIG. 4). In contrast, neither K ODN, nor control ODN that are structurally similar to D ODN but lack the critical CpG dinucleotide, had this effect.

Proliferation and IL-6 secretion were used to compare the response of macaque and human PBMC to K ODN. PBMC from both species were stimulated by K ODN to proliferate (p<0.002) and secrete IL-6 (p<0.01), whereas controls of the same structure as K ODN but lacking the critical CpG motif failed to trigger immune stimulation. The results demonstrated that the pattern of reactivity of PBMC from rhesus macaques (N=20) and humans (N=8–20) to K and D ODN is similar.

Mixtures of ODN were identified that strongly stimulated PBMC from all human donors were utilized in further experiments. These mixtures were tested on PBMC from macaques and found to be uniformly active (FIG. 5). Subsequent in vivo studies were conduced with these ODN mixtures.

Adjuvant Activity of CpG ODN In vivo

Previous studies in mice showed that CpG ODN could boost the immune response to a co-administered protein antigen (such as ovalbumin). This effect was amplified by adding alum to the mixture of CpG ODN plus antigen (for example see Klinman, *Vaccine* 17:19, 1999). Building on these results, macaques were immunized and boosted with a mixture of OVA, alum, and ODN (see FIG. 6). Animals immunized with mixtures containing DODN increased their IgG anti-OVA response by 470-fold after primary (p<0.05) and by 600-fold after secondary (p<0.01) immunization. By comparison, K ODN boosted the IgG Ab response by 7-fold after primary and 35-fold after secondary immunization when compared to pre-treatment values (p<0.05). Macaques immunized with OVA plus control ODN generated only a 4-fold increase in anti-OVA titer. These findings indicate that D ODN are particularly effective at boosting the antigen-specific humoral response to a co-administered antigen.

CpG ODN that activate human immune cells in vitro are only weakly immunostimulatory in mice. The results disclosed herein document that rhesus macaques are a relevant model for examining the in vivo activity of CpG ODN. PBMC from macaques mirrored the response of human PBMC in their response to both "K" and "D" ODN. At the immunostimulatory doses used in this study, neither type of ODN triggered any adverse events. In vivo, broadly immunostimulatory mixtures of K and D ODN boosted antigen-specific IgG responses in macaques immunized with OVA and increased IFN-γ production in animals vaccinated with HKLV. In addition, as described below, D ODN significantly increased the protective response elicited by a co-administered vaccine.

Example 10

Effect of CpG ODN on the Immunogenicity and Protective Efficacy of Heat-Killed Leishmania Vaccine (HKLV)

Previous human clinical trials showed that HKLV was safe, but poorly immunogenic (Handman et al., *Clin Microboiol. Rev.* 14:229, 2001). In addition, HKLV combined with alum and IL-12 induces short-term protective immunity in rhesus macaques (Kenney et al., *J Immunol* 163:4481, 1999), and CpG ODN plus alum increased the immune response to the hepatitis B vaccine in cyalomongus monkeys (Hartmen et al., *J Immunol* 164:1617, 2000).

Figure 7:
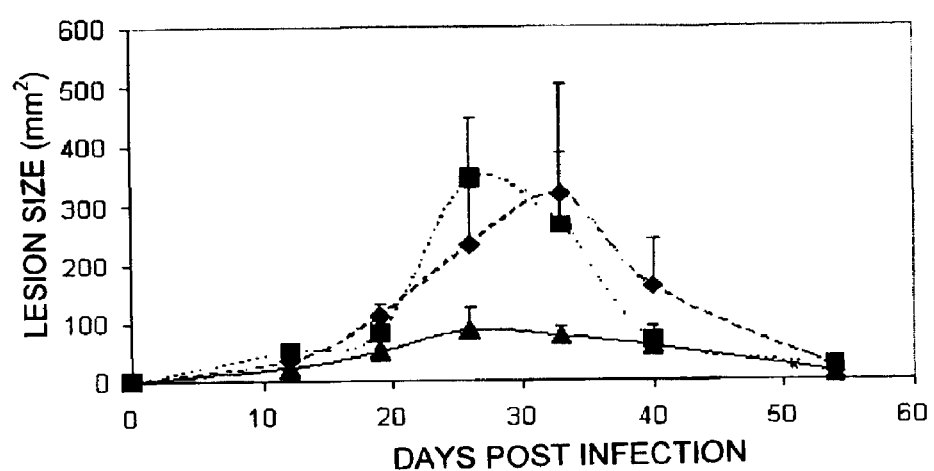
FIG. 7 shows the results of a study were Rhesus macaques were primed subcutaneously (s.c.) with 250 μg of alum-adjuvanted HKLV alone (N=6) or combined with 500 μg of a mixture of (D19, D29 and D35) (N=5) or (K3 and K123) (N=5) and boosted 4 weeks later. On week 14, the monkeys were challenged on the opposite forehead with $10^7$ metacyclic promastigotes. The average size of the resultant lesions is shown as the mean area (calculated as mean diameter/2) $^2 \times pi$). Macaques immunized with HKLV-ALUM-"D"ODN had significantly smaller lesions ($p<0.01$).

Macaques were immunized and boosted with a mixture of HKLV, alum and CpG ODN. PBMC from these animals were isolated 10 days post boost and re-stimulated in vitro with leishmania antigen for 72 hr. As seen in FIG. 7, both K and D ODN significantly increased the number of PBMC triggered to secrete IFN-γ (p<0.05). In contrast, animals immunized with alum-adsorbed HKLV alone showed no increased IFN-γ production when compared to unimmunized controls.

The critical measure of an antigen/adjuvant combination is its ability to induce protective immunity. Vaccinated animals were therefore challenged with $10^7$ *L. major* metacyclic promastigotes. Animals vaccinated with HKLV-alum alone developed typical cutaneous lesions with a peak surface area of 300+60 mm$^2$ 26 days after challenge (FIG. 7). Monkeys vaccinated with HKLV-alum plus K ODN developed lesions of similar size, although the peak lesion formation was slightly delayed. Animals immunized with HKLV-alum plus "D" ODN had significantly smaller lesions (maximal size 80+13 mm$^2$, p<0.05), consistent with a reduced parasite burden.

All animals treated with CpG ODN, either alone or with antigen, remained healthy and active throughout the study. No hematologic or serologic abnormalities were observed 3 days or 9 months after injection and no weight loss or change in behavior were detected following administration of CpG ODN at therapeutic doses As disclosed herein, cutaneous infection of macaques with *L. major* provides a means for testing the protective efficacy of CpG ODN—vaccine combinations. The nature, severity and duration of the cutaneous disease caused by *L. major* in macaques is quite similar to that in humans. The leading leishmania vaccine candidate (HKLV) has proven safe but poorly immunogenic in clinical trials (Handman, *Clin Microboiol. Rev.* 14:229, 2001). Co-administration of both D and K ODN with this alum-adjuvanted HKLV vaccine significantly increased the number of PBMC triggered to secrete IFN-γ when stimulated with leishmania antigen in vitro. However, the critical test of any vaccine/adjuvant combination is its ability to induce protective immunity. Results show that the cutaneous lesions of macaques vaccinated with HKLV plus "D" ODN were significantly reduced when compared to HKLV-alum alone. A reduction in lesion size correlates with a reduced parasite load. Thus, without being bound by theory, the findings suggest that the ability of D ODN to stimulate IFN-γ and IFN α production while promoting the maturation of antigen presenting cells can be useful for the induction of a protective response against leishmania. In addition, without being bound by theory, the findings suggest that the ability of D ODN to stimulate IFN-γ and IFN α production while promoting the maturation of antigen presenting cells can be useful as a vaccine adjuvant.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and it is intended that the invention may be practiced otherwise than as specifically described herein. Accordingly, this invention includes all modifications encompassed within the spirit and scope of the invention as defined by the following claims.

We claim:

1. A substantially pure or isolated oligodeoxynucleotide of between 18 and 30 nucleotides in length, comprising any one of

| | |
|---|---|
| 5'-$X_1X_2$TGCATCGATGCAGGGGGG-3'; | (SEQ ID NO:12) |
| 5'-$X_1X_2$TGCACCGGTGCAGGGGGG-3'; | (SEQ ID NO:13) |
| 5'-$X_1X_2$TGCGTCGACGCAGGGGGG-3'; | (SEQ ID NO:15) |
| 5'-$X_1X_2$TGCGCCGGCGCAGGGGGG-3'; | (SEQ ID NO:17) |
| 5'-GGTGCATCGATGCAGGGGGG-3'; | (SEQ ID NO:1) |
| 5'-GGTGCGTCGACGCAGGGGGG-3'; | (SEQ ID NO:31) |
| 5'-GGTGCACCGGTGCAGGGGGG-3'; or | (SEQ ID NO:2) |
| 5'-GGTGCATCGATGCAGGGGG-3'; | (SEQ ID NO:73). |

2. The stabilized oligodeoxynucleotide of claim 1, wherein the oligodeoxynucleotide is modified to prevent degradation.

3. The stabilized oligodeoxynucleotide of claim 1, wherein the oligodeoxynucleotide has a phosphate backbone modification.

4. The stabilized oligodeoxynucleotide of claim 3, wherein the phosphate backbone modification is a phosphorothioate backbone modification.

5. An oligodeoxynucleotide delivery complex comprising the stabilized oligodeoxynucleotide of claim 1, and a targeting moiety.

6. The stabilized oligodeoxynucleotide delivery complex of claim 5, wherein the targeting moiety is selected from the group consisting of a cholesterol, a virosome, a liposome, a lipid, and a target cell specific binding agent.

7. The oligodeoxynucleotide of delivery complex of claim 5, wherein the stabilized oligodeoxynucleotide and the targeting moiety are covalently linked.

8. A pharmacological composition comprising the stabilized oligodeoxynucleotide of claim 1, and a pharmacologically acceptable carrier.

9. The stabilized oligodeoxynucleotide of claim 1, wherein the stabilized oligonucleotide comprises at least one phosphodiester base.

10. The stabilized oligodeoxynucleotide of claim 9, wherein the stabilized oligonucleotide comprises a plurality of phosphodiester bases.

11. The stabilized oligodeoxynucleotide of claim 9, wherein the stabilized oligonucleotide comprises one or more phosphorothioate bases.

12. The stabilized oligodeoxynucleotide of claim 9, wherein the stabilized oligonucleotide comprises a plurality of phosphorothioate bases.

13. The stabilized oligodeoxynucleotide of claim 1, further comprising at least one additional G in the 5' far flanking region.

* * * * *

UNITED STATES PATENT AND TRADEMARK OFFICE
CERTIFICATE OF CORRECTION

PATENT NO. : 6,977,245 B2 Page 1 of 1
APPLICATION NO. : 10/068160
DATED : December 20, 2005
INVENTOR(S) : Klinman et al.

It is certified that error appears in the above-identified patent and that said Letters Patent is hereby corrected as shown below:

In the claims:

Claim 1 is corrected to read:

1. A substantially pure or isolated stabilized oligodeoxynucleotide of between 18 and 30 nucleotides in length comprising any one of
5'-$X_1X_2$TGCATCGATGCAGGGGGG -3' (SEQ ID NO:12);
5'-$X_1X_2$TGCACCGGTGCAGGGGGG -3' (SEQ ID NO:13);
5'-$X_1X_2$TGCGTCGACGCAGGGGGG -3' (SEQ ID NO:14);
5'-$X_1X_2$TGCGCCGGCGCAGGGGGG -3' (SEQ ID NO:17);
5'-GGTGCATCGATGCAGGGGGG -3' (SEQ ID NO: 1);
5'-GGTGCGTCGACGCAGGGGGG -3' (SEQ ID NO: 31);
5'-GGTGCACCGGTGCAGGGGGG -3' (SEQ ID NO: 2); or,
5'-GGTGCATCGATGCAGGGGG -3' (SEQ ID NO: 72).

Claim 7 is corrected to read:

7. The oligodeoxynucleotide delivery complex of claim 5, wherein the stabilized oligodeoxynucleotide and the targeting moiety are covalently linked.

Signed and Sealed this

Eighteenth Day of September, 2007

JON W. DUDAS
*Director of the United States Patent and Trademark Office*